(12) United States Patent
Lemaire

(10) Patent No.: US 11,464,957 B2
(45) Date of Patent: Oct. 11, 2022

(54) COMPACT HIGH MECHANICAL ENERGY STORAGE AND LOW TRIGGER FORCE ACTUATOR FOR THE DELIVERY OF MICROPROJECTION ARRAY PATCHES (MAP)

(71) Applicant: Vaxxas Pty Limited, Sydney (AU)

(72) Inventor: Pierre Armand Vincent Lemaire, Norman Park (AU)

(73) Assignee: VAXXAS PTY LIMITED, Sydney (AU)

( * ) Notice: Subject to any disclaimer, the term of this patent is extended or adjusted under 35 U.S.C. 154(b) by 0 days.

(21) Appl. No.: 16/636,467

(22) PCT Filed: Aug. 3, 2018

(86) PCT No.: PCT/AU2018/050810
§ 371 (c)(1),
(2) Date: Feb. 4, 2020

(87) PCT Pub. No.: WO2019/023757
PCT Pub. Date: Feb. 7, 2019

(65) Prior Publication Data
US 2020/0368511 A1    Nov. 26, 2020

Related U.S. Application Data

(60) Provisional application No. 62/605,205, filed on Aug. 4, 2017.

(51) Int. Cl.
*A61M 37/00* (2006.01)
*B29C 45/56* (2006.01)

(52) U.S. Cl.
CPC ....... *A61M 37/0015* (2013.01); *B29C 45/561* (2013.01); *A61M 2037/0023* (2013.01);
(Continued)

(58) Field of Classification Search
CPC ...... A61M 37/0015; A61M 2037/0023; A61M 2037/0053; A61M 2037/0061; B29C 45/561
See application file for complete search history.

(56) References Cited

U.S. PATENT DOCUMENTS

2,213,830 A    9/1940  Anastasi
2,881,500 A    4/1959  Furness
(Continued)

FOREIGN PATENT DOCUMENTS

CN    1149018 A    5/1997
CN    101214395 A    7/2008
(Continued)

OTHER PUBLICATIONS

Aichele et al., "Antiviral Cytotoxic T Cell Response Induced By in Vivo Priming With a Free Synthetic Peptide," *J Exp. Med.* 171:1815-1820, 1990.
(Continued)

*Primary Examiner* — Amber R Stiles
(74) *Attorney, Agent, or Firm* — Seed IP Law Group LLP

(57) ABSTRACT

The present invention relates to devices and methods for providing a triggering mechanism which lowers the trigger force to activate the trigger mechanism to a comfortable range of while still preserving or increasing the speed at which the triggering mechanism accelerates or imparts velocity to a device attached to the triggering mechanism. The present invention further relates to improved applicators for administering microprojection arrays to skin and methods of administering microprojection arrays. In particular, the present invention relates to compact stable self-contained mechanical energy storage for delivery of a medical device such as a microprojection array.

14 Claims, 35 Drawing Sheets

(52) U.S. Cl.
CPC ............... *A61M 2037/0053* (2013.01); *A61M 2037/0061* (2013.01)

(56) References Cited

U.S. PATENT DOCUMENTS

| | | | |
|---|---|---|---|
| 4,702,799 A | 10/1987 | Tuot | |
| 5,017,007 A | 5/1991 | Milne et al. | |
| 5,201,992 A | 4/1993 | Marcus et al. | |
| 5,353,792 A | 10/1994 | Lubbers et al. | |
| 5,449,064 A | 9/1995 | Hogan et al. | |
| 5,457,041 A | 10/1995 | Ginaven et al. | |
| 5,461,482 A | 10/1995 | Wilson et al. | |
| 5,499,474 A | 3/1996 | Knooihuizen | |
| 5,527,288 A | 6/1996 | Gross et al. | |
| 5,611,806 A | 3/1997 | Jang | |
| 5,657,138 A | 8/1997 | Lewis et al. | |
| 5,859,937 A | 1/1999 | Nomura | |
| 5,870,806 A * | 2/1999 | Black, Jr. | A44B 17/0023 24/662 |
| 5,922,356 A | 7/1999 | Koseki et al. | |
| 5,928,207 A | 7/1999 | Pisano et al. | |
| 5,943,075 A | 8/1999 | Lee et al. | |
| 6,052,652 A | 4/2000 | Lee | |
| 6,233,797 B1 | 5/2001 | Neely et al. | |
| 6,287,556 B1 | 9/2001 | Portnoy et al. | |
| 6,299,621 B1 | 10/2001 | Fogarty et al. | |
| 6,334,856 B1 | 1/2002 | Allen et al. | |
| 6,352,697 B1 | 3/2002 | Cox et al. | |
| 6,454,755 B1 | 9/2002 | Godshall | |
| 6,463,312 B1 | 10/2002 | Bergveld et al. | |
| 6,478,738 B1 | 11/2002 | Hirabayashi et al. | |
| 6,503,231 B1 | 1/2003 | Prausnitz et al. | |
| 6,533,949 B1 | 3/2003 | Yeshurun et al. | |
| 6,537,242 B1 | 3/2003 | Palmer | |
| 6,537,264 B1 | 3/2003 | Cormier et al. | |
| 6,551,849 B1 | 4/2003 | Kenney | |
| 6,557,849 B2 | 5/2003 | Wyss | |
| 6,558,361 B1 | 5/2003 | Yeshurun | |
| 6,565,532 B1 | 5/2003 | Yuzhakov et al. | |
| 6,589,202 B1 | 7/2003 | Powell | |
| 6,591,124 B2 | 7/2003 | Sherman et al. | |
| 6,610,382 B1 | 8/2003 | Kobe et al. | |
| 6,743,211 B1 | 6/2004 | Prausnitz et al. | |
| 6,749,575 B2 | 6/2004 | Matriano et al. | |
| 6,855,372 B2 | 2/2005 | Trautman et al. | |
| 6,881,203 B2 | 4/2005 | Delmore | |
| 6,908,453 B2 | 6/2005 | Fleming et al. | |
| 6,923,764 B2 | 8/2005 | Aceti et al. | |
| 6,931,277 B1 | 8/2005 | Yuzhakov et al. | |
| 6,945,952 B2 | 9/2005 | Kwon | |
| 7,022,071 B2 | 4/2006 | Schaupp et al. | |
| 7,045,069 B2 | 5/2006 | Ozeryansky | |
| 7,048,723 B1 | 5/2006 | Frazier et al. | |
| 7,097,631 B2 | 8/2006 | Trautman et al. | |
| 7,169,600 B2 | 1/2007 | Hoss et al. | |
| 7,211,062 B2 | 5/2007 | Kwon | |
| 7,250,037 B2 | 7/2007 | Shermer et al. | |
| 7,316,665 B2 | 1/2008 | Laurent et al. | |
| 7,753,888 B2 | 7/2010 | Mukerjee et al. | |
| 8,052,633 B2 | 11/2011 | Kendall | |
| 8,062,573 B2 | 11/2011 | Kwon | |
| 8,267,889 B2 | 9/2012 | Cantor et al. | |
| 8,414,548 B2 | 4/2013 | Yuzhakov | |
| 8,540,672 B2 | 9/2013 | McAllister | |
| 8,734,697 B2 | 5/2014 | Chen et al. | |
| 8,883,015 B2 | 11/2014 | Kendall et al. | |
| 9,199,976 B2 | 12/2015 | Smythe et al. | |
| 9,220,678 B2 | 12/2015 | Kendall et al. | |
| 9,283,365 B2 | 3/2016 | Kendall et al. | |
| 9,387,000 B2 | 7/2016 | Corrie et al. | |
| 9,572,969 B2 | 2/2017 | Kendall | |
| 9,888,932 B2 | 2/2018 | Kendall | |
| 9,943,673 B2 | 4/2018 | Kendall et al. | |
| 10,022,322 B2 | 7/2018 | Kendall et al. | |
| 10,751,072 B2 | 8/2020 | Kendall | |
| 11,103,259 B2 | 8/2021 | Crichton et al. | |
| 11,147,954 B2 | 10/2021 | Junger et al. | |
| 11,179,553 B2 | 11/2021 | Kendall et al. | |
| 11,207,086 B2 | 12/2021 | Kendall | |
| 2002/0008530 A1 | 1/2002 | Kim et al. | |
| 2002/0016562 A1 | 2/2002 | Cormier et al. | |
| 2002/0032415 A1 | 3/2002 | Trautman et al. | |
| 2002/0128599 A1 | 9/2002 | Cormier et al. | |
| 2002/0133129 A1 | 9/2002 | Arias et al. | |
| 2002/0169411 A1 | 11/2002 | Sherman et al. | |
| 2002/0177839 A1 | 11/2002 | Cormier et al. | |
| 2003/0036710 A1 | 2/2003 | Matriano et al. | |
| 2003/0199810 A1 | 10/2003 | Trautman et al. | |
| 2003/0199811 A1 | 10/2003 | Sage | |
| 2003/0220656 A1 | 11/2003 | Gartstein et al. | |
| 2004/0002121 A1 | 1/2004 | Regan et al. | |
| 2004/0004649 A1 | 1/2004 | Bibi et al. | |
| 2004/0008241 A1 | 1/2004 | Junhua | |
| 2004/0039397 A1 | 2/2004 | Weber et al. | |
| 2004/0049150 A1 | 3/2004 | Dalton et al. | |
| 2004/0087992 A1 | 5/2004 | Kobe et al. | |
| 2004/0161470 A1 | 8/2004 | Andrianov et al. | |
| 2005/0042866 A1 | 2/2005 | Klapproth et al. | |
| 2005/0089553 A1 | 4/2005 | Cormier | |
| 2005/0089554 A1 | 4/2005 | Cormier et al. | |
| 2005/0126710 A1 | 6/2005 | Laermer et al. | |
| 2005/0137531 A1 | 6/2005 | Prausnitz et al. | |
| 2005/0143713 A1 | 6/2005 | Delmore et al. | |
| 2005/0197308 A1 | 9/2005 | Dalton et al. | |
| 2005/0261632 A1 | 11/2005 | Xu | |
| 2006/0012780 A1 | 1/2006 | Nishiyama et al. | |
| 2006/0015061 A1 | 1/2006 | Kuo et al. | |
| 2006/0055724 A1 | 3/2006 | Krawczyk et al. | |
| 2006/0074376 A1 | 4/2006 | Kwon | |
| 2006/0195125 A1 | 8/2006 | Sakakine et al. | |
| 2006/0202385 A1 | 9/2006 | Xu et al. | |
| 2006/0264782 A1 | 11/2006 | Holmes et al. | |
| 2007/0027474 A1 | 2/2007 | Lasner | |
| 2007/0060867 A1 | 3/2007 | Xu | |
| 2007/0078376 A1 | 4/2007 | Smith | |
| 2007/0224252 A1 | 9/2007 | Trautman et al. | |
| 2007/0264749 A1 | 11/2007 | Birkmeyer | |
| 2007/0270738 A1 | 11/2007 | Wu | |
| 2007/0293815 A1 | 12/2007 | Chan et al. | |
| 2007/0299388 A1 | 12/2007 | Chan et al. | |
| 2008/0009811 A1 | 1/2008 | Cantor | |
| 2008/0108959 A1 | 5/2008 | Jung et al. | |
| 2008/0114298 A1* | 5/2008 | Cantor | A61M 37/0015 604/117 |
| 2008/0136874 A1 | 6/2008 | Tsukamura | |
| 2008/0183144 A1* | 7/2008 | Trautman | A61M 37/0015 604/272 |
| 2008/0245764 A1 | 10/2008 | Pirk et al. | |
| 2008/0287858 A1 | 11/2008 | Duan | |
| 2008/0312610 A1 | 12/2008 | Binks | |
| 2008/0312669 A1 | 12/2008 | Vries et al. | |
| 2009/0017210 A1 | 1/2009 | Andrianov | |
| 2009/0041810 A1 | 2/2009 | Andrianov et al. | |
| 2009/0198189 A1 | 8/2009 | Simons et al. | |
| 2009/0292254 A1 | 11/2009 | Tomono | |
| 2010/0156998 A1 | 6/2010 | Matsumoto et al. | |
| 2010/0221314 A1 | 9/2010 | Matsudo et al. | |
| 2010/0222743 A1 | 9/2010 | Frederickson et al. | |
| 2010/0256568 A1 | 10/2010 | Frederickson et al. | |
| 2011/0021996 A1 | 1/2011 | Lee et al. | |
| 2011/0028905 A1 | 2/2011 | Takada | |
| 2011/0059150 A1 | 3/2011 | Kendall et al. | |
| 2011/0160069 A1 | 6/2011 | Corrie et al. | |
| 2011/0223542 A1 | 9/2011 | Kendall et al. | |
| 2011/0245776 A1 | 10/2011 | Kendall et al. | |
| 2011/0276027 A1 | 11/2011 | Trautman et al. | |
| 2011/0288484 A1 | 11/2011 | Kendall et al. | |
| 2012/0027810 A1 | 2/2012 | Chen et al. | |
| 2012/0041412 A1 | 2/2012 | Roth | |
| 2012/0083741 A1 | 4/2012 | Kendall et al. | |
| 2012/0083762 A1 | 4/2012 | Kendall | |
| 2012/0109065 A1 | 5/2012 | Backes | |
| 2012/0136312 A1 | 5/2012 | Terahara et al. | |
| 2012/0220981 A1 | 8/2012 | Soo et al. | |

(56) References Cited

U.S. PATENT DOCUMENTS

| | | | |
|---|---|---|---|
| 2012/0265141 A1 | 10/2012 | Kalpin et al. | |
| 2012/0277629 A1 | 11/2012 | Bernstein et al. | |
| 2012/0330250 A1 | 12/2012 | Kuwahara et al. | |
| 2013/0079666 A1* | 3/2013 | Gonzalez-Zugasti | A61B 5/15117 600/583 |
| 2013/0131598 A1 | 5/2013 | Trautman et al. | |
| 2013/0150822 A1 | 6/2013 | Ross | |
| 2013/0158482 A1 | 6/2013 | Davis et al. | |
| 2013/0190794 A1 | 7/2013 | Kendall et al. | |
| 2013/0296790 A1* | 11/2013 | Masaoka | A61M 37/0015 604/173 |
| 2013/0337150 A1 | 12/2013 | Biemans | |
| 2014/0243747 A1 | 8/2014 | Tokumoto et al. | |
| 2014/0257188 A1 | 9/2014 | Kendall et al. | |
| 2014/0276366 A1 | 9/2014 | Bourne et al. | |
| 2014/0276378 A1 | 9/2014 | Chen et al. | |
| 2015/0057604 A1 | 2/2015 | Arami et al. | |
| 2015/0080844 A1 | 3/2015 | Donovan et al. | |
| 2016/0015952 A1 | 1/2016 | Omachi et al. | |
| 2016/0058697 A1 | 3/2016 | Kendall et al. | |
| 2016/0220803 A1 | 8/2016 | Kendall et al. | |
| 2016/0271381 A1 | 9/2016 | Falo, Jr. et al. | |
| 2016/0310412 A1 | 10/2016 | Tanoue et al. | |
| 2017/0014336 A1 | 1/2017 | Kuruma et al. | |
| 2017/0056637 A1 | 3/2017 | Unger et al. | |
| 2017/0065804 A1 | 3/2017 | Uemura | |
| 2017/0182301 A1 | 6/2017 | Kendall | |
| 2017/0239458 A1 | 8/2017 | Kato et al. | |
| 2017/0282417 A1 | 10/2017 | Okano et al. | |
| 2017/0296465 A1 | 10/2017 | Yoshida et al. | |
| 2017/0361082 A1 | 12/2017 | Okano et al. | |
| 2017/0368322 A1 | 12/2017 | Kato et al. | |
| 2018/0015271 A1 | 1/2018 | Junger et al. | |
| 2018/0161050 A1 | 6/2018 | Kendall | |
| 2018/0250503 A1 | 9/2018 | Enomoto et al. | |
| 2018/0263641 A1 | 9/2018 | Crichton et al. | |
| 2018/0264244 A1 | 9/2018 | Meliga et al. | |
| 2018/0326726 A1 | 11/2018 | Wang et al. | |
| 2019/0001109 A1 | 1/2019 | Kim et al. | |
| 2019/0046479 A1 | 2/2019 | Pathak | |
| 2020/0246450 A1 | 8/2020 | Junger et al. | |
| 2020/0246545 A1 | 8/2020 | Langer et al. | |
| 2020/0368511 A1 | 11/2020 | Lemaire | |
| 2020/0405331 A1 | 12/2020 | Kendall | |
| 2021/0170152 A1 | 6/2021 | Kendall et al. | |
| 2021/0244926 A1 | 8/2021 | Meliga et al. | |
| 2021/0270599 A1 | 9/2021 | Junger et al. | |

FOREIGN PATENT DOCUMENTS

| | | |
|---|---|---|
| CN | 101297989 A | 11/2008 |
| EP | 0 139 286 A2 | 5/1985 |
| EP | 0 732 208 A1 | 9/1996 |
| EP | 1 695 734 B1 | 6/2008 |
| EP | 2 213 284 A1 | 8/2010 |
| EP | 2 327 419 A1 | 6/2011 |
| EP | 2 568 174 A1 | 3/2013 |
| EP | 2 835 147 A1 | 2/2015 |
| JP | 2003-127430 A | 5/2003 |
| JP | 2007-260889 A | 11/2007 |
| JP | 2008114561 A | 5/2008 |
| JP | 2010-071845 A | 4/2010 |
| JP | 2013043034 A | 3/2013 |
| JP | 2016-166769 A | 9/2016 |
| WO | 91/06571 A1 | 5/1991 |
| WO | 94/24281 A1 | 10/1994 |
| WO | 98/28037 A1 | 7/1998 |
| WO | 98/28038 A1 | 7/1998 |
| WO | 99/02694 A1 | 1/1999 |
| WO | 99/42564 A2 | 8/1999 |
| WO | 99/64580 A1 | 12/1999 |
| WO | 00/05339 A1 | 2/2000 |
| WO | 00/42215 A1 | 7/2000 |
| WO | 00/74763 A2 | 12/2000 |
| WO | 00/74764 A1 | 12/2000 |
| WO | 01/33614 A1 | 5/2001 |
| WO | 01/85207 A2 | 11/2001 |
| WO | 02/064193 A2 | 8/2002 |
| WO | 02/074173 A2 | 9/2002 |
| WO | 02/075794 A2 | 9/2002 |
| WO | 02/085446 A2 | 10/2002 |
| WO | 02/085447 A2 | 10/2002 |
| WO | 2002/100476 A2 | 12/2002 |
| WO | 03/020359 A2 | 3/2003 |
| WO | 03/026732 A2 | 4/2003 |
| WO | 03/048031 A2 | 6/2003 |
| WO | 03/053258 A1 | 7/2003 |
| WO | 03/078925 A2 | 9/2003 |
| WO | 03/092785 A1 | 11/2003 |
| WO | 2004/000389 A2 | 12/2003 |
| WO | 2004/024224 A1 | 3/2004 |
| WO | 2005/049108 A2 | 6/2005 |
| WO | 2005/060621 A2 | 7/2005 |
| WO | 2005/069736 A2 | 8/2005 |
| WO | 2005/072630 A1 | 8/2005 |
| WO | 2005/123173 A1 | 12/2005 |
| WO | 2006/055795 A1 | 5/2006 |
| WO | 2006/055799 A1 | 5/2006 |
| WO | 2006/101459 A1 | 9/2006 |
| WO | 2006/108185 A1 | 10/2006 |
| WO | 2006/116281 A2 | 11/2006 |
| WO | 2006/138719 A1 | 12/2006 |
| WO | 2007/002123 A2 | 1/2007 |
| WO | 2007/002521 A2 | 1/2007 |
| WO | 2007/012114 A1 | 2/2007 |
| WO | 2007/030477 A2 | 3/2007 |
| WO | 2007/054090 A1 | 5/2007 |
| WO | 2007/061781 A1 | 5/2007 |
| WO | 2007/070004 A1 | 6/2007 |
| WO | 2007/080427 A2 | 7/2007 |
| WO | 2007/124411 A1 | 11/2007 |
| WO | 2007/127976 A2 | 11/2007 |
| WO | 2008/010681 A1 | 1/2008 |
| WO | 2008/011625 A2 | 1/2008 |
| WO | 2008/053481 A1 | 5/2008 |
| WO | 2008/069566 A1 | 6/2008 |
| WO | 2008/083209 A2 | 7/2008 |
| WO | 2008/091602 A2 | 7/2008 |
| WO | 2009/040548 A1 | 4/2009 |
| WO | 2009/066763 A1 | 5/2009 |
| WO | WO 2009077859 A1 | 6/2009 |
| WO | 2009/079712 A1 | 7/2009 |
| WO | 2009/081122 A1 | 7/2009 |
| WO | 2009/097660 A1 | 8/2009 |
| WO | 2009/140735 A1 | 11/2009 |
| WO | 2010/042996 A1 | 4/2010 |
| WO | 2010/071918 A1 | 7/2010 |
| WO | 2010/109471 A1 | 9/2010 |
| WO | 2011/105496 A1 | 9/2011 |
| WO | 2011/116388 A1 | 9/2011 |
| WO | 2012/119907 A1 | 9/2012 |
| WO | 2012/122162 A1 | 9/2012 |
| WO | 2013/053022 A1 | 4/2013 |
| WO | 2013/055641 A1 | 4/2013 |
| WO | 2014/058746 A1 | 4/2014 |
| WO | 2015/034924 A1 | 3/2015 |
| WO | 2016/123665 A1 | 8/2016 |
| WO | 2016/143514 A1 | 9/2016 |
| WO | 2017/123652 A1 | 7/2017 |
| WO | 2018/119174 A1 | 6/2018 |

OTHER PUBLICATIONS

Albert et al., "Dendritic cells acquire antigen from apoptotic cells and induce class I-restricted CTLs," *Nature* 392:86-89, 1998.

Albert et al., "Tumor-specific killer cells in paraneoplastic cerebellar degeneration," *Nature Medicine* 4(11):1321-1324, 1998.

Anderson, "Cutaneous Microdialysis: Is it Worth the Sweat?" *Journal of Investigative Dermatology* 126:1207-1209, 2006.

Athanasopoulos et al., "Gene therapy vectors based on adeno-associated virus: Characterstics and applications to acquired and

(56) References Cited

OTHER PUBLICATIONS inherited diseases (Review)," *International Journal of Molecular Medicine* 6:363-375, 2000.
Australian Examination Report dated Apr. 11, 2016 for Australian Application No. 2012323782, 3 pages.
Australian Examination Report dated Jan. 9, 2017 for Australian Application No. 2012323782, 4 pages.
Australian Examination Report dated Mar. 27, 2013 for Australian Application No. 2009212106, 5 pages.
Bachmann et al., "Dendiritic cells process exogenous viral proteins and virus-like particles for class I presentation to CD8+ cytotoxic T lymphocytes," *Eur. J. Immunol.* 26:2595-2600, 1996.
Boehm et al., "Inkjet printing for pharmaceutical applications," *Materials Today* 17(5):247-252, 2014.
Camilli et al., "Listeria monocytogenes Mutants Lacking Phosphatidylinositol-specific Phospholipase C Are Avirulent," *J. Exp. Med.* 173:751-754, 1991.
Canadian Examination Report dated Apr. 23, 2015 for Canadian Application No. 2,749,347, 4 pages.
Canadian Examination Report dated Feb. 17, 2015 for Canadian Application No. 2,745,339, 4 pages.
Chinese Office Action dated Dec. 28, 2012 for Chinese Application No. 200980104635.3, 6 pages. (w/English Translation).
Chinese Office Action dated Feb. 17, 2012 for Chinese Application No. 200980104635.3, 13 pages. (w/English Translation).
Chinese Office Action dated Sep. 24, 2012 for Chinese Application No. 200980104635.3, 9 pages. (w/English Translation).
Cormier et al., "Transdermal delivery of desmopressin using a coated microneedle array patch system," *Journal of Controlled Release* 97:503-511, 2004.
Cox et al., "Adjuvants—a classification and review of their modes of action," *Vaccine* 15(3):248-256, 1997.
Crichton et al., "The effect of strain rate on the precision of penetration of short densely-packed microprojection array patches coated with vaccine," *Biomaterials* 37:4562-4572, 2010.
Crichton et al., "The viscoelastic, hyperelastic and scale dependent behaviour of freshly excised individual skin layers," *Biomaterials* 32:4670-4681, 2011.
Desai et al., "Understanding release kinetics of biopolymer drug delivery microcapsules for biomedical applications," *Materials Science and Engineering B* 168:127-131, 2010.
Dreyer, "Microneedles:Microprocessing in Medicine," *ENMA465 Project*, May 10, 2004. (23 pages).
European Search Report dated Jul. 20, 2012 for European Application No. 09833918.7, 9 pages.
European Search Report dated Nov. 10, 2015 for European Application No. 12840561.0, 11 pages.
European Search Report dated Sep. 10, 2018, for European Application No. 16746000.5, 3 pages.
European Search Report dated Sep. 26, 2014 for European Application No. 09707729.1, 9 pages.
Feng et al., "Molecular Biomarkers for Cancer Detection in Blood and Bodily Fluids," *Critical Reviews in Clinical Laboratory Sciences* 43(5-6):497-560, 2006.
Fernando et al., "Potent Immunity to Low Doses of Influenza Vaccine by Probabilistic Guided Micro-Targeted Skin Delivery in a Mouse Model," *PLoS One* 5(4):e10266, 2010. (11 pages).
Gao et al., "Priming of Influenza Virus-Specific Cytotoxic T Lymphocytes Vivo by Short Synthetic Peptides," The Journal of Immunology 147(10):3268-3273, 1991.
Garafalo et al., "Histamine release and therapy of severe dermatographism," *J. Allergy Clin. Immunol.* 68(2):103-105, 1981.
Gardeniers et al., "Silicon Micromachined Hollow Microneedles for Transdermal Liquid Transport," *Journal of Microelectromechanical Systems* 12(6):855-862, 2003.
Gill et al., "Coated microneedles for transdermal delivery," *Journal of Controlled Release* 117:227-237, 2007.
Gill et al., "Coating Formulations for Microneedles," *Pharmaceutical Research* 24(7):1369-1380, 2007.

Henry et al., "Microfabricated Microneedles: A Novel Approach to Transdermal Drug Delivery," *Journal of Pharmaceutical Sciences* 87(8):922-925, 1998.
International Preliminary Report on Patentability dated Feb. 4, 2020 for International Application No. PCT/AU2018/050810, 9 pages.
International Preliminary Report on Patentability dated Jun. 29, 2010 for International Application No. PCT/AU2008/001903, 7 pages.
International Preliminary Report on Patentability dated Jun. 7, 2006 for International Application No. PCT/GB2005/000336, 9 pages.
International Preliminary Report on Patentability dated Nov. 14, 2012 for International Application No. PCT/AU2011/000890, 6 pages.
International Search Report dated Jul. 30, 2018, for International Application No. PCT/AU2018/050298, 6 pages.
International Search Report dated Sep. 13, 2018, for International Application No. PCT/AU2018/050847, 4 pages.
International Search Report dated Aug. 1, 2018, for International Application No. PCT/AU2018/050586, 4 pages.
International Search Report dated Dec. 22, 2016 for International Application No. PCT/AU2016/050907, 5 pages.
International Search Report dated Dec. 6, 2016 for International Application No. PCT/AU2016/050867, 12 pages.
International Search Report dated Feb. 20, 2009, for International Application No. PCT/AU2008/001903, 5 pages.
International Search Report dated Feb. 20, 2013 for International Application No. PCT/AU2012/001289, 13 pages.
International Search Report dated Mar. 7, 2016 for International Application No. PCT/AU2016/050056, 6 pages.
International Search Report dated Nov. 8, 2018, for International Application No. PCT/AU2018/050810, 8 pages.
International Search Report dated Oct. 25, 2011 for International Application No. PCT/AU2011/000890, 4 pages.
Ito et al., "Evaluation of self-dissolving needles containing low molecular weight heparin (LMWH) in rats," *International Journal of Pharmaceutics* 349:124-129, 2008.
Ito et al., "Feasibility of microneedles for percutaneous absorption of insulin," *European Journal of Pharmaceutical Sciences* 29:82-88, 2006.
Ito et al., "Self-dissolving microneedles for the percutaneous absorption of EPO in mice," *Journal of Drug Targeting* 14(5):255-261, 2006.
Jondal et al., "MHC Class I-Restricted CTL Responses to Exogenous Antigens," *Immunity* 5:295-302, 1996.
Kay et al., "Viral vectors for gene therapy: the art of turning infectious agents into vehicles of therapeutics," *Nature Medicine* 7(1):33-40, 2001.
Kendall et al., "The mechanical properties of the skin epidermis in relation to targeted gene and drug delivery," *Biomaterials* 28:4968-4977, 2007.
Kuzu et al., "In vivo priming effect during various stages of ontogeny of an influenza A virus nucleoprotein peptide," *Eur. J. Immunol.* 23:1397-1400, 1993.
Kwon, "Acne Treatment by a Dissolvable Micro-Needle Patch," TheraJect Inc., 2006. (2 pages).
Kwon, "In Vitro Evaluation of Transdermal Drug Delivery by a Micro-needle Patch," Controlled Release Society 31st Annual Meeting Transactions #115, 2006. (2 pages).
Kwon, "In Vitro Modeling of Transdermal PTH Delivery by Dissovling Micro-needle Patch," TherJect Inc., 2007. (2 pages).
Kwon, "Rapid Intradermal Drug Delivery by a Dissovable Micro-Needle Patch," Controlled Release Society 32nd Annual Meeting & Exposition Transactions #306, 2005. (2 pages).
Lee et al., "Dissolving microneedles for transdermal drug delivery," *Biomaterials* 29:2113-2124, 2008.
Lin et al., "Silicon-Processed Microneedles," *IEEE Journal of Microelectromechanical Systems* 8(1):78-84, 1999.
Ma et al., "Coating solid dispersions on microneedles via a molten dip coating method: development and in vitro evaluation for transdermal delivery of a water insoluble drug," *J Pharm Sci* 103(11):3621-3630, 2014. (21 pages).

(56) References Cited

OTHER PUBLICATIONS

Ma et al., "A PZT Insulin Pump Integrated with a Silicon Micro Needle Array for Transdermal Drug Delivery," IEEE 56th Electronic Components & Technology Conference, 2006. (5 pages).
Matriano et al., "Macroflux R Microprojection Array Patch Technology: A New and Efficient Approach for Intracutaneous Immunization," *Pharmaceutical Research* 19(1):63-70, 2002.
McAllister et al., "Microfabricated needles for transdermal delivery of macromolecules and nanoparticles: Fabrication methods and transport studies," *PNAS* 100(24):13755-13760, 2003.
Meléndez et al., "Thermal Inkjet Application in the Preparation of Oral Dosage Forms: Dispensing of Prednisolone Solutions and Polymorphic Characterization by Solid-State Spectroscopic Techniques," *Journal of Pharmaceutical Sciences* 97(7):2619-2636, 2008.
Mengaud et al., "Expression in *Escherichia coli* and Sequence Analysis of the Listeriolysin O Determinant of *Listeria monocytogenes*," *Infection and Immunity* 56(4):766-772, 1988.
Miyano et al., "Sugar Micro Needles as Transdermic Drug Delivery System," *Biomedical Microdevices* 7(3):185-188, 2005.
Miyano et al., Hydrolytic Microneedles as Transdermal Drug Delivery System, IEEE the 14th International Conference on Solid-State Sensors, Actuators and Microsyystems, Lyon, France, pp. 355-358, Jun. 10-14, 2007.
Moore et al., "Introduction of Soluble Protein into the Class I Pathway of Antigen Processing and Presentation," *Cell* 54:777-785, 1988.
Mukerjee et al., "Microneedle array for transdermal biological fluid extraction and in situ analysis," *Sensors and Actuators A* 114:267-275, 2004.
Oh et al., "Demonstration of Dose-controlled Delivery by Dissolvable Micro-needle Arrays," 34th Annual Presented at CRS conference, Jun. 2007. (2 pages).
Oh et al., "Intradermal influenza vaccine delivery using skin-penetrating dissolveable vaccine microneedles," AAPS Annual Meeting and Exposition, 2006. (1 page).
Palmer et al., "Streptolysin O: A Proposed Model of Allosteric Interaction between a Pore-Forming Protein and Its Target Lipid Bilayer," *Biochemistry* 37:2378-2383, 1998.
Park et al., "Biodegradable polymer microneedles: Fabrication, mechanics and transdermal drug delivery," *Journal of Controlled Release* 104:51-66, 2005.
Park et al., "Polymer Microneedles for Controlled-Release Drug Delivery," *Pharmaceutical Research* 23(5):1008-1019, 2006.
Park et al., "Towards the silicon nanowire-based sensor for intracellular biochemical detection," *Biosensors and Bioelectronics* 22:2065-2070, 2007.
Portnoy et al., "Capacity of Listeriolysin O, Streptolysin O, and Perfringolysin O to Mediate Growth of *Bacillus subtilis* within Mammalian Cells," *Infection & Immunity* 60(7):2710-2717, 1992.
Radulescu et al., "Uniform Paclitaxel-Loaded Biodegradable Microspheres Manufactured by Ink-Jet Technology," *Proc., the Winter Symposium and 11th International Symposium on Recent Advantages in Drug-Delivery Systems, Controlled Release Society*, Salt Lake City, Utah, 2003, 5 pages.
Rossjohn et al., "Structure of a Cholestrol-Binding, Thiol-Activated Cytolysin and a Model of Its Membrane Form," *Cell* 89:685-692, 1997.
Sandler et al., "Inkjet Printing of Drug Substances and Use of Porous Substrates-Towards Individualized Dosing," *Journal of Pharmaceutical Sciences* 100(8):3386-3395, 2011.
Schulz et al., "Peptide-induced antiviral protection by cytotoxic T cells," *Proc. Natl. Acad. Sci. USA* 88:991-993, 1991.
Scoutaris et al., "ToF-SIMS analysis of chemical heterogenities in inkjet micro-array printed drug/polymer formulations," *J Mater Sci: Mater Med* 23:385-391, 2012.
Silver et al., "Viscoelastic Properties of Young and Old Human Dermis: A Proposed Molecular Mechanism for Elastic Energy Storage in Collagen and Elastin," *Journal of Applied Polymer Science* 86:1978-1985, 2002.

Stoeber et al., "Arrays of Hollow Out-of-Plane Microneedles for Drug Delivery," *Journal of Microelectromechanical Systems* 14(3):472-479, 2005.
Sullivan et al., "Minimally Invasive Protein Delivery with Rapidly Dissolving Polymer Microneedles," *Adv. Mater.* 20:933-938, 2008.
Tao et al., "A systematic study of dry etch process for profile control of silicon tips," *Microelectronic Engineering* 78-79:147-151, 2005.
Tarcha et al., "The Application of Ink-Jet Technology for the Coating and Loading of Drug-Eluting Stents," *Annals of Biomedical Engineering* 35(10):1791-1799, 2007.
Tsuchiya et al., "Development of Blood Extraction System for Health Monitoring System," *Biomedcal Microdevices* 7(4):347-353, 2005.
Tyagi et al., "Molecular Beacons: Probes that Fluoresce upon Hybridization," *Nature Biotechnology* 14:303-308, 1996.
Vigna et al., "Lentiviral vectors: excellent tools for experimental gene transfer and promising candidates for gene therapy," *The Journal of Gene Medicine*, 2:308-316, 2000.
Walther et al., "Viral Vectors for Gene Transfer," *Drugs* 60(2):249-271, 2000.
Wang et al., "Label-free hybridization detection of a single nucleotide mismatch by immobilization of molecular beacons on an agarose film," *Nucleic Acids Research* 30(12):e61, 2002. (9 pages).
Widera et al., "Effect of delivery parameters on immunization to ovalbumin following intracutaneous administration by a coated microneedle array patch system," *Vaccine* 24:1653-1664, 2006.
Wu et al., "Production of viral vectors for gene therapy applications," *Current Opinion in Biotechnology* 11:205-208, 2000.
Wu et al., "Solid free-form fabrication of drug delivery devices," *Journal of Controlled Release* 40:77-87, 1996.
Yuan et al., "Measuring microelastic properties of stratum corneum," *Colloids and Surfaces B: Biointerfaces* 48:6-12, 2006.
Zheng et al., "Multiplexed electrical detection of cancer markers with nanowire sensor Arrays," *Nature Biotechnology* 23(10):1294-1301, 2005.
Zhou et al., "Liposome-Mediated Cytoplasmic Delivery of Proteins: An Effective Means of Accessing the MHC Class I-Restricted Antigen Presentation Pathway," *Immunomethods* 4:229-235, 1994.
Australian Examination Report No. 1 dated Oct. 9, 2020 for Australian Application No. 2016333148, 5 pages.
Chinese Office Action dated Jan. 11, 2021 for Chinese Application No. 201880036675.8, 31 pages. (w/ machine translation).
Communication pursuant to Article 94(3) EPC, dated Jan. 19, 2021, for European Application No. 16 746 000.5, 4 pages.
Extended European Search Report dated Nov. 30, 2020 for European Application No. 18 77 6793, 10 pages.
Extended European Search Report dated Feb. 15, 2021 for European Application No. 18 81 6698, 8 pages.
Fernando et al., "Safety, tolerability, acceptability and immunogenicity of an influenza vaccine delivered to human skin by a novel high-density microprojection array patch (Nanopatch™)," *Vaccine* 36:3779-3788, 2018.
Fernando et al., "Influenza nucleoprotein DNA vaccination by a skin targeted, dry coated, densely packed microprojection array (Nanopatch) induces potent antibody and CD8+ T cell responses," *Journal of Controlled Release* 237:35-41, 2016.
International Search Report dated May 25, 2020 for International Application No. PCT/AU2020/050296, 6 pages.
Muller et al., "High-density microprojection array delivery to rat skin of low doses of trivalent inactivated poliovirus vaccine elicits potent neutralising antibody responses," *Scientific Reports* 7:12644, 2017. (10 pages).
Ng et al., "Potent response of QS-21 as a vaccine adjuvant in the skin when delivered with the Nanopatch, resulted in adjuvant dose sparing," *Scientific Reports* 6:29368, 2016. (12 pages).
Scoutaris et al., "Current Trends on Medical and Pharmaceutical Applications of Inkjet Printing Technology," *Pharm Res.* 33:1799-1816, 2016.
U.S. Appl. No. 14/351,499, filed Apr. 11, 2014, Delivery Device.
U.S. Appl. No. 15/401,950, filed Jan. 9, 2017, Delivery Device.
U.S. Appl. No. 15/849,134, filed Dec. 20, 2017, Method of Delivering Material or Stimulus to a Biological Subject.

(56) References Cited

OTHER PUBLICATIONS

U.S. Appl. No. 15/488,065, filed Aug. 1, 2017, Microprojection Array Applicator and Method.
U.S. Appl. No. 15/760,869, filed Mar. 16, 2018, Microprojection Arrays With Microprojections Having Large Surface Area Profiles.
U.S. Appl. No. 15/762,913, filed Mar. 23, 2018, Microprojection Arrays With Enhanced Skin Penetrating Properties and Methods Thereof.
U.S. Appl. No. 15/942,895, filed Apr. 2, 2018, Device and Method for Coating Surfaces.
U.S. Appl. No. 16/622,092, filed Dec. 12, 2019, Quality Control of Substrate Coatings.
U.S. Appl. No. 16/638,072, filed Feb. 10, 2020, Differential Coating of Microprojections and Microneedles on Arrays.
Chinese Office Action dated Feb. 14, 2022 for Chinese Application No. 201880036675.8, 12 pages.
Japanese Office Action dated Feb. 8, 2022 for Japanese Application No. 2019-554394, 6 pages.

* cited by examiner

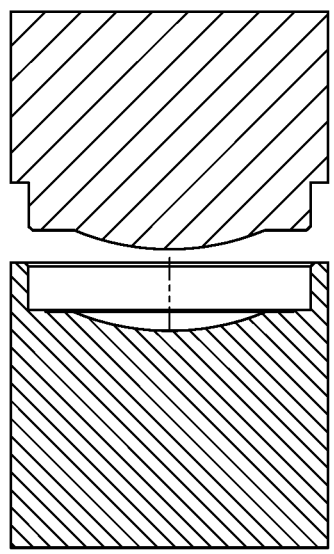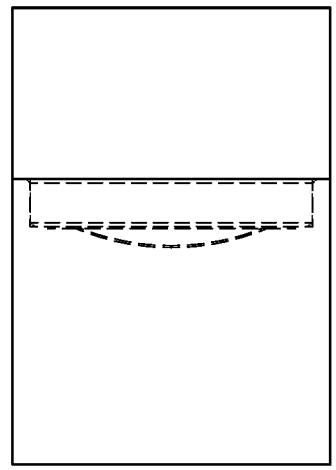
Fig. 2A　　　　　　　Fig. 2B
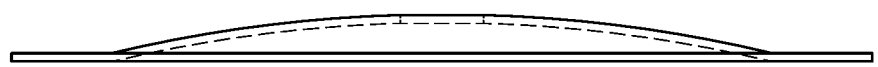
Fig. 3A
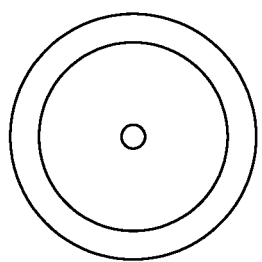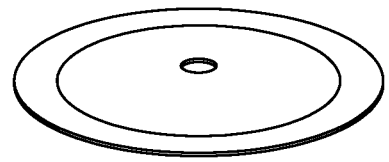
Fig. 3B　　　　　　　Fig. 3C

DETAIL A

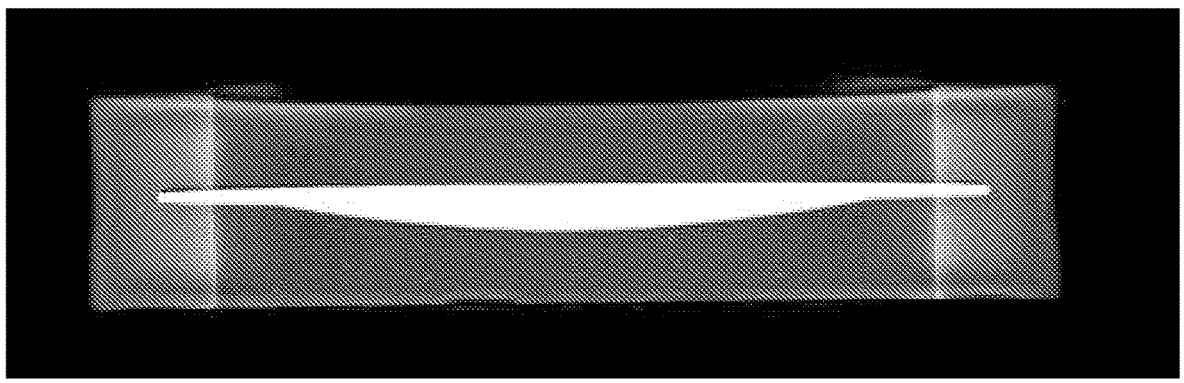
Fig. 8B
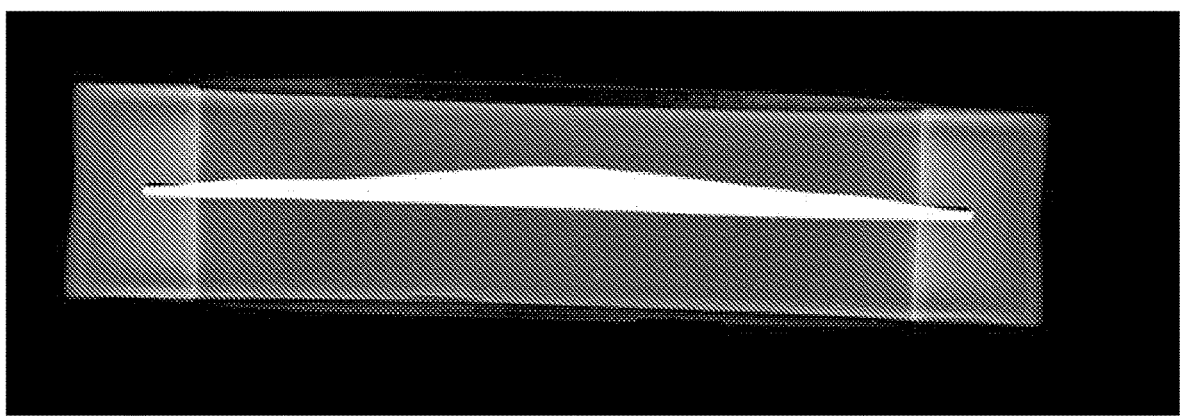
Fig. 8C
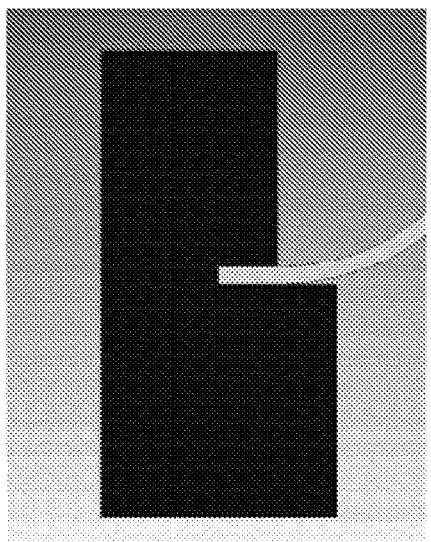 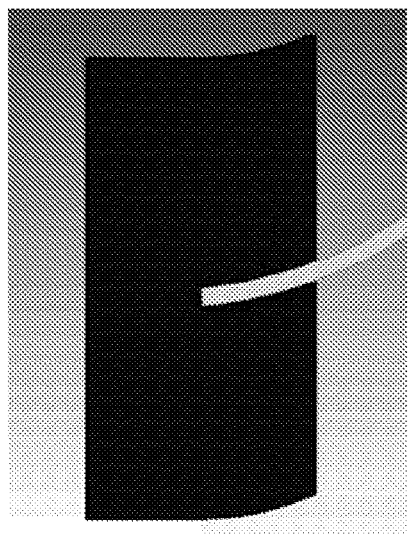
Fig. 9A    Fig. 9B

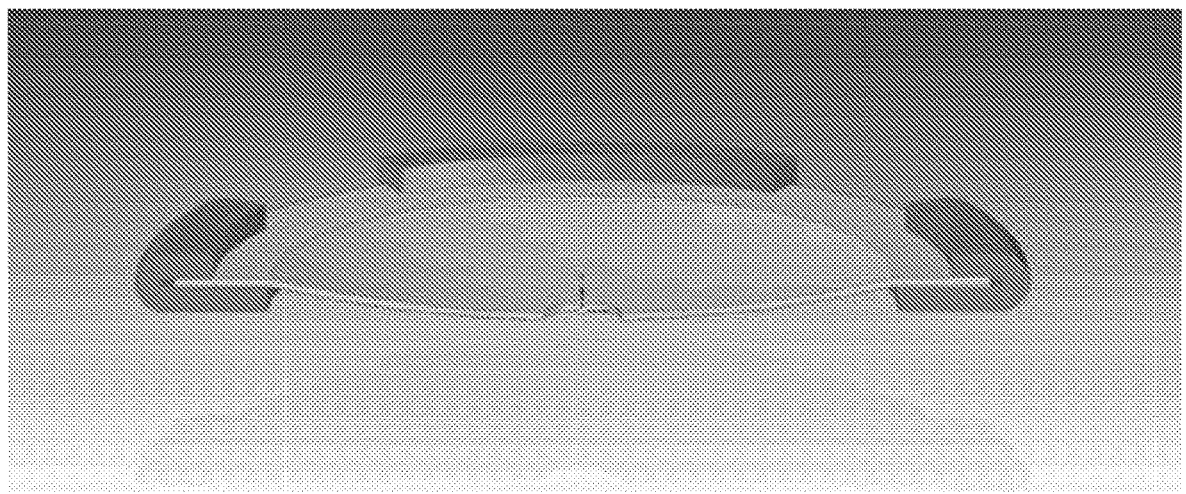
Fig. 13
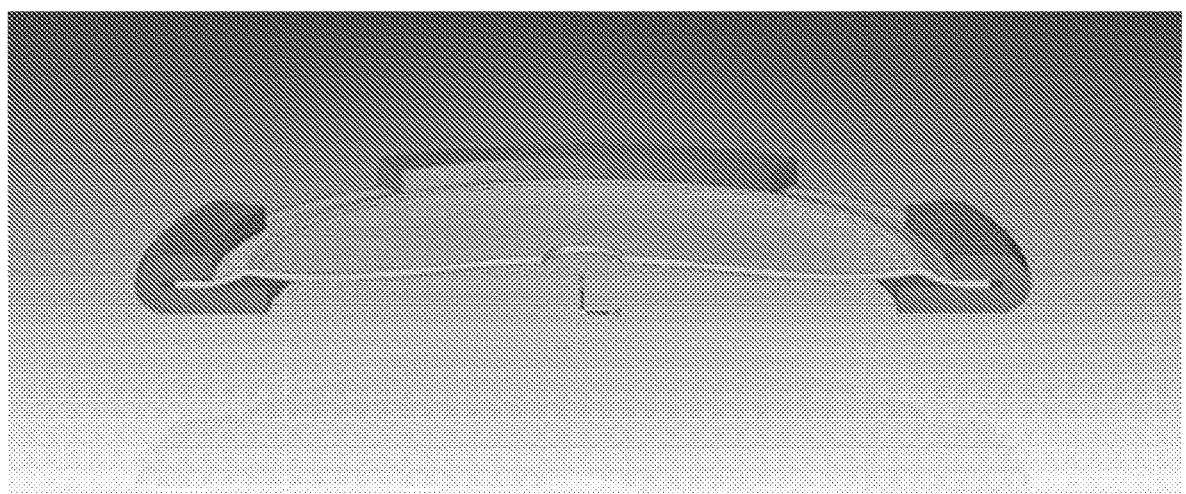
Fig. 14
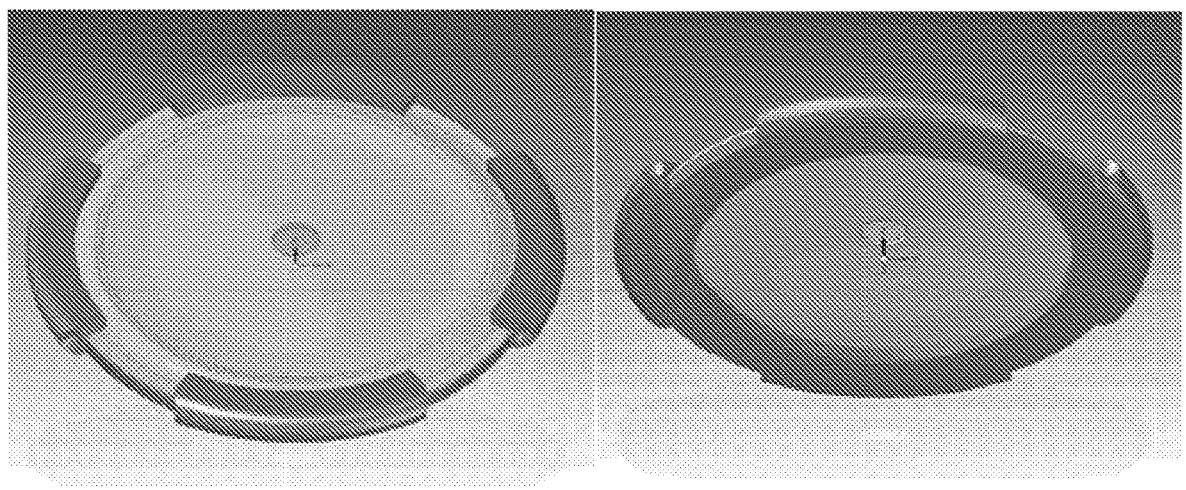
Fig. 15                    Fig. 16

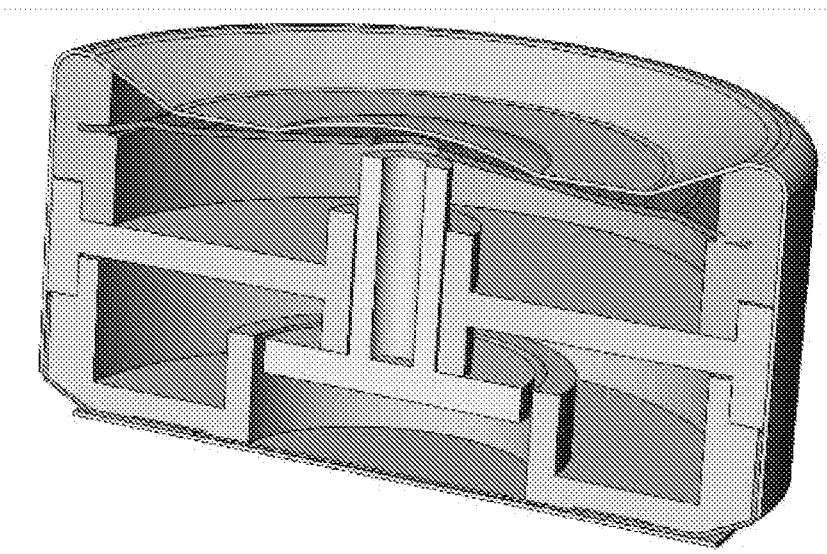
Fig. 26A
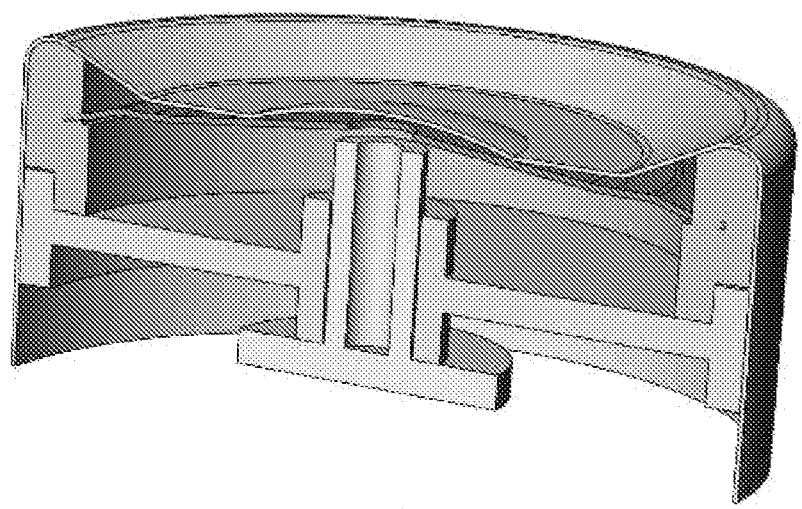
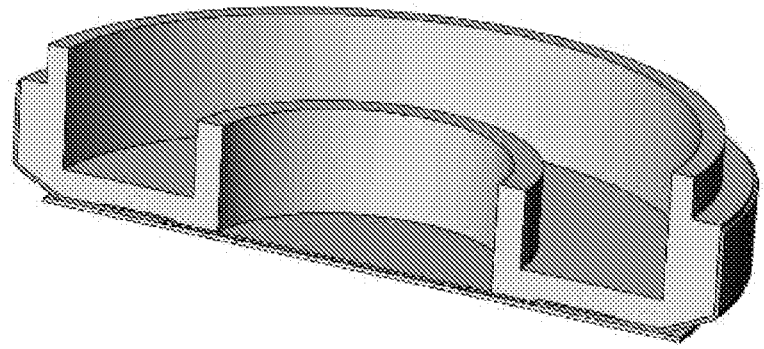
Fig. 26B

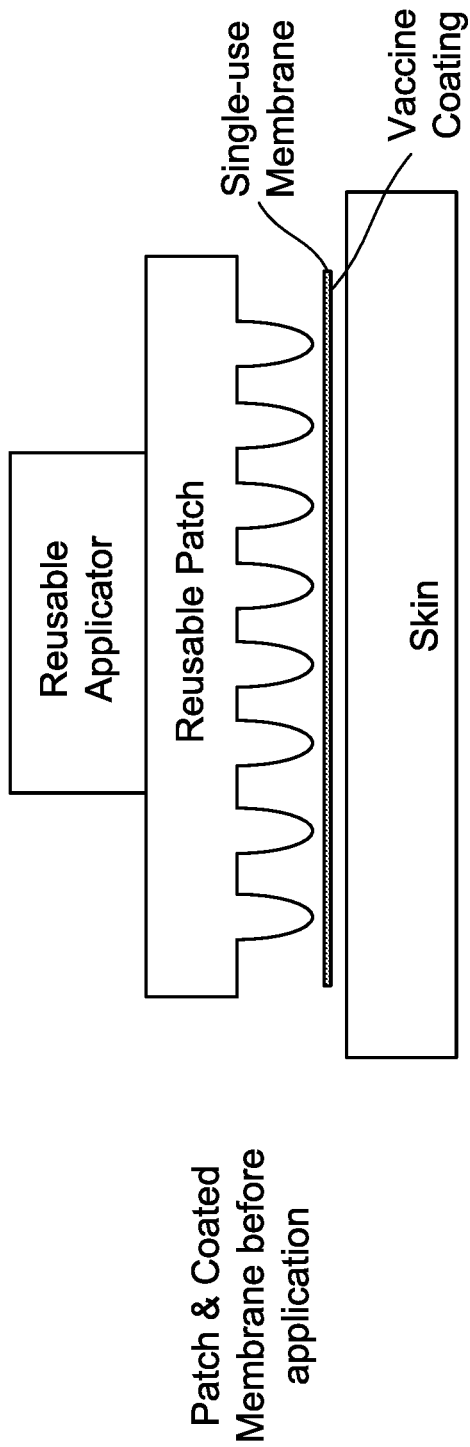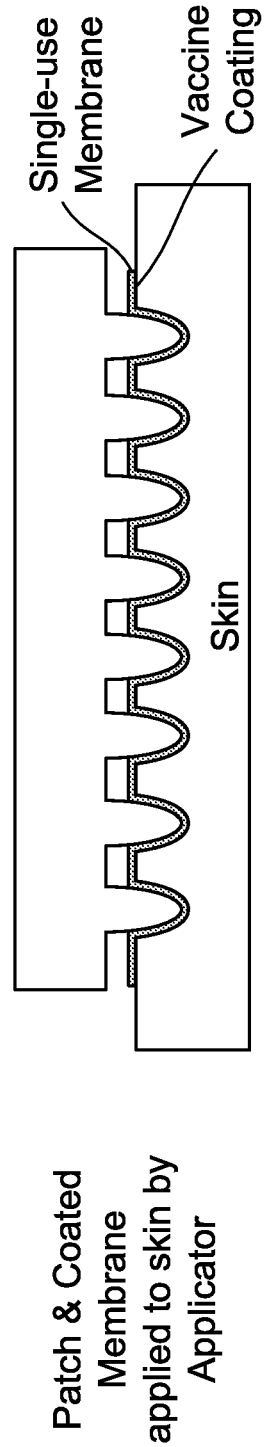
Fig. 31A Patch & Coated Membrane before application
Fig. 31B Patch & Coated Membrane applied to skin by Applicator

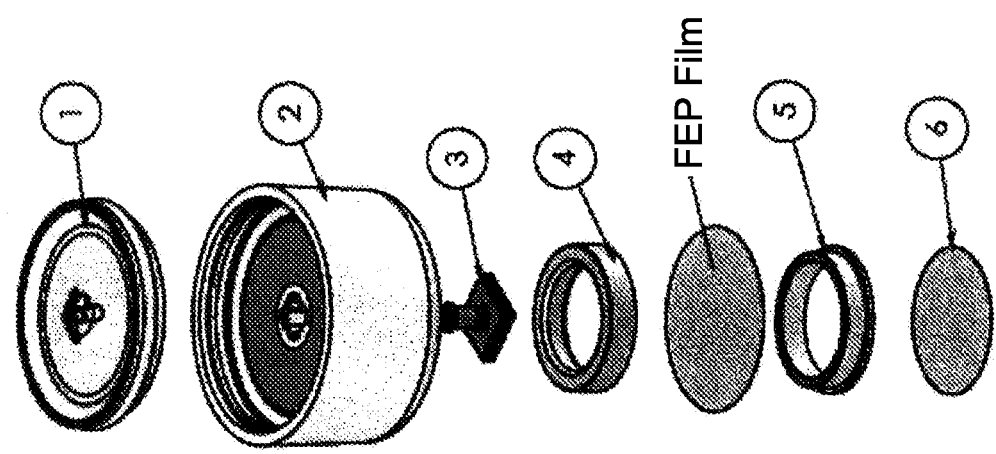
Fig. 32D
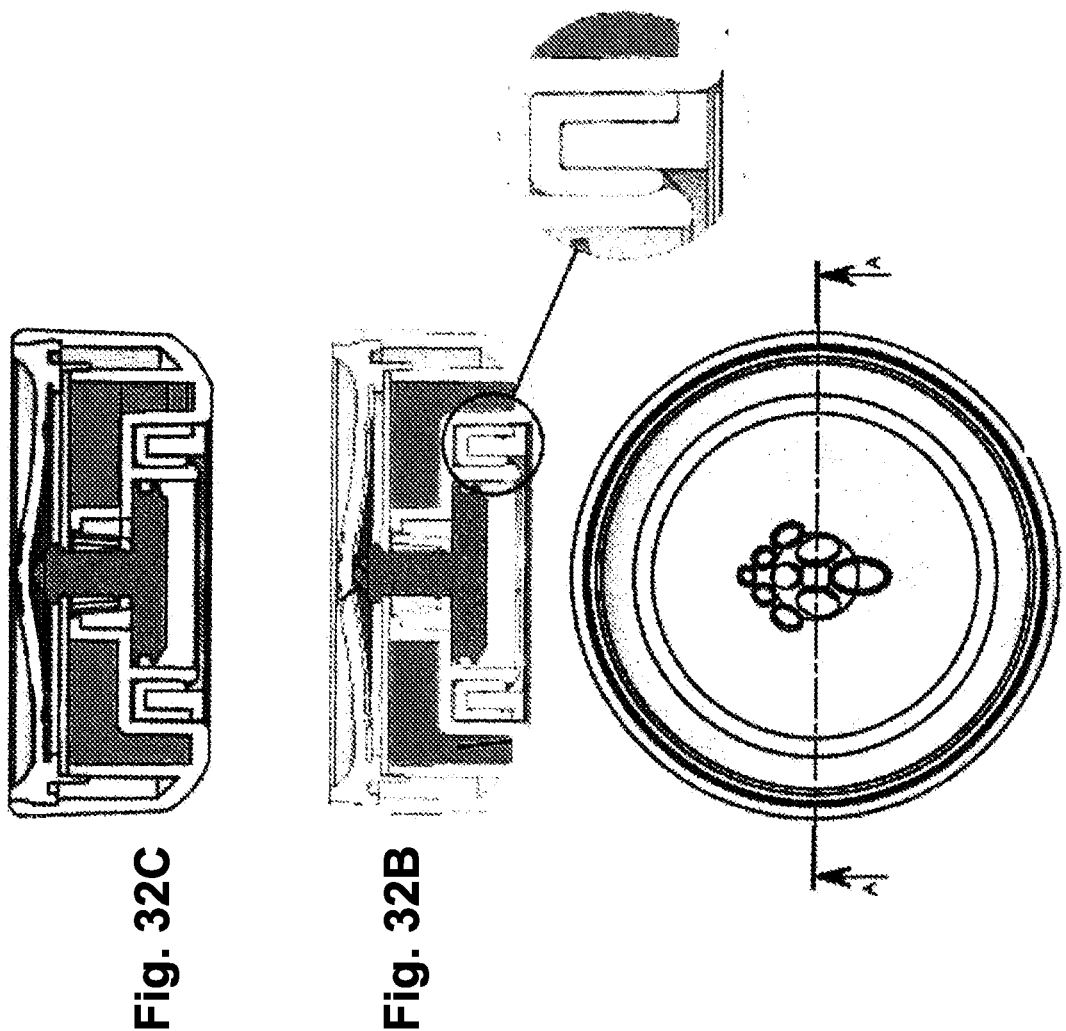
Fig. 32C
Fig. 32B
Fig. 32A

COMPACT HIGH MECHANICAL ENERGY STORAGE AND LOW TRIGGER FORCE ACTUATOR FOR THE DELIVERY OF MICROPROJECTION ARRAY PATCHES (MAP)

BACKGROUND OF THE INVENTION

The present invention relates to devices and methods for providing a triggering mechanism which lowers the trigger force to activate the trigger mechanism to a comfortable range of while still preserving or increasing the speed at which the triggering mechanism accelerates or imparts velocity to a device attached to the triggering mechanism. The present invention further relates to improved applicators for administering microprojection arrays to skin and methods of administering microprojection arrays. In particular, the present invention relates to compact stable self-contained mechanical energy storage for delivery of a medical device such as a microprojection array.

DESCRIPTION OF THE PRIOR ART

Recently, new methods of delivering drugs and other bioactive materials have been developed that are more convenient, provide superior efficacy or enhanced performance compared to intramuscular and intradermal injection. Intradermal injection is limited by cross-contamination through needle-stick injuries in health workers, injection phobia from a needle and syringe, and the inability for needle and syringe methodology to target key cells in the outer skin layers. There still exists a need for a light-weight and compact single use applicator that can be triggered easily by the user without discomfort to the user or patient, and/or enable the patient to use the applicator by self-administration, and/or target the more challenging geriatric and/or paediatric populations. The delivery of a device such as a medical device at high speed (e.g. a high density microprojection array) with minimal user trigger force and pressure on the patient, is highly desirable for the sake of public health.

US Patent Publication No. 2009/0198189 describes a device for applying a microneedle array to a skin surface in which the device is comprised of a base which defines a skin contacting plane, a microneedle array and a connecting member having a portion affixed to the base through a hinge and another portion affixed to the microneedle array.

US Patent Publication No. 2011/0276027 also describes an applicator for microneedles in which the applicator comprises an energy-storing element which upon application of force cause the compressed element to extend or transition from a first to a second configuration releasing the stored energy to deploy a member which is configured to hold a microneedle array.

U.S. Pat. No. 8,540,672 describes an applicator including a housing, a slidably disposed applicator plate, and a compression spring. The applicator plate is moveable between a retracted position and a deployed position, and has an engaging surface suitable for mashing up against a microneedle patch and pressing it against a skin surface. A docking system transfers the microneedle patch from a support to the applicator without requiring a user to handle the microneedle patch directly. Once mounted in the applicator, the microneedle patch is deployed against a skin surface of a patient for delivery of a desired agent via a microneedle array contained on the patch.

US Patent Publication No. 2008/0009811 describes an applicator capable of sensing a controlled distance from a skin surface and propelling a microneedle array across this distance and into the skin surface is disclosed. A method of applying a microneedle array to a skin surface by placing the microneedle array a predetermined distance away from the skin surface and propelling the microneedle array into the skin surface is disclosed.

WO 2014/058746 describes an applicator for applying a microneedle device to a skin surface. The applicator can include a microneedle device, a housing, and a connecting member. The connecting member can be configured to allow the microneedle device to move between: (i) a first position in which at least a portion of the microneedle device extends beyond the housing; and (ii) a second position in which the microneedle device is recessed within the housing when a threshold application force is applied to the microneedle device in a direction substantially perpendicular with respect to the microneedle device.

Despite the development of numerous devices for the application of microprojection and microneedle arrays there remain difficulties in devising a device and method for the arrays to overcome the natural elasticity of the skin and penetrating the skin to deliver the required drug dosage while maintaining comfort and ease of use for the patient. This is especially true when the microprojection arrays have a large number of densely packed microprojections in a small area array. The present invention provides devices and methods for projecting high density microprojection arrays (e.g. microprojection arrays having more than 1,000 projections/cm$^2$.

The prior art does not disclose an applicator for microprojection arrays or a method of application of microprojection arrays into the skin where the microprojection array can achieve high velocities thereby delivering the high density microprojection array to efficiently deliver a drug or vaccine such that the patient does not feel discomfort.

In view of the above, it would be desirable to provide for a light and compact single use applicator that can be triggered easily by the user without discomfort to the patient. It would be also desirable to provide applicators that enable the patient to use the applicator by self-administration or by administration by a second party. Furthermore, it would be desirable to provide for administration of drugs or vaccine to the more challenging geriatric and/or paediatric populations. It would also be desirable to enable the delivery of high density microprojection arrays at high speed with minimal user trigger force and pressure on the patient. The ease of administration, the reduction in patient discomfort, and the superior delivery of drugs and vaccines are highly desirable for the sake of public health.

The present invention seeks to provide for one or more of the desirable outcomes outlined above, or to at least provide a useful alternative to prior art solutions.

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

SUMMARY OF THE PRESENT INVENTION

The present invention relates to compact stable, self-contained mechanical energy storage devices for the administration of a Medical Device such as a microprojection array. The mechanisms and applicators of the present invention provide for actuation of medical devices at high speeds (e.g. 18-24 m/s) using a micro array patch (MAP) low mass (e.g. around 450 mg) while requiring a low trigger force (e.g. 10-25 N) from the user. The devices and methods of the present invention do not cause discomfort to the patient. Such mechanisms may be achieved by putting a high performance asymmetric bi-stable metal dome in a state of partial buckling, which is close to the dome's critical snap-through state, by encasing the dome while it is transiting from an unloaded to loaded state. By putting the dome in a state of partial buckling the dome's trigger force may be reduced such that triggering a device holding such a dome can be accomplished easily. The dome may be encased by forming a plastic over-moulding of the dome's outer rim, by ultrasound crimping plastic ribs over the dome's outer rim, by over moulding a plastic vault with a pattern of stiffening ribs on the dome, by using a folded metal casing, by using a ceramic casing, or by self-encasement of the dome by folding back the dome's edges on itself, or a combination of these approaches.

Metal discs or strips stamped in the shape of a dome or a strip of metal can exhibit bi-stable positions when specifically designed with pre-determined parameters with respect to stamping profile, height, thickness and steel properties. When a static or dynamic load is exerted on the dome, the dome will start buckling until a critical load is reached. Once the critical load is reached the dome suddenly accelerates and inverts its geometry ("snap through") without further loading.

An asymmetric bi-stable dome may be designed such that the force to load the dome in its energized state is higher than the force required for triggering the dome to return to its unloaded position. This asymmetry means the dome is able to store potential mechanical energy, which can be released in a highly transient timeframe due to a lower energy trigger.

The present invention relates to microprojection array applicators comprising such domes that provide application of microprojection arrays to the skin for the delivery of substances. The dome devices of the present invention are particularly useful for applying small area, high-density microprojection arrays having a large number of densely packed microprojections. In addition, the microprojection array applicators of the present invention are useful in the application of microprojection arrays that are of low mass and which may be projected into the skin by transiting a space between the applicator and the skin. In other words, the device and methods of the present invention provide applicators in which the low mass microprojection array is propelled through space prior to penetrating the skin. In one embodiment, the high density microprojection array has from about 1,000-20,000 projections/cm$^2$, and the array weighs around 450 mg and attains velocities of about 18-24 m/s prior to piercing the skin. Such high microprojection array velocities are normally considered unusual as the delivery of prior art microprojection arrays at high velocities often led to excessive bruising when applied to a patient.

The present invention also relates to methods of using the microprojection array applicators for applying arrays to the skin of a subject. The present invention relates to devices and methods for applying a microprojection arrays to retrieve biometric information for the purposes of diagnostics or for the collection of tissue of fluid samples.

The present invention provides a compact mechanism which enables the design of high density microprojection array applicators, able to provide high-velocities for low trigger forces and low impact on the patient, while containing its stored energy for an extended time.

The devices of the present invention can be used as a mechanical potential energy storage unit and actuator for a device, such as a medical device, for example a microprojection array. In this application the patch is accelerated or struck at high speed by the transiting dome, and propelled toward the patient skin. The attained velocity enables the patch to counter the natural elasticity of the skin and pierce the skin, and ultimately deliver the compounds coated on the microprojections of the array and into the skin tissues.

This mechanical potential energy storage unit and actuator (i.e. dome system) interfaces with the inner mechanism of the applicator (i.e. patch attach inner mechanism) which enables the assembly of the coated patch and its triggering upon contact with the transiting dome. The system provides guidance to the microprojection array while accelerating the array. The system provides a mechanism for preventing the release of the microprojection array during an unintentional triggering.

The dome system and patch attach inner mechanism are lodged in the applicator shell which acts as a sterile and low water ingress barrier. The bottom shell has a closure system, such as a foil lid that may be opened or removed before application of the microprojection array. The bottom shell can incorporate a skin contact membrane that is pierced by the MAP. The top shell has a flexible top that when collapsed actuates the dome system which in turn accelerates the patch toward the patient's skin.

In one broad form, an aspect of the present invention seeks to provide a device comprising a dome in an encasement.

In one embodiment, the dome is preloaded with a force.

In one embodiment, the dome has a flattened outer edge.

In one embodiment, the preloaded dome is made of steel and the encasement comprises a folded metal ring, wherein the folded metal ring envelopes the flattened outer edge of the dome.

In one embodiment, the folder metal ring continuously envelopes the flattened outer edge of the dome.

In one embodiment, the folded metal ring has one or more tabs, wherein the tabs fold over the flattened outer edge of the dome.

In one embodiment, the number of tabs is from 2 to 10.

In one embodiment, the folded metal ring envelopes the edge of the dome by bending the tab(s) and the folding the tab(s) onto the edge of the dome.

In one embodiment, the tab(s) are folded in a press tool.

In one embodiment, a force required to trigger the preloaded dome is from about 5 to about 50 newtons.

In one embodiment, the preloaded dome has been loaded with a force of from about 100 to about 400 newtons.

In one embodiment, a ratio of a triggering force required to trigger the preloaded dome and a loading force used to load the preloaded dome is from about 1:50 to about 1:5.

In one embodiment, an edge of the dome has been flattened in comparison to an interior of the dome.

In one embodiment, the preloaded dome has an upper surface and a lower surface, wherein the upper surface has an upper edge and the lower surface has a lower edge and the encasement comprises a first metal ring and a second metal ring, wherein the first metal ring is secured to the upper edge of the upper surface of the dome and the second metal ring is secured to the lower edge of the lower surface of the dome.

In one embodiment, the first and second metal rings are secured to the edges of the dome by screws that connect the first metal ring and the second metal ring by penetrating the dome edge.

In one embodiment, the first and second metal rings are secured to the edges of the dome by welds.

In one embodiment, a force required to trigger the preloaded dome is from about 5 to about 50 newtons.

In one embodiment, the preloaded dome has been loaded with a force of from about 100 to about 400 newtons.

In one embodiment, a ratio of a triggering force required to trigger the preloaded dome and a loading force used to load the preloaded dome is from about 1:50 to about 1:5.

In another broad form, the present invention seeks to provide a device for accelerating a projectile comprising an encased dome encased in a casing.

In one embodiment, the dome is encased in a casing made from the group consisting of: plastic, ceramic, aluminium metals, steel, glass, carbon fibers or combinations thereof.

In one embodiment, the casing is made of plastic.

In one embodiment, the plastic is selected from the group consisting of: 15%-50% glass reinforced nylon; and 40% glass reinforced polyphenylene sulphide.

In one embodiment, the dome is encased by a method selected from the group consisting of: by over-moulding of the dome outer rim with plastic, by over moulding a plastic vault with a pattern of stiffening ribs on the dome, by using a folded metal casing, by using a ceramic casing, or by self-encasement of the dome by folding back the dome's edges on itself, or a combination of these approaches.

In one embodiment, the dome is made of austenitic stainless steel.

In one embodiment, the steel is approximately 0.3 mm thick and approximately 31.1 mm in diameter, and wherein there is an approximately 3.0 mm diameter hole in the centre of the dome.

In one embodiment, the steel has a tensile strength of approximately 2050 MPa and a 0.2% offset yield strength of approximately 1975 MPa.

In one embodiment, the device further comprises a plastic vault.

In another broad form, the present inventions seeks to provide a method of accelerating a projectile comprising: encasing a dome in a casing; pre-loading the dome of with a loading force; triggering the pre-loaded dome with a triggering force such that the dome is triggered; and accelerating the projectile.

In one embodiment, the projectile is a microprojection array.

In one embodiment, the ratio of the triggering force and loading force is from about 1:50 to about 1:5.

In one embodiment, the microprojection array attains a velocity of greater than about 15 m/s.

In one embodiment, the microprojection array attains a velocity of greater than about 25 m/s.

In one embodiment, the microprojection array attains a velocity of from about 15 to about 50 m/s.

In one embodiment, the microprojection array attains a velocity of from about 20 to about 26 m/s.

In one embodiment, the microprojection array has from about 1000 to 20000 microprojections.

In one embodiment, the microprojection array has from about 2000 to 10000 microprojections.

In one embodiment, the microprojection array has from about 3000 to 6000 microprojections.

In one embodiment, the microprojection array has a density of from about 1000 to about 20000 microprojections per $mm^2$.

In one embodiment, the microprojection array has a density of from about 1000 to about 20000 microprojections per $mm^2$.

In one embodiment, the triggering force is from about 10 to about 100 newtons.

In one embodiment, the triggering force is from about 10 to about 50 newtons.

In one embodiment, the pre-loading force is from about 100 to about 400 newtons.

In one embodiment, the pre-loading force is from about 150 to about 350 newtons.

In another broad form, the present invention seeks to provide a device for applying a microprojection array to a skin surface comprising: a housing having a base defining an opening that in use is provided in contact with the skin surface; a spigot movably mounted within the housing wherein the spigot supports the microprojection array in use; a trigger; a skin contact membrane provided in the opening; and a biasing member supported by the housing and movable from a first position to a second position upon activation of the trigger, wherein the biasing member urges the microprojection array through the skin contact membrane and into engagement with the skin surface through the opening.

In one embodiment, the biasing member is an over-moulded dome.

In one embodiment, the overmoulded dome is encased in a casing.

In one embodiment, the dome is made of steel and the casing comprises a foldable metal ring wherein the foldable metal ring envelopes an edge of the dome.

In one embodiment, the foldable metal ring has one or more tabs.

In one embodiment, the number of tabs is from 2 to 10.

In one embodiment, the foldable metal ring envelopes the edge of the dome by bending the tab(s) and the folding the tab(s) onto the edge of the dome.

In one embodiment, the tab(s) are folded in a press tool.

In one embodiment, a force required to trigger the dome is from about 5 to about 50 newtons.

In one embodiment, the dome has been preloaded with a force of from about 100 to about 400 newtons.

In one embodiment, a ratio of a triggering force required to trigger the dome and a loading force used to preload the dome is from about 1:50 to about 1:5.

In one embodiment, an edge of the dome has been flattened in comparison to an interior of the dome.

In one embodiment, the dome has an upper surface and a lower surface, wherein the upper surface has an upper edge and the lower surface has a lower edge and the casing comprises a first metal ring and a second metal ring, wherein the first metal ring is secured to the upper edge of the upper surface of the dome and the second metal ring is secured to the lower edge of the lower surface of the dome.

In one embodiment, the first and second metal rings are secured to the edges of the dome by screws that connect the first metal ring and the second metal ring by penetrating the dome edge.

In one embodiment, the first and second metal rings are secured to the edges of the dome by welds.

In one embodiment, the dome is made of austenitic stainless steel.

In one embodiment, the dome is encased in a casing made from the group consisting of: plastic, ceramic, aluminium metals, steel, glass, carbon fibers or combinations thereof.

In one embodiment, the casing is made of plastic.

In one embodiment, the dome is encased by a method selected from the group consisting of: by plastic over-moulding of the dome outer rim, by over moulding a plastic vault with a pattern of stiffening ribs on the dome, by using a folded metal casing, by using a ceramic casing, or by self-encasement of the dome by folding back the dome's edges on itself, or a combination of these approaches.

In another broad form, the present invention seeks to provide a device for applying a microprojection array to a skin surface comprising: a housing having an upper portion and a lower portion and having an internal face and an external face, wherein the external face has a flexible section that when collapsed actuates the device; a spigot having a proximal and distal end, wherein the proximal end interfaces with the internal face of the housing such that when the flexible section of the external face of the housing is collapsed the patch guide is forced downward; an encased dome having an opening through which the patch guide passes, and wherein the dome ring is activated by the patch guide; a microprojection array that is contacted by the encased dome when the dome is activated; a skin contact membrane; and a skin contact applicator base that attaches to the housing.

In one embodiment, the dome is made of steel and the encasement comprises a foldable metal ring, wherein the foldable metal ring envelopes an edge of the dome.

In one embodiment, the foldable metal ring has one or more tabs.

In one embodiment, the number of tabs is from 2 to 10.

In one embodiment, the foldable metal ring envelopes the edge of the dome by bending the tab(s) and the folding the tab(s) onto the edge of the dome.

In one embodiment, the tab(s) are folded in a press tool.

In one embodiment, a force required to trigger the dome is from about 5 to about 50 newtons.

In one embodiment, the preloaded dome has been loaded with a force of from about 100 to about 400 newtons.

In one embodiment, a ratio of a triggering force required to trigger the dome and a loading force used to load the dome is from about 1:50 to about 1:5.

In one embodiment, an edge of the dome has been flattened in comparison to an interior of the dome.

In one embodiment, the preloaded dome has an upper surface and a lower surface wherein the upper surface has an upper edge and the lower surface has a lower edge and the encasement comprises a first metal ring and a second metal ring wherein the first metal ring is secured to the upper edge of the upper surface of the dome and the second metal ring is secured to the lower edge of the lower surface of the dome.

In one embodiment, the first and second metal rings are secured to the edges of the dome by screws that connect the first metal ring and the second metal ring by penetrating the dome edge.

In one embodiment, the first and second metal rings are secured to the edges of the dome by welds.

In one embodiment, the flexible section of the housing is in the upper portion of the housing.

In one embodiment, the flexible section of the housing is in the lower portion of the housing.

In one embodiment, the flexible section is off-center.

In one embodiment, the device further comprises a membrane support which interfaces with the skin contact applicator base and holds the skin contact membrane in place.

In one embodiment, the device further comprises a cover to at least partially cover the skin contact applicator base.

In one embodiment, the cover keeps the device sterile and prevents fluids from getting in the device.

In one embodiment, the cover is a foil seal.

In one embodiment, the device further comprises a stopping mechanism to prevent the microprojection array from flying out of the device if the device is unintentionally triggered.

In one embodiment, the microprojection array remains attached to the device and can be removed from the skin when device is pulled away from the skin.

In one embodiment, the stopping mechanism is part of the patch guide.

In one embodiment, the microprojection array is a high density array.

In one embodiment, the first external housing has a finger detent for actuating the device.

In one embodiment, the microprojection array has a density of from 5000 to 20,000 projections per $cm^2$.

In one embodiment, the dome achieves a velocity of between about 20 to about 50 meters/second when activated.

In one embodiment, the device is a single use device.

In one embodiment, the device is a disposable device.

In one embodiment, the disposal of the device reduces contaminated waste incineration by using materials that emit a minimum of toxins upon incineration and reduce volume of packaging and device.

In one embodiment, the membrane is made of a polymer film.

In one embodiment, the polymer film is from about 2 to about 20 μm thick.

In one embodiment, the polymer film includes a substance either coated onto the polymer film or within the polymer film.

In one embodiment, the substance has a therapeutic or prophylactic effect.

In one embodiment, the substance is a therapeutic agent to assist in wound healing.

In one embodiment, the substance is a desiccant.

In one embodiment, a desiccant is included inside the device.

In one embodiment, a desiccant is included in the housing and/or molded parts of the device.

In one embodiment, the device also removes the microprojection array from the skin after the microprojection array penetrates the skin.

In one embodiment, the microprojection array can be releasably detached from the device.

In one embodiment, the microprojection array has a mass from about 0.1 grams to about 0.5 grams.

In one embodiment, the microprojection array has a mass of about 0.3 grams.

In one embodiment, the internal portion of the device is sterile.

In one embodiment, the housing forms a sealed sterile barrier and once used the device can be disassembled without contaminated features contacting the user.

In another broad form, the present invention seeks to provide a device comprising a dome which has a flattened outer edge encased in a plastic encasement, wherein the outer edge of the dome is encased in the plastic encasement by ultrasound crimping of plastic ribs over the dome's outer rim.

In one embodiment, a force required to trigger the dome is from about 5 to about 50 newtons.

In one embodiment, the dome has been preloaded with a force of from about 100 to about 400 newtons.

In one embodiment, a ratio of a triggering force required to trigger the dome and a loading force used to preload the dome is from about 1:50 to about 1:5.

In another broad form, the present invention seeks to provide a device for applying a microprojection array to the skin of a mammal, the device comprising a housing and a collapsible trigger operably linked to a pre-loaded dome, wherein the pre-loaded dome is encased in the housing such that when the trigger is collapsed the dome transitions from a loaded position to an unloaded position, thereby propelling the microprojection array into the mammal's skin.

In one embodiment, the dome is encased in the housing by ultrasound crimping.

In one embodiment, the dome has a flattened outer edge

In one embodiment, the ultrasound crimping provides that the housing encases the flattened outer edge of the dome.

In one embodiment, the housing that encases the flattened outer edge of the dome encompasses a portion of the flattened edge of the dome.

In one embodiment, the portion of the housing that encases the flattened outer edge of the dome comprises one or more ribs protruding from the housing.

In one embodiment, the device further comprises a microprojection array.

In one embodiment, the microprojection array is embedded in the dome.

In one embodiment, the microprojection array is not embedded in the dome.

It will be appreciated that the broad forms of the invention and their respective features can be used in conjunction, interchangeably and/or independently, and reference to separate broad forms is not intended to be limiting.

BRIEF DESCRIPTION OF THE DRAWINGS

Various examples and embodiments of the present invention will now be described with reference to the accompanying drawings, in which: —

FIGS. 2A and 2B are schematic drawings of one embodiment of the device used to pre-load the dome.

FIGS. 3A to 3C are schematic drawings of one embodiment of the dome of the present invention.

FIG. 8B is an x-ray of an over moulded dome in a non-primed position; and FIG. 8C is an x-ray of an over moulded dome in a primed position.

FIG. 9A is a drawing of one embodiment of a stiff encasing design; and FIG. 9B is a drawing of one embodiment of a flexible encasing design.

FIG. 13 is a representation of one embodiment of a foldable metal ring encasing a dome (unloaded cross section view).

FIG. 14 is a representation of one embodiment of a foldable metal ring encasing a dome (loaded cross section view).

FIG. 15 is a representation of one embodiment of a foldable metal ring encasing a dome (loaded top view).

FIG. 16 is a representation of another embodiment of a foldable metal ring encasing a dome (loaded bottom view).

FIGS. 26A and 26B are cross-sectional representations of applicator shells acting as a sterile and low water ingress barrier, leading to the incorporation of the primary packing into the applicator, due to the small inner volume driven by the compact dome system.

FIGS. 28A and 27B are cross-sectional representations of applicator shells acting as a sterile and low water ingress barrier, leading to the incorporation of the primary packing into the applicator, due to the small inner volume driven by the compact dome system.

FIG. 31A is a depiction of the applicator, patch and coated membrane prior to delivery of the coating to the skin; and FIG. 31B is a depiction of the applicator, patch and coated membrane after delivery of the coating to the skin.

FIGS. 32A to 32D are schematic drawings of one embodiment where materials could be placed between the membrane (FEP film) and the foil cover (6) that could provide relief from erythema, oedema and skin discoloration.

DETAILED DESCRIPTION OF THE PREFERRED EMBODIMENTS

The present invention relates to compact stable, self-contained mechanical energy storage devices for the administration of a Medical Device such as a microprojection array. The mechanisms and applicators of the present invention provide for actuation of medical devices at high speeds (e.g. 18-24 m/s) using a micro array patch (MAP) low mass (e.g. around 450 mg) while requiring a low trigger force (e.g. 10-25 N) from the user. The devices and methods of the present invention do not cause discomfort to the patient when the applicator applies the device to the patient.

Figure 1:
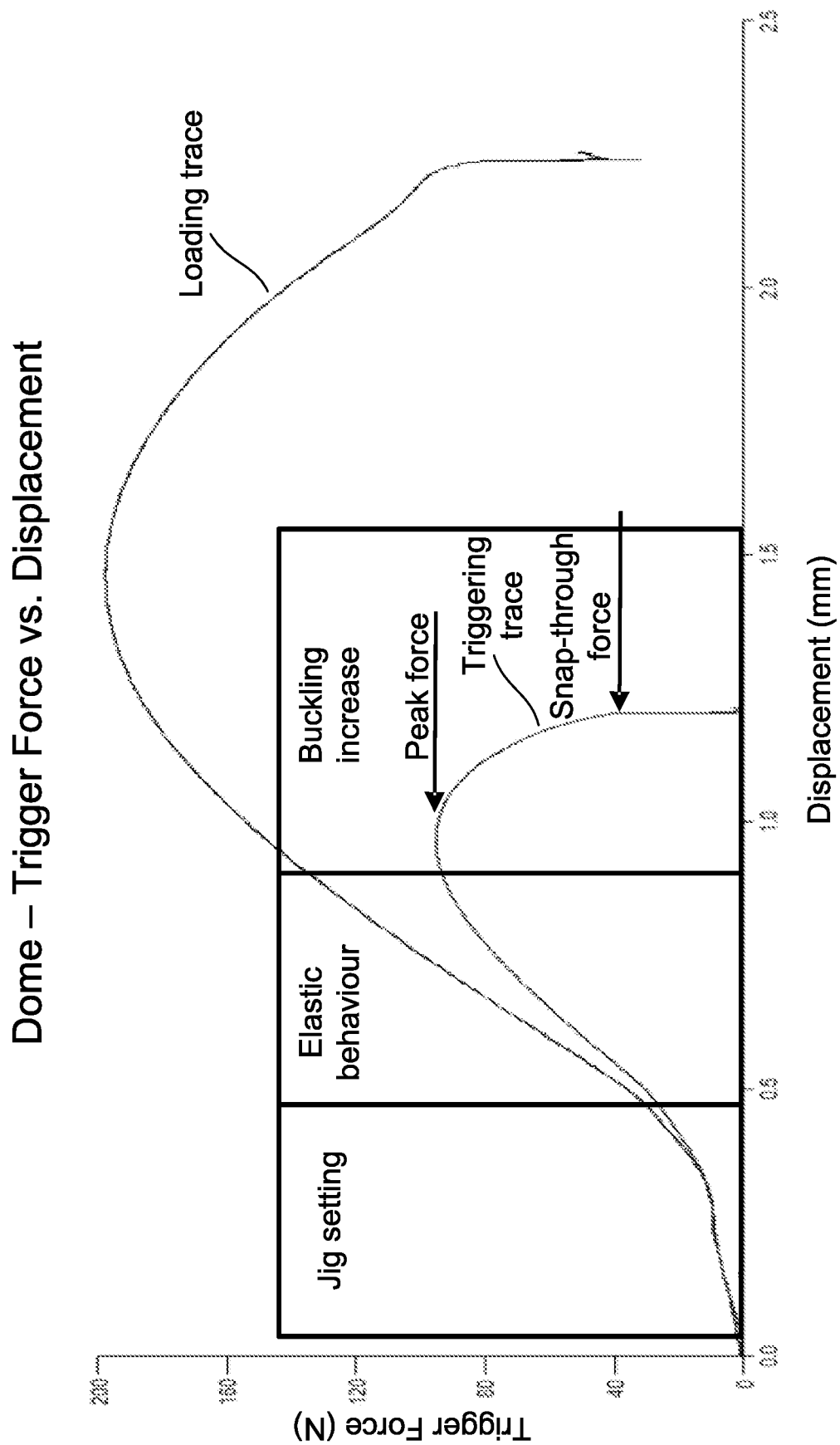
FIG. 1 is a plot of trigger force versus displacement for a high performance dome.

High performance asymmetric bi-stable domes which provide high speeds in the [18-24] m/s range have a loading force in the range of 200-300 Newtons and a trigger force around 100 Newtons (i.e. an approximate weight of 10 kg at standard gravity acceleration), (See FIG. 1 for a plot of trigger force versus displacement for a high performance dome). Trigger force may result in a discomfort both for the user who needs to provide the large device trigger force and the patient who feels the large device pressure on the skin when triggering.

The devices and methods of the present invention provide a mechanism to lower the force when triggering the application device to a comfortable range of approximately 10-25 Newtons, while preserving or increasing the dome's velocity, such that the dome may accelerate a 450 mg projectile (such as a microprojection array) to a velocity of approximately 18-24 m/s. The domes of the present invention are induced into a partially buckled state by encasing the dome in the applicator, such as by encasing the dome in an over-moulding. The dome may be encased by forming a plastic over-moulding of the dome's outer rim, by ultrasound crimping plastic ribs over the dome's outer rim, by over moulding a plastic vault with a pattern of stiffening ribs on the dome, by using a folded metal casing, by using a ceramic casing, or by self-encasement of the dome by folding back the dome's edges on itself, or a combination of these approaches.

The devices of the present invention must have the dome correctly integrated into the device, applicator or housing so that the energy release generated by triggering the dome is funnelled toward the patch and not lost in random fluctuations. A dome without integration into the device without any encasement (continuous or tabbed metal ring or ultrasound crimping or other methods described herein) will "jump" in the device and as a consequence the acceleration of the patch will be adversely impacted. An efficient coupling of the dome to the patch results in efficient acceleration of the patch and a successful application of the patch to the skin.

In one embodiment the dome may be made from an austenitic stainless steel strip (Sandvik 11R51, 0.3 mm thick), laser cut in an approximately 31.1 mm diameter disc, with a centred, approximately 3.0 mm diameter hole. This particular type of steel has excellent spring properties, with a high tensile strength (2050 MPa), and high yield strength (0.2% offset yield strength of 1975 MPa). Other embodiments of the domes include diameters which range from about 5 to 80 mm, or from about 5 to 70 mm or from about 5 to 60 mm or from about 5 to 50 mm or from about 5 to 40 mm or from about 5 to 30 mm or from about 5 to about 20 mm or from about 10 to 80 mm, or from about 10 to 70 mm or from about 10 to 60 mm or from about 10 to 50 mm or from about 10 to 40 mm or from about 10 to 30 mm or from about 10 to about 20 mm or from about 20 to 80 mm, or from about 20 to 70 mm or from about 20 to 60 mm or from about 20 to 50 mm or from about 20 to 40 mm or from about 20 to 30 mm or from about 30 to 80 mm, or from about 30 to 70 mm or from about 30 to 60 mm or from about 30 to 50 mm or from about 30 to 40 mm or from about 40 to 80 mm, or from about 40 to 70 mm or from about 40 to 60 mm or from about 40 to 50 mm or from about 50 to 80 mm, or from about 50 to 70 mm or from about 50 to 60 mm. The thickness of the dome may be from about 0.1 to 2 mm or from about 0.1 to 1.5 mm or from about 0.1 to 1.0 mm or from about 0.1 to 0.5 mm or from about 0.25 to 2 mm or from about 0.25 to 1.5 mm or from about 0.25 to 1.0 mm or from about 0.25 to 0.5 mm or from about 0.5 to 2 mm or from about 0.5 to 1.5 mm or from about 0.5 to 1.0 mm or from about 0.75 to 2 mm or from about 0.75 to 1.5 mm or from about 0.75 to 1.0 mm or from about 1.0 to 2 mm or from about 1.0 to 1.5 mm or from about 1.5 to 2.0 mm. The hole diameter in the dome may be from about 0% to 70% of the dome or from about 0% to 60% of the dome or from about 0% to 50% of the dome or from about 0% to 40% of the dome or from about 0% to 30% of the dome or from about 0% to 20% of the dome or from about 0% to 10% of the dome or from about 10% to 70% of the dome or from about 10% to 60% of the dome or from about 10% to 50% of the dome or from about 10% to 40% of the dome or from about 10% to 30% of the dome or from about 10% to 20% of the dome or from about 20% to 70% of the dome or from about 20% to 60% of the dome or from about 20% to 50% of the dome or from about 20% to 40% of the dome or from about 20% to 30% of the dome or from about 30% to 70% of the dome or from about 30% to 60% of the dome or from about 30% to 50% of the dome or from about 30% to 40% of the dome or from about 40% to 70% of the dome or from about 40% to 60% of the dome or from about 40% to 50% of the dome or from about 50% to 70% of the dome or from about 50% to 60%. The yield strength of the dome may be from about 400 to 3500 MPa, or from about 400 to 3000 Mpa, or from about 400 to 2500 MPa or from about 400 to 2000 Mpa, or from about 400 to 1500 MPa, or from about 400 to 1000 MPa, or from about 400 to 500 Mpa, or from about 1000 to 3500 MPa or from about 1000 to 3000 Mpa, or from about 1000 to 2500 MPa or from about 1000 to 2000 Mpa, or from about 1000 to 1500 MPa or from about 1500 to 3500 Mpa, or from about 1500 to 3000 MPa, or from about 1500 to 2500 Mpa, or from about 1500 to 2000 MPa, or from about 2000 to 3500 MPa or from about 2000 to 3000 MPa or from about 2000 to 2500 or from about 2500 to 3500 or from about 2500 to about 3000. The tensile strength of the dome may be from about 250 to 2400 MPa, or from about 250 to 2000 Mpa, or from about 250 to 1500 MPa or from about 250 to 1000 Mpa, or from about 250 to 500 MPa, or from about 500 to 2400 MPa, or from about 500 to 2000 Mpa, or from about 500 to 1500 MPa or from about 500 to 1000 Mpa, or from about 750 to 2400 MPa or from about 750 to 2000 Mpa, or from about 750 to 1500 MPa or from about 750 to 1000 Mpa, or from about 1000 to 2400 MPa, or from about 1000 to 2000 Mpa, or from about 1000 to 1500 MPa, or from about 1500 to 2400 MPa or from about 1500 to 200 MPa.

In one embodiment the dome may be plastically deformed under 1 to 5 tons of pressure using a hydraulic press, into a spherical cap, using the specific tool T6.2 (See FIGS. 2A and 2B) which can have an anti-wrinkling pressure pad added. This tool profile results in a high performance asymmetric bi-stable dome spring with a circumferentially flat lip which is 3.6 mm wide and a domed central region, with an approximately 3 mm centre hole at the apex of the central region (See FIGS. 3A to 3B). The transition radius between the lip and the dome central region is a fold line. A natural slight second curvature appears in the dome due to the anisotropy induced by the grain structure of the steel.

Figure 4C:
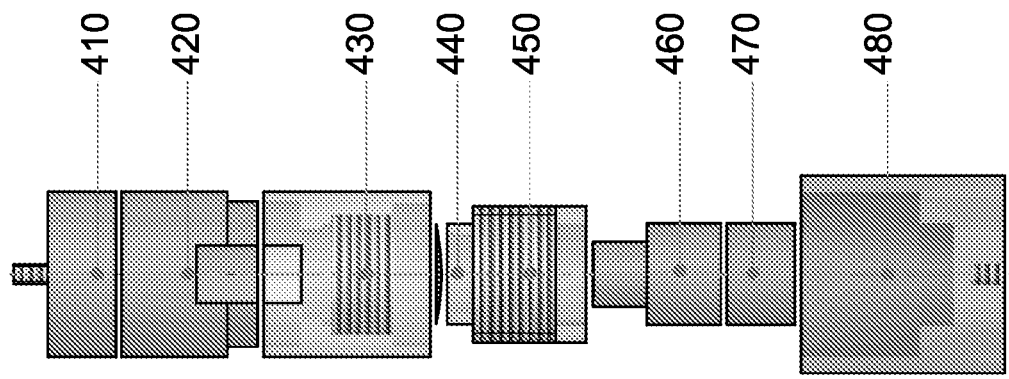
FIG. 4A to 4C are schematic drawings of one embodiment of a test jig.
Figure 4B:
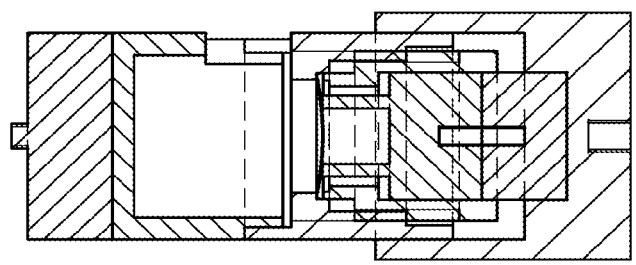
Figure 4A:
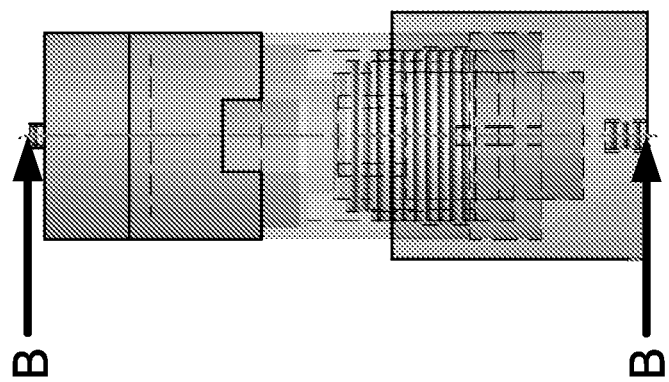
Figure 5B:
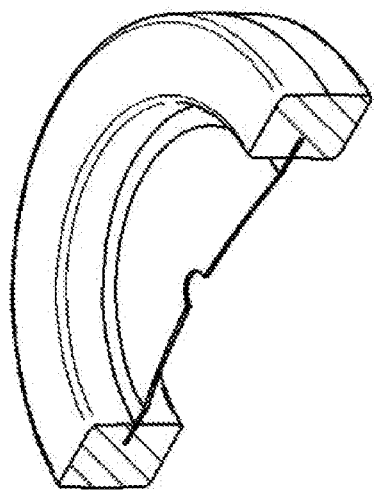
FIG. 5B is a schematic drawing of one embodiment of an overmoulded dome made using the mould.
Figure 5A:
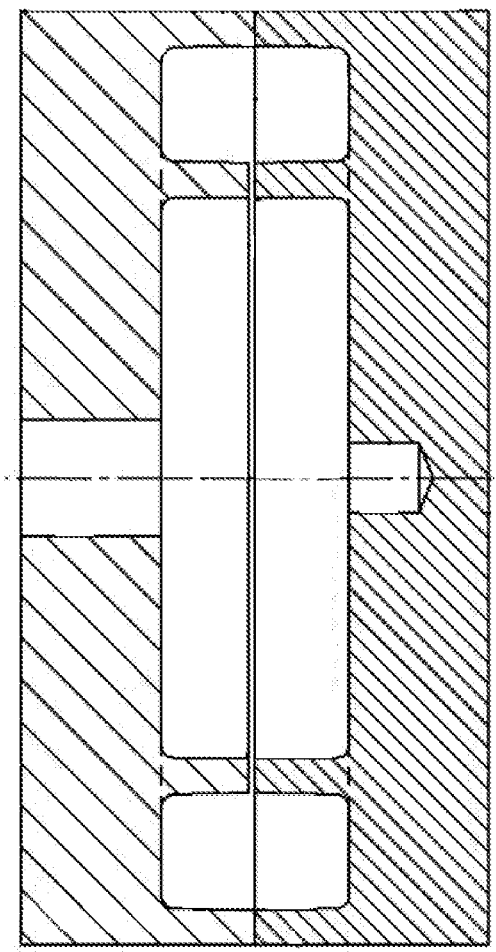
FIG. 5A is a schematic drawing of one embodiment of a mould for the over moulding of the dome.
Figure 6A:
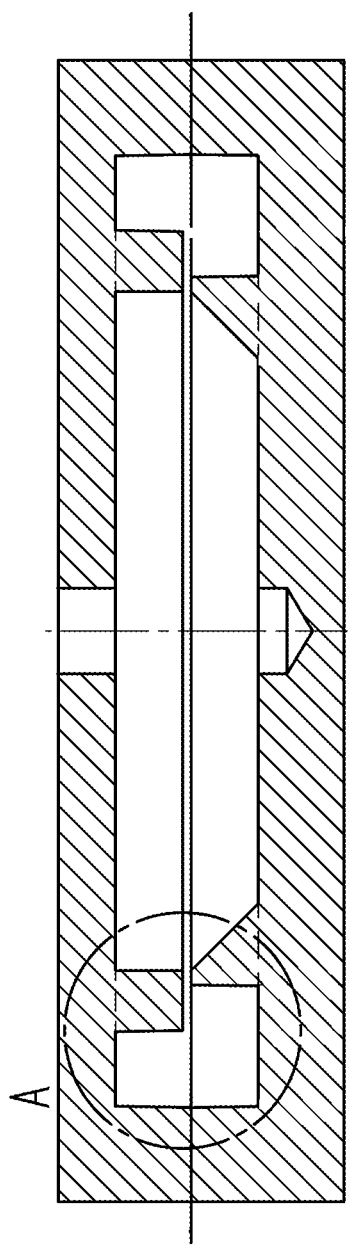
FIGS. 6A to 6C are schematic drawings of another embodiment of a mould for the over moulding of the dome.
Figure 6C:
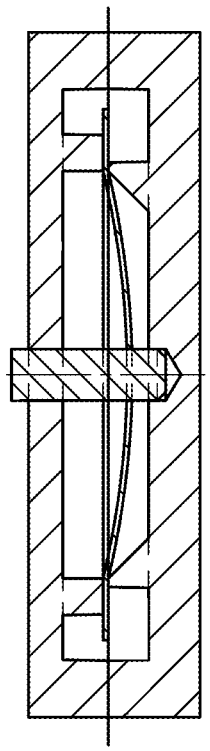
Figure 6B:
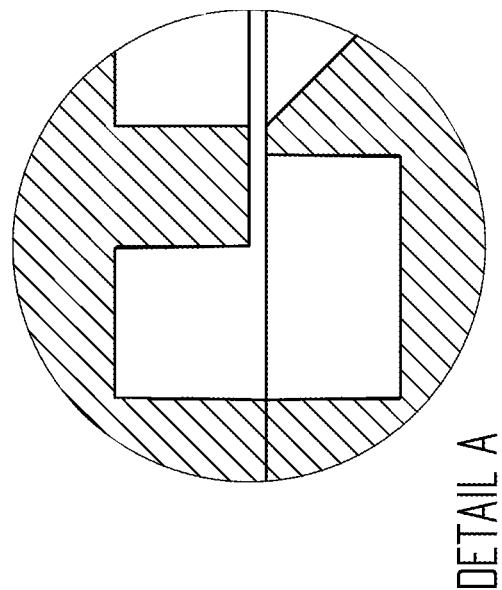
Figure 7:
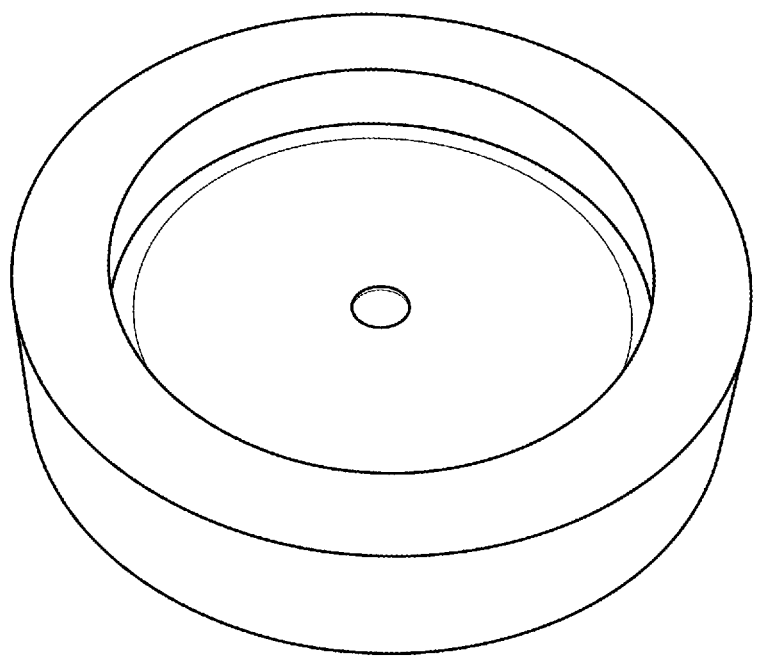
FIG. 7 is a photograph of one embodiment of an overmoulded dome in the unloaded state.
Figure 8A:
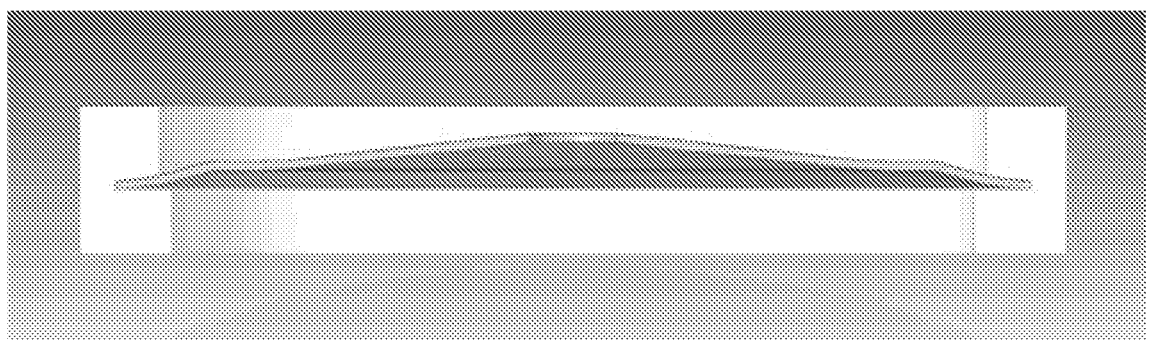
FIG. 8A is a schematic CAD representation of one embodiment of an overmoulded dome in the loaded state.

The central region of the dome may be "loaded" by displacing it perpendicularly to the flat of the dome's base until the concavity inverts through buckling ("snap-through"). A "loader" can be used to load the dome, for example an approximately 15.3 mm diameter plastic ring with a section of 1.3 mm is pushed against the dome convex side until loading. This loaded dome may then be placed on a test jig (See FIGS. 4A to 4C), comprised of a hollow cylinder for support around the unloaded flat circumferential region, with the convex surface rising in the vertical plane. A window in the jig enables the tracking of a 450 mg projectile accelerated by the dome actuation, via a high speed camera (40,000 fps). A motorised stage with a cell force enables the triggering of the dome at a constant speed of 50 mm/min, while recording the applied load and deflection of the dome at the same time. The triggering is achieved with a plastic trigger having similar dimensions as the "loader".

The dome may be considered a shell structure (a three-dimensional solid whose thickness is very small compared with its other dimensions). When a compressive load is applied axially to the dome, its geometry evolves (i.e. deformation) under the increasing bending moment while accommodating the build-up of membrane and shear forces, and related stresses. This phase of deformation corresponds to the first elastic part of the force vs. displacement graph, where the resulting load on the dome increases linearly with the deformation (characterised by the apex displacement) (See FIG. 1). After reaching a defined load some areas of the dome start to experience buckling, meaning that locally these areas become unstable and are poised to snap-through in order to minimise their energy level. However, as a whole, more areas of the dome are still in the elastic behaviour (and would return to the initial geometry if the load were removed), than there are areas of buckling. As the forced deformation increases, more and more of local areas of the dome are buckling which results in reducing the load experienced by the dome, until a peak load, and consequent decrease of load (middle of the graph, FIG. 1). Ultimately there comes a point where the resultant buckling of the components becomes similar to the elastic back-force resultant of the non-buckling component, which results in a critically unstable dome. Any further deformation, vibration, stress etc. makes the domes enter a highly transient behaviour where the buckling propagates to the full surface of the dome, resulting in the dynamic inversion of the dome. The dome inverts in order to minimise the bending moment, shear and membrane stresses, and reaches a lower energetic state (the inverted state). The transient nature of the inversion results in a high acceleration and deceleration of the centre part of the dome (apex), which can be used as a high speed actuator to project a device such as a microprojection array. In the graph of FIG. 1, the final section of the graph displays the load collapse to zero as the dome goes faster than the motorised stage of the recording cell force.

In order to trigger the dome, the user needs to bring the dome to this critical state where the buckling propagates to the full dome. The user applies a peak load which can be significantly higher than the snap-through force.

As a baseline, the embodiment of the particular asymmetric bistable dome described above, when non constrained (stand-alone dome) has a peak loading force of 195±2.85 N and speed around 11 m/s (loading speed) for a peak trigger force of 96±2.24 N, which results in an unloading speed of 20.80±1.34 m/s. This design provides a two-fold increase of the performance with a halving of the force resulting in the doubling of the speed (convention loading-triggering).

The device and methods of the present invention bring the dome close to this critically unstable state where a high ratio of the dome surface is buckling, ready to propagate to the full dome. By close it is meant that a low remaining load still needs to be applied by the user to ultimately bring the dome to the critical state. The remaining force ("the trigger force") needs to be tailored in order to fall in a range, where the maximum corresponds to a force which is considered too high to deliver by a user and/or to be received by a patient, and the minimum corresponds to a force which is not sufficient to prevent any unintentional triggering. The critical force can vary with imperfections in the dome (stamping, grain, defects, dints etc.), with the triggering (off-centring, angle, shape and size), with the dynamic of the triggering (low speed, high impact speed, vibrations) and stress variation (temperature, humidity, dilatation of steel/plastic). Therefore, some buffering needs to be considered in choosing the ends of the trigger force range. The range of the triggering force for a encased dome may be from 5 to 100N, or from 5 to 90N or from 5 to 80N or from 5 to 70N or from 5 to 60N, or from 5 to 50N or from 5 to 40N, or from 5 to 30N or from 5 to 20N or from 5 to 10N, or from 10 to 100N, or from 10 to 90N or from 10 to 80N, or from 10 to 70N or from 10 to 60N, or from 10 to 50N or from 10 to 40N, or from 10 to 30N or from 10 to 20N, or from 20 to 100N or from 20 to 90N or from 20 to 80N, or from 20 to 70N or from 20 to 60N, or from 20 to 50N or from 20 to 40N, or from 20 to 30N or from 30 to 100N or from 30 to 90N or from 30 to 80N, or from 30 to 70N or from 30 to 60N, or from 30 to 50N or from 30 to 40N, or from 40 to 100N or from 40 to 90N or from 40 to 80N, or from 40 to 70N or from 40 to 60N, or from 40 to 50N or from 50 to 200N, or from 50 to 90N or from 50 to 80N, or from 50 to 70N or from 50 to 60N, or from 60 to 100N or from 60 to 90N or from 60 to 80N, or from 60 to 70N or from 70 to 100N or from 70 to 90N, or from 70 to 80N or from 80 to 100N or from 80 to 90N, or from 90 to 100N. The range of the triggering force for an stand-alone dome may be from 100 to 200N, or from 100 to 190N or from 100 to 180N, or from 100 to 170N or from 100 to 160N, or from 100 to 150N or from 100 to 140N, or from 100 to 130N or from 100 to 120N, or from 100 to 110N or from 110 to 200N, or from 110 to 190N or from 110 to 180N, or from 110 to 170N or from 110 to 160N, or from 110 to 150N or from 110 to 140N, or from 110 to 130N or from 110 to 120N or from 120 to 200N, or from 120 to 190N or from 120 to 180N, or from 120 to 170N or from 120 to 160N, or from 120 to 150N or from 120 to 140N, or from 120 to 130N or from 130 to 200N, or from 130 to 190N or from 130 to 180N, or from 130 to 170N or from 130 to 160N, or from 130 to 150N or from 130 to 140N, or from 140 to 200N, or from 140 to 190N or from 140 to 180N, or from 140 to 170N or from 140 to 160N, or from 140 to 150N or from 150 to 200N, or from 150 to 190N or from 150 to 180N, or from 150 to 170N or from 150 to 160N, or from 170 to 200N or from 170 to 200N, or from 170 to 190N or from 170 to 180N, or from 180 to 200N or from 180 to 190N, or from 190 to 200N.

The range of the loading force for a encased dome may be from 100 to 400N, or from 100 to 350N or from 100 to 300N, or from 100 to 250N or from 100 to 200N, or from 100 to 200N or from 100 to 150N, or from 150 to 400N or from 150 to 350N, or from 150 to 300N or from 150 to 250N or from 150 to 200N, or from 200 to 400N or from 250 to 350N, or from 200 to 300N or from 200 to 250N, or from 250 to 400N or from 250 to 350N or from 250 to 300N or from 300 to 400N, or from 300 to 350N or from 350 to 400N. The range of the loading force for an stand-alone dome may be from 100 to 200N, or from 100 to 190N or from 100 to 180N, or from 100 to 170N or from 100 to 160N, or from 100 to 150N or from 100 to 140N, or from 100 to 130N or from 100 to 120N, or from 100 to 110N or from 110 to 200N, or from 110 to 190N or from 110 to 180N, or from 110 to 170N or from 110 to 160N, or from 110 to 150N or from 110 to 140N, or from 110 to 130N or from 110 to 120N or from 120 to 200N, or from 120 to 190N or from 120 to 180N, or from 120 to 170N or from 120 to 160N, or from 120 to 150N or from 120 to 140N, or from 120 to 130N or from 130 to 200N, or from 130 to 190N or from 130 to 180N, or from 130 to 170N or from 130 to 160N, or from 130 to 150N or from 130 to 140N, or from 140 to 200N, or from 140 to 190N or from 140 to 180N, or from 140 to 170N or from 140 to 160N, or from 140 to 150N or from 150 to 200N, or from 150 to 190N or from 150 to 180N, or from 150 to 170N or from 150 to 160N, or from 170 to 200N, or from 170 to 190N or from 170 to 180N, or from 180 to 200N or from 180 to 190N, or from 190 to 200N.

The ratio of the triggering force to the loading force may be from about 1:100 or from about 1:90 or from about 1:80 or from about 1:70 or from about 1:60 or from about 1:50 or from about 1:40 or from about 1:30 or from about 1:20 or from about 1:10 or from about 1:5. The ratio of the triggering force to the loading force may be from about 1:100 to about 1:5 or from about 1:90 to about 1:5 or from about 1:80 to about 1:5 or from about 1:70 to about 1:5 or from about 1:60 to about 1:5 or from about 1:50 to about 1:5 or from about 1:40 to about 1:5 or from about 1:30 to about 1:5 or from about 1:20 to about 1:5 or from about 1:10 to about 1:5 or from about 1:100 to about 1:10 or from about 1:90 to about 1:10 or from about 1:80 to about 1:10 or from about 1:70 to about 1:10 or from about 1:60 to about 1:10 or from about 1:50 to about 1:10 or from about 1:40 to about 1:10 or from about 1:30 to about 1:10 or from about 1:20 to about 1:10.

Attempts to force the loaded dome to achieve this critical state by compressing the dome cannot be achieved by a placing the dome in a simple casing. Once the user further deforms the pre-activated dome, the dome will disconnect from the casing and the full load (e.g. 100 N) would be transmitted to the user. The dome will either go back to the unloaded position, or snap-through to the loaded position.

The domes of the present invention are brought to a state of stable partial buckling while transitioning from the unloaded to the loaded positions. This intermediate energetic state cannot be captured for a non-encased device as the state is highly transient due to the dynamics of snapping-through which makes the dome pass through this state, and reach instead the lower energetic state of the fully inverted dome. When the equilibrium of this intermediate energy is stable, the user can apply a load from this state without having all the 100 N of load retransmitted to the user. This is achieved by encasing the unloaded dome, and by loading the dome in a casing. The casing may be designed such that the transition of the loading dome is stopped in the desired state close to critical stable intermediary energetic state. Although the casing needs to provide some load against the dome to keep it in this intermediary position and prevent the dome from transitioning to reach the lower energetic state of the fully inverted dome, most of the load is provided by the buckled partition of the dome, as demonstrated by the fact that an extra smaller load (the "trigger force") can be applied without resuming the full load of 100 N.

When the dome is triggered from this new position, the required trigger force is lower than for the unconstrained loaded position; however, the velocity the dome achieves on release is not prejudiced. The amount of constraint can be used to reduce the trigger force on a high performance dome (high speed) without sacrificing the velocity. A comparison between constrained (encased) and unconstrained (non-encased) domes show that the velocity of the constrained dome is slightly increased from [20.80±1.34] m/s to [22.3±1.07] m/s. This may due to the fact that most of the constrained dome (the buckled partition) is ready to snap-through, whereas in the case of the unconstrained dome some dynamic is lost in fluctuating vibrations around the critical state.

One particular embodiment of the encapsulated dome is accomplished by over-moulding the outer rim of the dome in an appropriate material including but not limited to plastic, ceramic, aluminium metals, steel, glass, carbon fibers or combinations thereof prior to loading the dome (See FIGS. 5A and 5B, and FIGS. 6A to 6C for mould designs and FIG. 7 and FIGS. 8A to 8C for an example of over moulded dome). Over moulding the dome with a plastic lends itself to integrating the overmoulded dome into a microprojection array applicator device. This design can be scaled-up for high-number throughput production at a low cost per part. The plastic dome-encasing material prevents the dome from transitioning from the unloaded state to the loaded states while maintaining the dome at the equilibrium state and maintains the dome in this desired state over the shelf-life of the device (high creeping resistance). The devices of the present invention are capable of being stored for long periods of time without the dome transitioning from the unloaded state to the loaded state. The devices of the present invention may be stored without transitioning from the unloaded state to the loaded state for at least about 6 months or about 1 year or about 2 years or about 3 years or about 4 years or about 5 years or about 6 years or about 7 years or about 8 years or about 9 years or about 10 years or more. The devices of the present invention may be stored without transitioning from the unloaded state to the loaded state for about 1 year to 20 years or from 1 year to 15 years or from 1 year to 10 years or from 1 year to 5 years or from 2 years to 20 years or from 2 years to 15 years or from 2 year to 10 years or from 2 year to 5 years or from 3 years to 20 years or from 3 year to 15 years or from 3 year to 10 years or from 3 year to 5 years or from 4 years to 20 years or from 4 year to 15 years or from 4 years to 10 years or from 4 year to 5 years or from 5 years to 20 years or from 5 years to 15 years or from 5 years to 10 years or from 10 years to 20 years or from 15 years to 20 years.

The dome-encasing material should have high impact strength to sustain the shock of the inverting dome while loading. Loading and maintaining the dome in its desired state can be achieved in at least two ways, stiff or flexible encasing designs (see FIGS. 9A and 9B). First, provide an over moulding which restrains the bending of the dome. This approach enables an easy tailoring of the bending of the dome by varying the dimensions of the dome-encasing material, and hence the compliance of the material. Having flexible parts, however, may not be the most favourable design in an applicator. Second, providing a stiff dome-encasing material that holds a part of the dome tightly at some anchoring points of the dome (e.g. half of the outer rim on the concave side of the unloaded dome). This approach requires a specific design of the dome-encasing material so that the dome is stabilised at the desired trigger force, more compression from the dome-encasing material would alter the dynamic of the dome (lose of the bi-stability), less compression would increase the trigger force. For instance, the right "opening" must be achieved to permit the dome flex. Dome-encasing materials such as plastics with high flexural modulus (>10 GPa) are preferred.

Reinforced plastics are particularly good candidates for stiff and low creep plastics. Plastics that can be used in the casing for the domes include but are not limited to 15%-50% glass reinforced nylon 6, 40% glass reinforced polyphenylene sulphide (PPS) and 50% GF PBT (polybutylene) or PBT/PET blends (polybutylene and polyethylene terephthalate). Other dome-encasing materials that can be used in the devices and methods of the present invention include but are not limited to ceramic, aluminium (powder metallurgy, reinforced plastic with steel, glass or carbon fibres or a combination thereof. Consideration should be given to moisture intake and other parameters (temperature, light) which may influence the mechanical properties of the plastics (tensile modulus, flexural modulus etc.) For instance, 15% glass filled nylon may not be preferred if the dome part is subject to humidity. The moisture uptake at equilibrium is about 2.2% in weight at room temperature and 50% RH. This leads to a loss of 50 to 60% in the flexural modulus, and similar reduction of 50% in the tensile strength and flexural strength of the material. In applicators for the use in projecting microprojection arrays into skin, the inner environment will be kept dry, and the device stored in ambient or refrigerated conditions, protected from light.

The over moulded portion of the device will depend in part on the diameter of the dome it encases. The diameter of the over moulding may be from about 5 to 100 mm, or from about 5 to 90 mm or from about 5 to 80 mm or from about 5 to 70 mm or from about 5 to 60 mm or from about 5 to 50 mm or from about 5 to about 40 mm or from about 5 to 30 mm or from about 5 to 20 mm or from about 5 to about 10 mm or from about 10 to 100 mm, or from about 10 to 90 mm about 10 to 80 mm, or from about 10 to 70 mm or from about 10 to 60 mm or from about 10 to 50 mm or from about 10 to 40 mm or from about 10 to 30 mm or from about 10 to about 20 mm or from about 20 to 80 mm, or from about 20 to 70 mm or from about 20 to 60 mm or from about 20 to 50 mm or from about 20 to 40 mm or from about 20 to 30 mm or from about 30 to 80 mm, or from about 30 to 70 mm or from about 30 to 60 mm or from about 30 to 50 mm or from about 30 to 40 mm or from about 40 to 80 mm, or from about 40 to 70 mm or from about 40 to 60 mm or from about 40 to 50 mm or from about 50 to 80 mm, or from about 50 to 70 mm or from about 50 to 60 mm. The thickness of the overmoulding may be from about 1 to 30 mm or from about 1 to 25 mm or from about 1 to 20 mm or from about 1 to 15 mm or from about 1 to 10 mm or from about 1 to 5 mm or from about 5 to 30 mm or from about 5 to 25 mm or from about 5 to 20 mm or from about 5 to 15 mm or from about 5 to 10 mm or from about 10 to 30 mm or from about 10 to 25 mm or from about 10 to 20 mm or from about 10 to 15 mm or from about 15 to 30 mm or from about 15 to 25 mm or from about 15 to 20 mm or from about 20 to 30 mm or from about 20 to 25 mm or from about 25 to 30 mm. The over moulding of the dome will encroached on the dome for about 1 to 30 mm or from about or from about 1 to 25 mm or from about 1 to 20 mm or from about 1 to 15 mm or from about 1 to 10 mm or from about 1 to 5 mm or from about 5 to 30 mm or from about 5 to 25 mm or from about 5 to 20 mm or from about 5 to 15 mm or from about 5 to 10 mm or from about 10 to 30 mm or from about 10 to 25 mm or from about 10 to 20 mm or from about 10 to 15 mm or from about 15 to 30 mm or from about 15 to 25 mm or from about 15 to 20 mm or from about 20 to 30 mm or from about 20 to 25 mm or from about 25 to 30 mm).

In one embodiment the primed dome is held is in place in the housing and/or applicator by using ultrasound crimping to encase the flattened edge of the dome is the housing (See FIGS. 37 and 38). In one embodiment the ultrasound crimping may be used to crimp a portion of the housing (such as a plastic rib as shown in FIGS. 37A and 37B) over the flattened edge of the dome to hold the dome in place. FIG. 39A shows the top view of a picture of an applicator for a microprojection array and FIG. 39B shows a top view of a picture of an applicator in which the microprojection array is being applied to a patient's skin. As can be seen in the Figure the top of the applicator is a collapsible trigger mechanism which triggers the dome to release the microprojection array if the trigger mechanism is pressured with enough force to activate the dome. One the dome is activated it can impact the microprojection array such that the array can be propelled from the applicator into the patient's skin.

In order to increase the creep resistance, the dome can be over-moulded with a plastic vault with a pattern of ribs (See FIGS. 10 to 12). The use of a plastic vault could be incorporated in a 3 steps process in the same mould:
1. Over mould the unloaded dome's outer rim;
2. Load the dome in the mould, the dome reaches its near critical state; and
3. Over mould the convex side of the loaded dome with a non-contacting pattern of ribs (plastic vault), which results in the covering of the dome in its critical state, backed by the stiffness of the ribs pattern.

Figure 10:
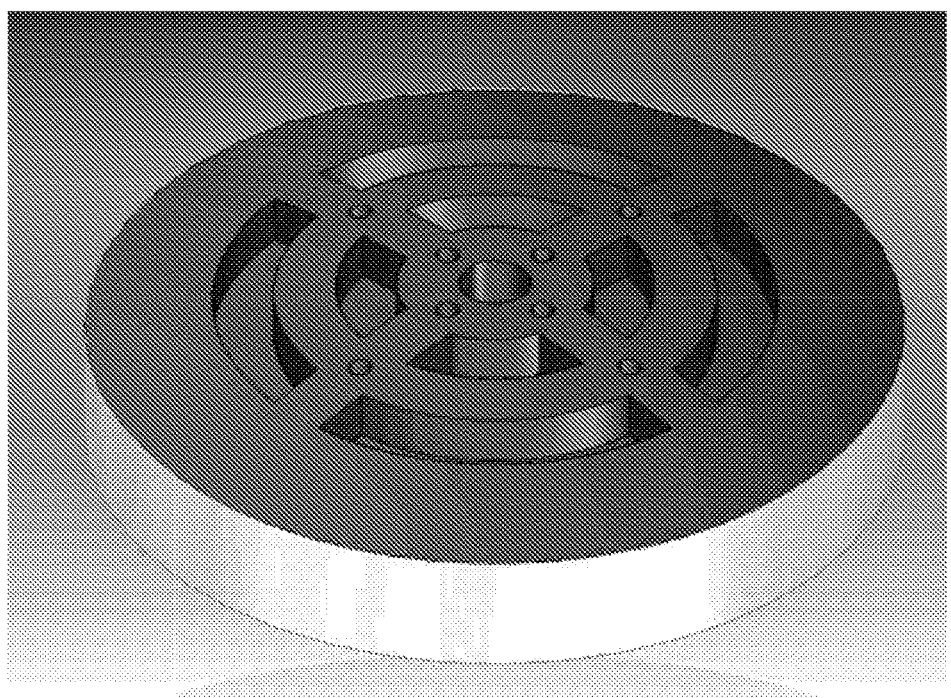
FIG. 10 is a representation of one embodiment of an overmoulded dome with vaulted ribs.
Figure 11:
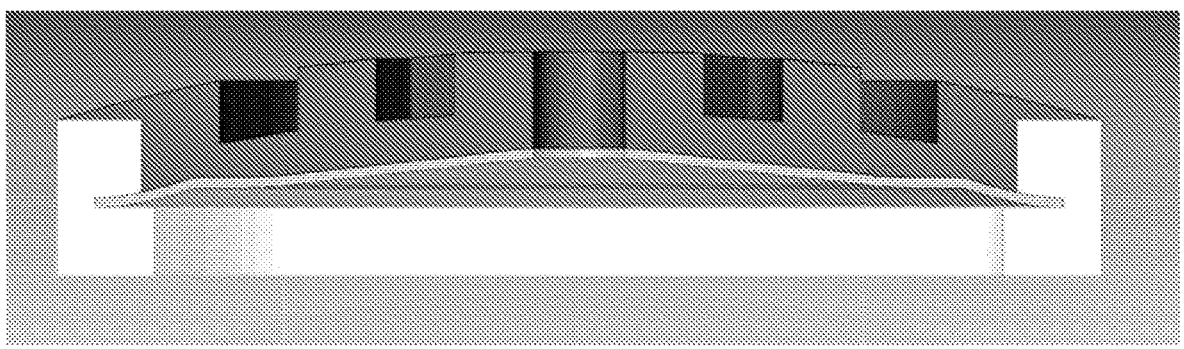
FIG. 11 is a side view of one embodiment of an overmoulded dome with vaulted ribs.
Figure 12:
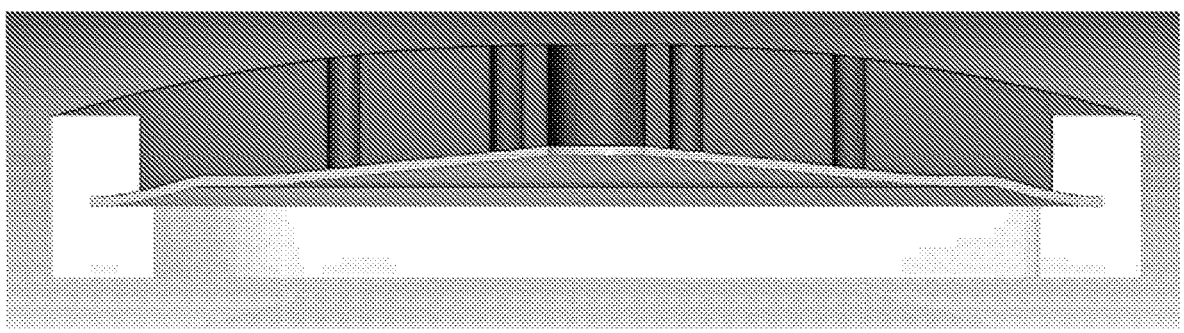
FIG. 12 is a side view of one embodiment of an overmoulded dome with vaulted ribs.
Figure 17:
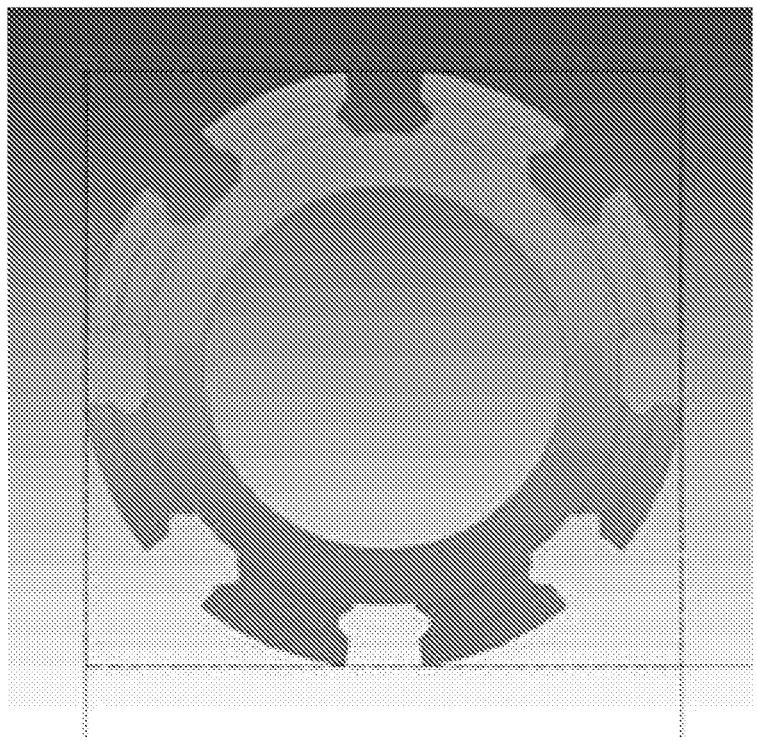
FIG. 17 is a representation of another embodiment of a foldable metal ring for encasing a dome.
Figure 18:
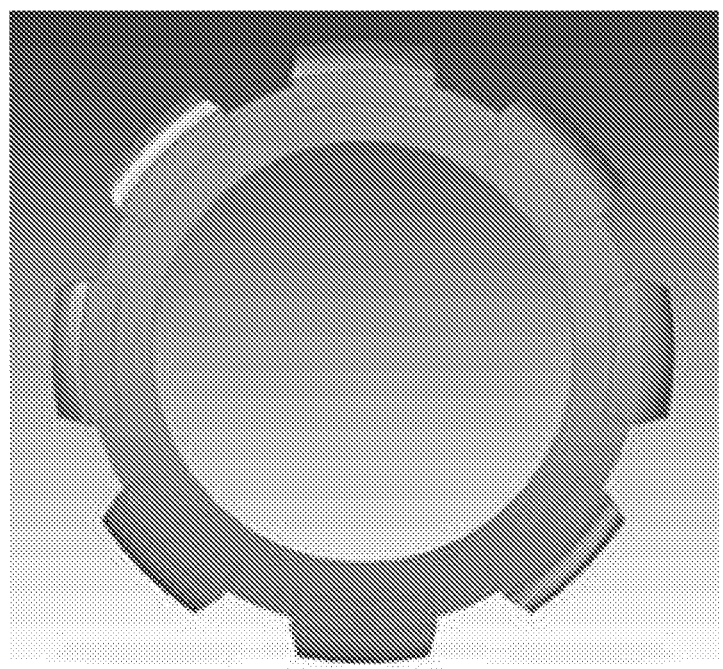
FIG. 18 is a representation of another embodiment of a foldable metal ring for encasing a dome.
Figure 19:
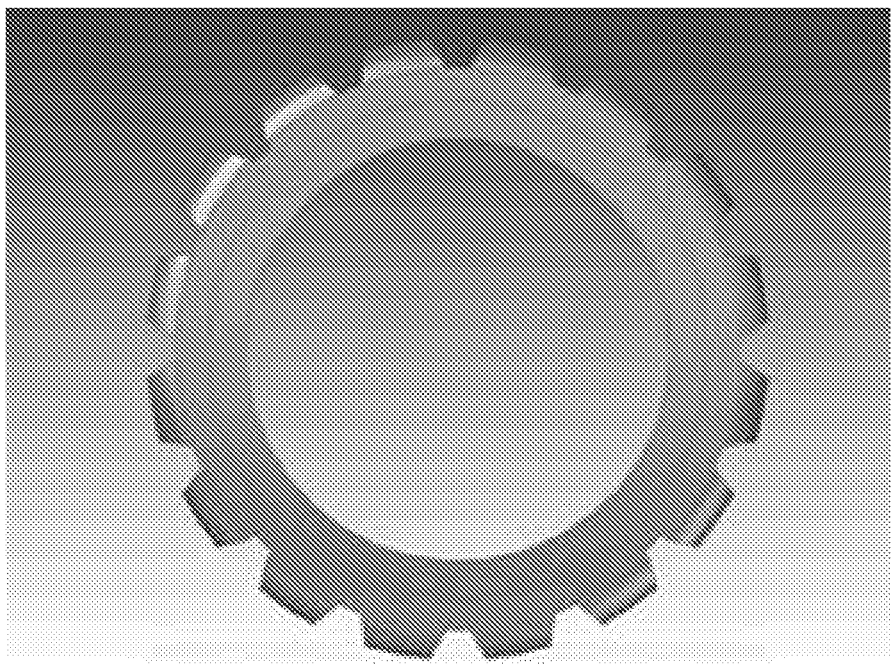
FIG. 19 is a representation of another embodiment of a foldable metal ring for encasing a dome.
Figure 20:
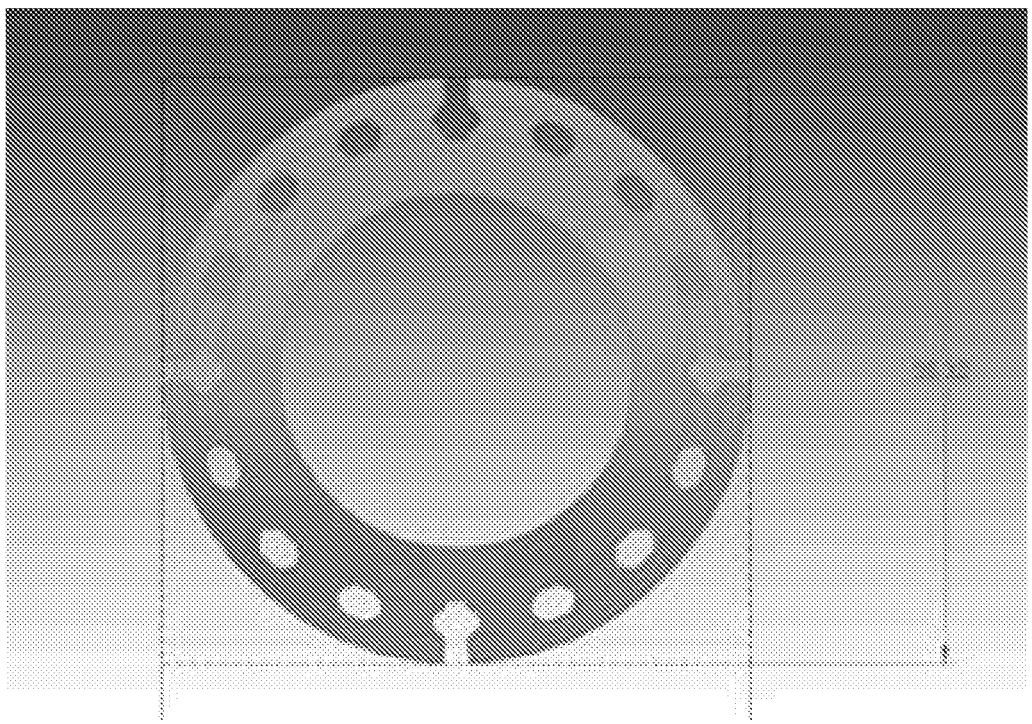
FIG. 20 is a representation of another embodiment of a foldable metal ring encasing a dome with holes to drive the folding.

The pattern of plastic vault and ribs enables the stiffening and holding of the dome in place and prevent creeping. The use of ribs instead of a solid body reduces the need for too much extra material. The fact that the ribs do not touch the domes leads to a simple moulding process as the exact shape of the domes need not be known and thus the ribs can vary slightly. The cavity between the dome and the ribs may be filled by a covering plastic vault. It may be useful to provide a coating to avoid adhesion of the metal dome with the plastic vault. (Coating on the dome, on the plastic, or both). FIG. 10 shows a dome casing with an over moulded vault with ribs. In FIG. 11, the dome in grey is first moulded in the unloaded state (white plastic), then while still in the mould the dome is pushed until loading, then a second over moulding occurs over the convex side of the over moulded dome. It may also be useful to provide some tiny holes in the plastic in order to prevent shrinkage of the ribs (thicker section otherwise), and allow some venting for the dome (See FIG. 12). The holes may be made by small pins such that the pins are sufficiently small so that the contacting section with the dome can be kept to a simple compliant contacting shape.

Figure 21A:
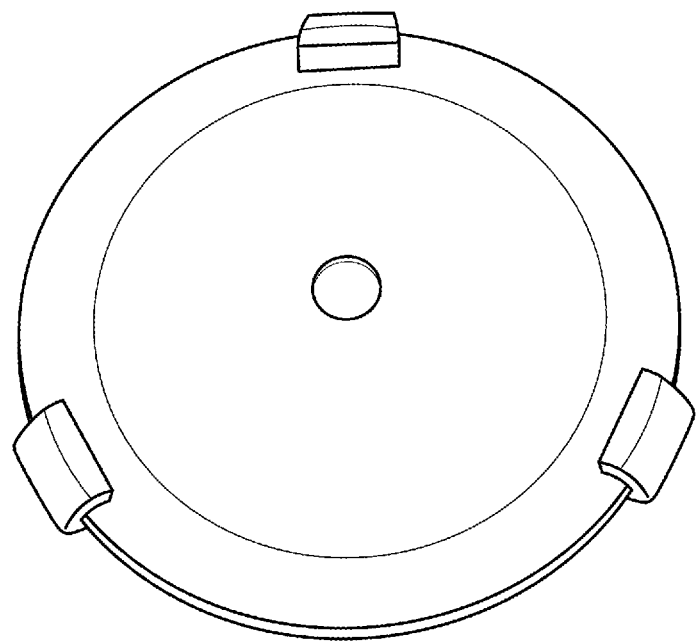
FIG. 21A shows a primed dome in a metal ring with three tabs.
Figure 21B:
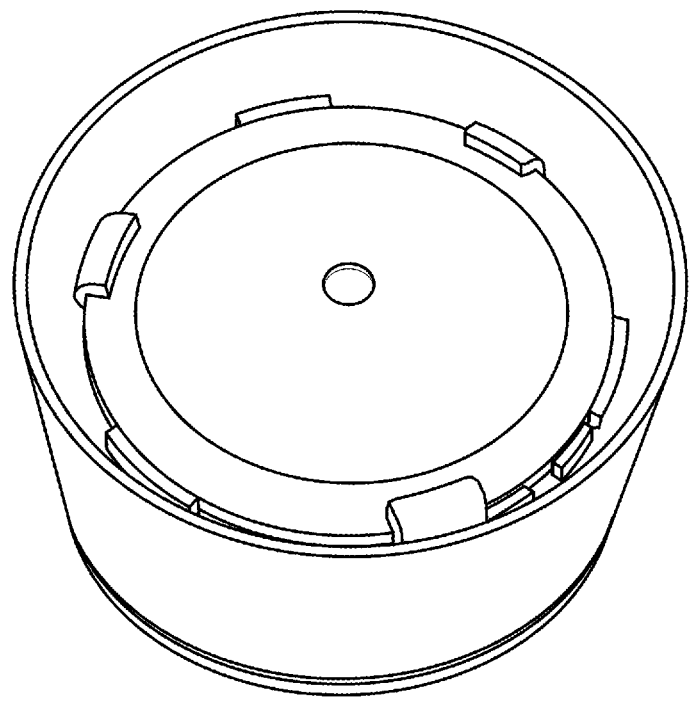
FIG. 21B shows the dome inserted in an injected moulded applicator.
Figure 22B:
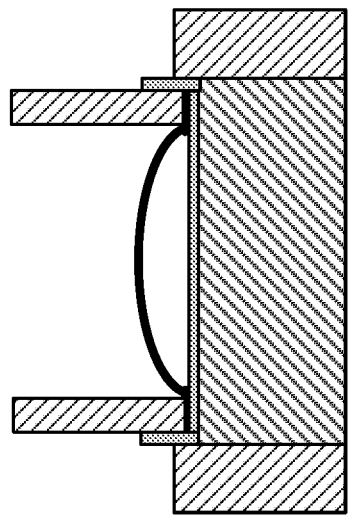
FIGS. 22A to 22D are representations of steps in a punch process whereby the foldable metal ring is pressed into encasing a dome.
Figure 22D:
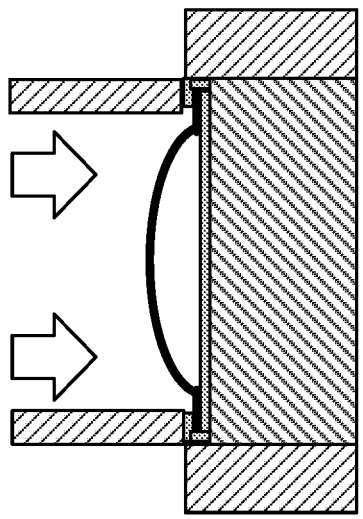
Figure 22A:
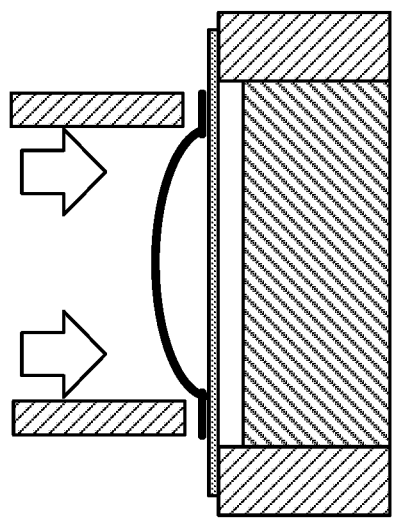
Figure 22C:
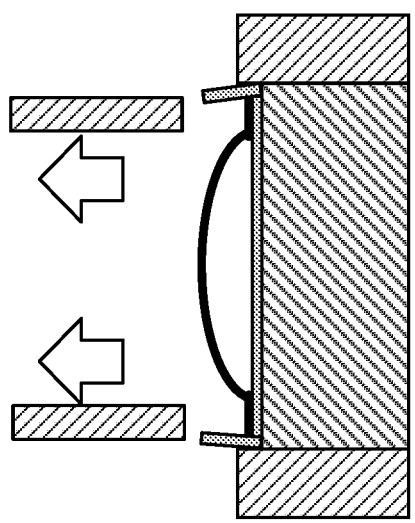
Figure 22F:
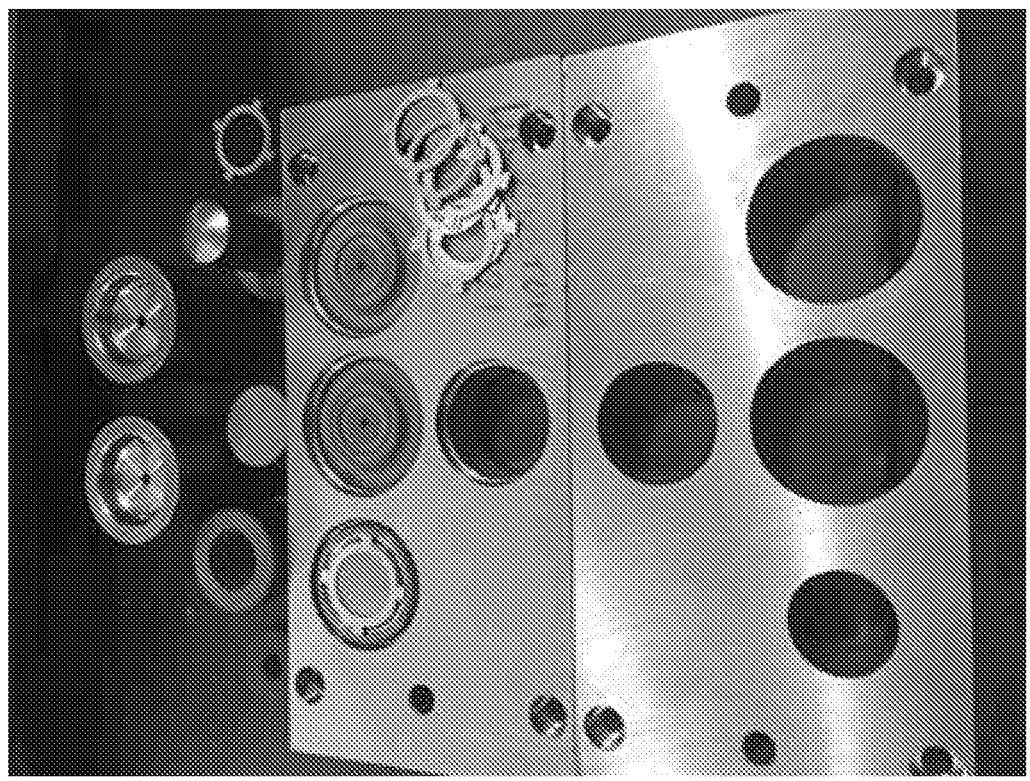
FIGS. 22E and 22F are photographs of domes and encasements in various stages of assembly.
Figure 22E:
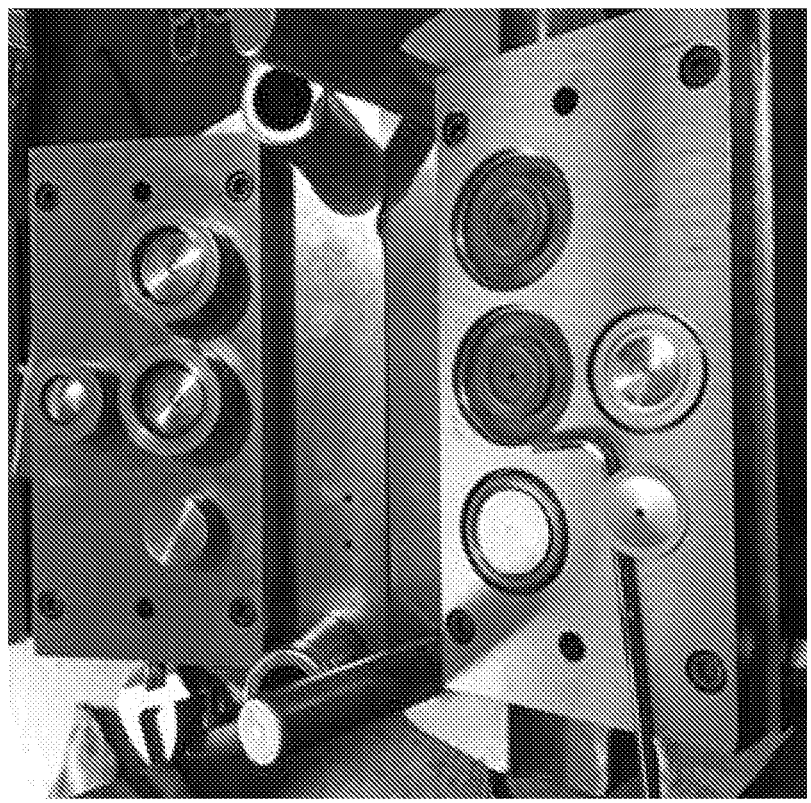
Figure 22G:
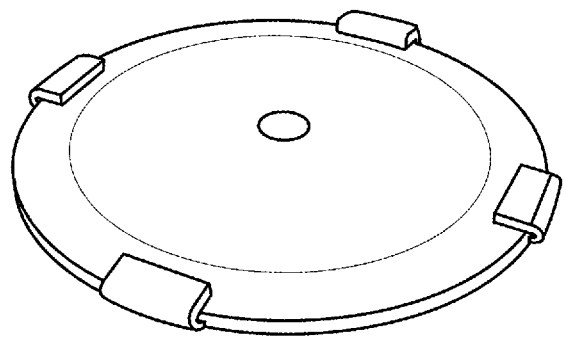
FIG. 22G is a photograph of an encased dome having four tabs as shown from above.
Figure 22H:
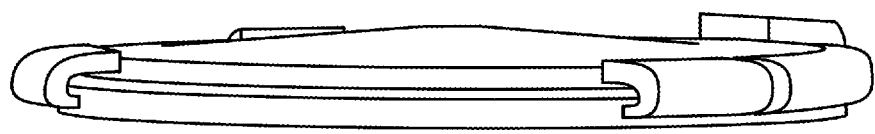
FIG. 22H is a photograph of an encased dome having four tabs as shown from the side.

Another embodiment to encase the dome is accomplished by using a foldable metal ring which envelopes the outer edge of the dome. A metal strip of thickness 0.5 mm to 2 mm may be cut into a ring that can be folded back onto the dome, see FIGS. 13 to 21. The foldable metal ring can have tabs or can be a continuous ring without tabs. The metal strip may be made of but is not limited to any steel, stainless steel, aluminium or any other metal. It is preferred that a metal that can be bend without too much spring back and able to sustain a load on the loaded dome is selected. The metal strip can be cut by punch tool, laser cut or waterjet cut for example. The design of the foldable ring is such that the inner diameter 1 (ID1) enables the unloaded (and triggered) dome to sit flush on the ring (see FIG. 13), and the design of the extended radial tabs such as that when folded the tabs extend to hold back the dome to fully load and set the dome to its desired trigger force in a way similar to that described above for the over-moulded dome. The foldable metal ring may encompass the entire dome edge or portions thereof. This extension can be characterised by another inner diameter 2 (ID2). FIG. 21A shows a primed dome in a metal ring with three tabs and FIG. 21B shows the dome inserted in an injected moulded applicator.

In some embodiment of the devices of the present invention the hardness of the steel used for the dome is from about 500 to about 650 HV (Vickers Hardness) pre-heat treatment. The hardness of the steel used for the dome may be from about 400 to about 750 HV or from about 450 to about 750 HV or from about 500 to about 750 HV or from about 550 to about 750 HV or from about 600 to about 750 HV or from about 650 to about 750 HV or from about 700 to about 750 HV or from about 400 to about 700 HV or from about 450 to about 700 HV or from about 500 to about 700 HV or from about 550 to about 700 HV or from about 600 to about 700 HV or from about 650 to about 700 HV or from about 400 to about 650 HV or from about 450 to about 650 HV or from about 500 to about 650 HV or from about 550 to about 650 HV or from about 550 to about 600 HV or from about 600 to about 750 HV or from about 600 to about 700 HV or from about 600 to about 650 HV or from about 540 to about 600 HV.

The process for making the encased dome can be accomplished with a first vertical bending of the tabs in a punch tool, followed by folding the tabs down onto the dome, see FIGS. 22A to 22H. In some embodiments a thin ring with fewer tabs may provide similar performance compared to thicker foldable metal rings with more tabs while providing for a lower weight and lower cost. The ID between the closed tabs may be the dominant parameter for the tailoring of the trigger force. In one embodiment the tool forces the tabs to close with an ID Ø of between 26.7-26.8 mm. In an alternate embodiment the encasement may comprise two metal rings which may be attached to the outer edge of the dome by welding or by constructing the ring with a pocket for the dome. The cover ring is tailored to the right ID to control the trigger force and the dome is sandwiched by the two rings clamped together by screws or other attachment devices for holding the rings and dome together. See FIG. 30. By changing the depth of the pocket and the IDs of the rings different performances can be achieved.

FIG. 21 shows the design of a ring which delivered a speed of 25.89±0.88 m/s for 27.40±6.67 N (n=5 replicas) after heat treatment.

The foldable metal rings may be from about 0.1 mm to about 5 mm, or from about 0.1 mm to about 4.5 mm, or from about 0.1 mm to about 4 mm, or from about 0.1 mm to about 3.5 mm, or from about 0.1 mm to about 3 mm, or from about 0.1 mm to about 2.5 mm, or from about 0.1 mm to about 2 mm, or from about 0.1 mm to about 1.5 mm, or from about 0.1 mm to about 1 mm, or from about 0.1 mm to about 0.5 mm, or from about 0.2 mm to about 5 mm, or from about 0.2 mm to about 4.5 mm, or from about 0.2 mm to about 4 mm, or from about 0.2 mm to about 3.5 mm, or from about 0.2 mm to about 3 mm, or from about 0.2 mm to about 2.5 mm, or from about 0.2 mm to about 2 mm, or from about 0.2 mm to about 1.5 mm, or from about 0.2 mm to about 1 mm, or from about 0.2 mm to about 0.5 mm, or from 0.3 mm to about 5 mm, or from about 0.3 mm to about 4.5 mm, or from about 0.3 mm to about 4 mm, or from about 0.3 mm to about 3.5 mm, or from about 0.3 mm to about 3 mm, or from about 0.3 mm to about 2.5 mm, or from about 0.3 mm to about 2 mm, or from about 0.3 mm to about 1.5 mm, or from about 0.3 mm to about 1 mm, or from about 0.3 mm to about 0.5 mm, or from 0.4 mm to about 5 mm, or from about 0.4 mm to about 4.5 mm, or from about 0.4 mm to about 4 mm, or from about 0.4 mm to about 3.5 mm, or from about 0.4 mm to about 3 mm, or from about 0.4 mm to about 2.5 mm, or from about 0.4 mm to about 2 mm, or from about 0.4 mm to about 1.5 mm, or from about 0.4 mm to about 1 mm, or from about 0.4 mm to about 0.5 mm, or from 0.5 mm to about 5 mm, or from about 0.5 mm to about 4.5 mm, or from about 0.5 mm to about 4 mm, or from about 0.5 mm to about 3.5 mm, or from about 0.5 mm to about 3 mm, or from about 0.5 mm to about 2.5 mm, or from about 0.5 mm to about 2 mm, or from about 0.5 mm to about 1.5 mm, or from about 0.5 mm to about 1 mm, or from about 0.6 mm to about 5 mm, or from about 0.6 mm to about 4.5 mm, or from about 0.6 mm to about 4 mm, or from about 0.6 mm to about 3.5 mm, or from about 0.6 mm to about 3 mm, or from about 0.6 mm to about 2.5 mm, or from about 0.6 mm to about 2 mm, or from about 0.6 mm to about 1.5 mm, or from about 0.6 mm to about 1 mm, or from 0.7 mm to about 5 mm, or from about 0.7 mm to about 4.5 mm, or from about 0.7 mm to about 4 mm, or from about 0.7 mm to about 3.5 mm, or from about 0.7 mm to about 3 mm, or from about 0.7 mm to about 2.5 mm, or from about 0.7 mm to about 2 mm, or from about 0.7 mm to about 1.5 mm, or from about 0.7 mm to about 1 mm, or from about 0.8 mm to about 5 mm, or from about 0.8 mm to about 4.5 mm, or from about 0.8 mm to about 4 mm, or from about 0.8 mm to about 3.5 mm, or from about 0.8 mm to about 3 mm, or from about 0.8 mm to about 2.5 mm, or from about 0.8 mm to about 2 mm, or from about 0.8 mm to about 1.5 mm, or from about 0.8 mm to about 1 mm, or from 0.9 mm to about 5 mm, or from about 0.9 mm to about 4.5 mm, or from about 0.9 mm to about 4 mm, or from about 0.9 mm to about 3.5 mm, or from about 0.9 mm to about 3 mm, or from about 0.9 mm to about 2.5 mm, or from about 0.9 mm to about 2 mm, or from about 0.9 mm to about 1.5 mm, or from about 0.9 mm to about 1 mm, or from about 1 mm to about 5 mm, or from about 1 mm to about 4.5 mm, or from about 1 mm to about 4 mm, or from about 1 mm to about 3.5 mm, or from about 1 mm to about 3 mm, or from about 1 mm to about 2.5 mm, or from about 1 mm to about 2 mm, or from about 1 mm to about 1.5 mm.

The number of tabs in the foldable metal ring can be from 2 to 20 or from 2 to 19 or from 2 to 18 or from 2 to 17 or from 2 to 16 or from 2 to 15 or from 2 to 14 or from 2 to 13 or from 2 to 12 or from 2 to 11 or from 2 to 10 or from 2 to 9 or from 2 to 8 or from 2 to 7 or from 2 to 6 or from 2 to 5 or from 2 to 4 or from 2 to 3 or from 3 to 20 or from 3 to 19 or from 3 to 18 or from 3 to 17 or from 3 to 16 or from 3 to 15 or from 3 to 14 or from 3 to 13 or from 3 to 12 or from 3 to 11 or from 3 to 9 or from 3 to 8 or from 3 to 7 or from 3 to 6 or from 3 to 5 or from 3 to 4 or from 4 to 20 or from 4 to 19 or from 4 to 18 or from 4 to 17 or from 4 to 16 or from 4 to 15 or from 4 to 14 or from 4 to 13 or from 4 to 12 or from 4 to 11 or from 4 to 10 or from 4 to 9 or from 4 to 8 or from 4 to 7 or from 4 to 6 or from 4 to 5 or from 5 to 20 or from 5 to 19 or from 5 to 18 or from 5 to 17 or from 5 to 16 or from 5 to 15 or from 5 to 14 or from 5 to 13 or from 5 to 12 or from 5 to 11 or from 5 to 9 or from 5 to 8 or from 5 to 7 or from 5 to 6 or from 6 to 20 or from 6 to 19 or from 6 to 18 or from 6 to 17 or from 6 to 16 or from 6 to 15 or from 6 to 14 or from 6 to 13 or from 6 to 12 or from 6 to 11 or from 6 to 10 or from 6 to 9 or from 6 to 8 or from 6 to 7 or from 7 to 20 or from 7 to 19 or from 7 to 18 or from 7 to 17 or from 7 to 16 or from 7 to 15 or from 7 to 14 or from 7 to 13 or from 7 to 12 or from 7 to 11 or from 7 to 9 or from 7 to 8 or from 8 to 20 or from 8 to 19 or from 8 to 18 or from 8 to 17 or from 8 to 16 or from 8 to 15 or from 8 to 14 or from 8 to 13 or from 8 to 12 or from 8 to 11 or from 8 to 10 or from 8 to 9 or from 2 to 8 or from 2 to 7 or from 2 to 6 or from 2 to 5 or from 2 to 4 or from 2 to 3 or from 3 to 20 or from 3 to 19 or from 9 to 18 or from 9 to 17 or from 9 to 16 or from 9 to 15 or from 9 to 14 or from 9 to 13 or from 9 to 12 or from 9 to 11 or from 9 to 10 or from 10 to 20 or from 10 to 19 or from 10 to 18 or from 10 to 17 or from 10 to 16 or from 10 to 15 or from 10 to 14 or from 10 to 13 or from 10 to 12 or from 10 to 11. The tabs of the ring can be of any shape such as rectangular or pyramidal or square and the tabs can be flat or curved as shown in Figures The performance of the encased dome may be improved with respect to speed, force and stability by conditioning the dome and the foldable metal ring in which it is encased. The encased domes may be treated with a heat treatment. The heat may be from about 300° C. to about 475° C. or from about 300° C. to about 450° C. or from about 300° C. to about 425° C. or from about 300° C. to about 400° C. or from about 300° C. to about 350° C. or from about 350° C. to about 500° C. or from about 350° C. to about 475° C. or from about 350° C. to about 450° C. or from about 350° C. to about 425° C. or from about 350° C. to about 400° C. or from about 375° C. to about 500° C. or from about 375° C. to about 475° C. or from about 375° C. to about 450° C. or from about 375° C. to about 425° C. or from about 400° C. to about 500° C. or from about 400° C. to about 475° C. or from about 400° C. to about 450° C. or from about 400° C. to about 425° C. The duration of the heating may be from about 1 hour to about 6 hours or from about 1 hour to about 5 hours or from about 1 hour to about 4 hours or from about 1 hour to about 3 hours or from about 1 hour to about 2 hours or from about 2 hour to about 6 hours or from about 2 hour to about 5 hours or from about 2 hour to about 4 hours or from about 2 hour to about 3 hours or from about 3 hour to about 5 hours or from about 3 hour to about 4 hours or from about 4 hour to about 6 hours or from about 4 hours to 5 hours.

In one example the dome and the foldable metal ring encasing the dome may be tempered dome at 425° C. for 4 h and then freely cooled in the furnace.

In an alternate embodiment the metal strip may be part of the dome itself. In such embodiments the outer lip of the dome can be folded over in a variety of ways to effect an over-moulded dome arrangement.

Other embodiments to encase the dome include but are not limited to by forming a plastic over-moulding of the dome outer rim, by over moulding a plastic vault with a pattern of stiffening ribs on the dome, by using a folded metal casing, by using a ceramic casing, or by self-encasement of the dome by folding back the dome's edges on itself, or a combination of these approaches.

Figure 23:
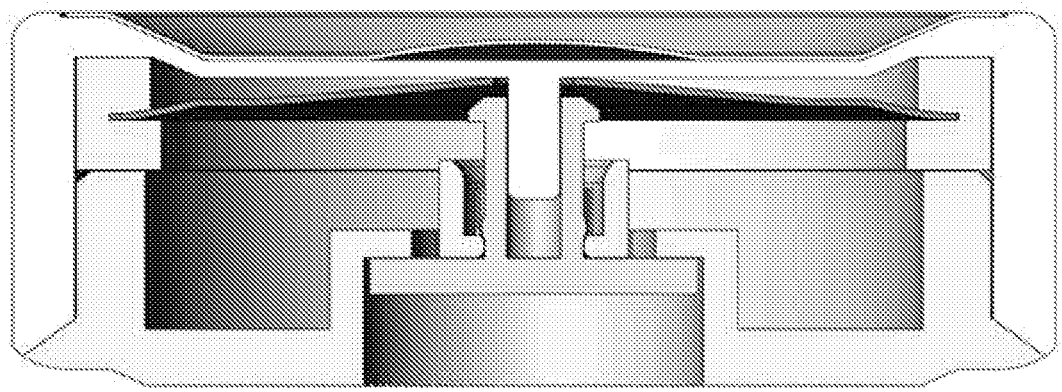
FIG. 23 is a cross-sectional representation of one embodiment of the applicator design, showing the position of the dome system in relation to the patch attach inner mechanism.
Figure 24A:
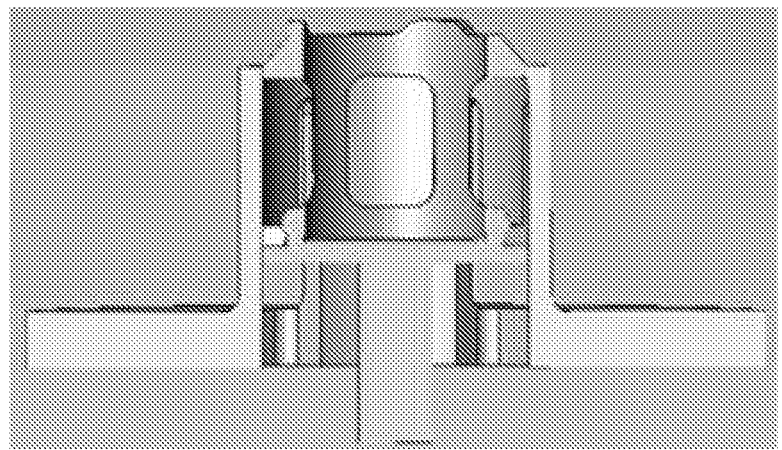
FIG. 24A to 24E are cross-sectional representations of the MAP attach inner mechanism driven by the dome system.
Figure 24B:
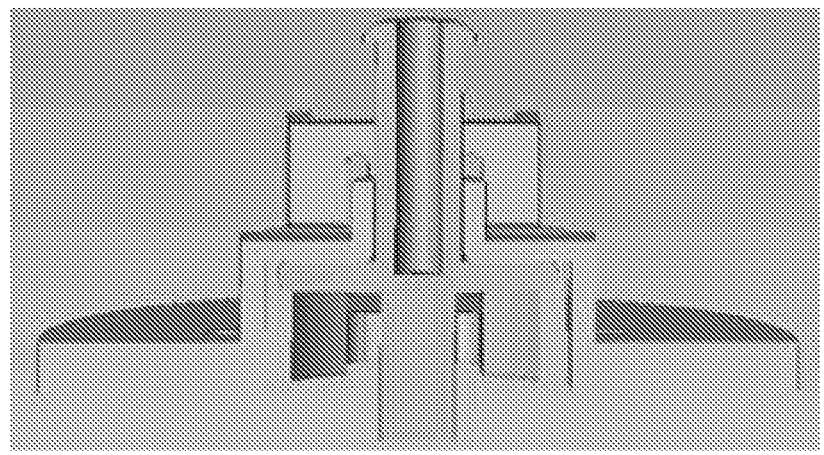
Figure 24C:
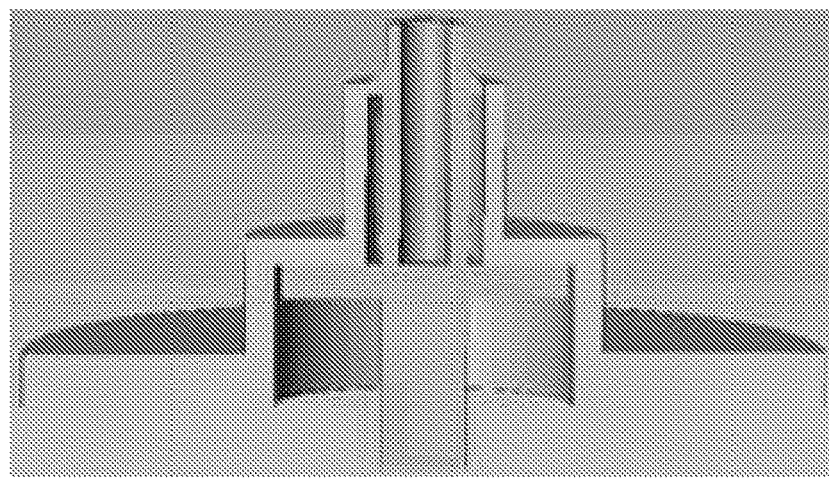
Figure 24D:
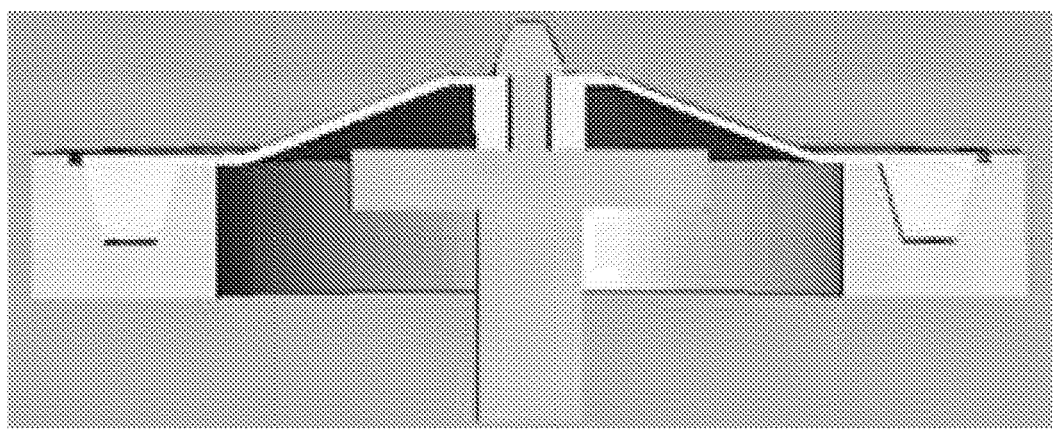
Figure 24E:
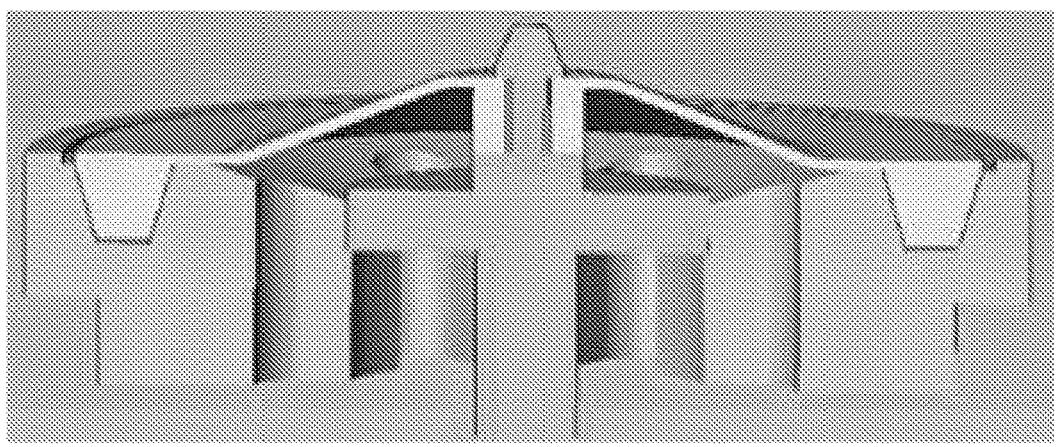
Figure 25:
FIG. 25 is a photograph of a MAP applicator in packaging
Figure 27A:
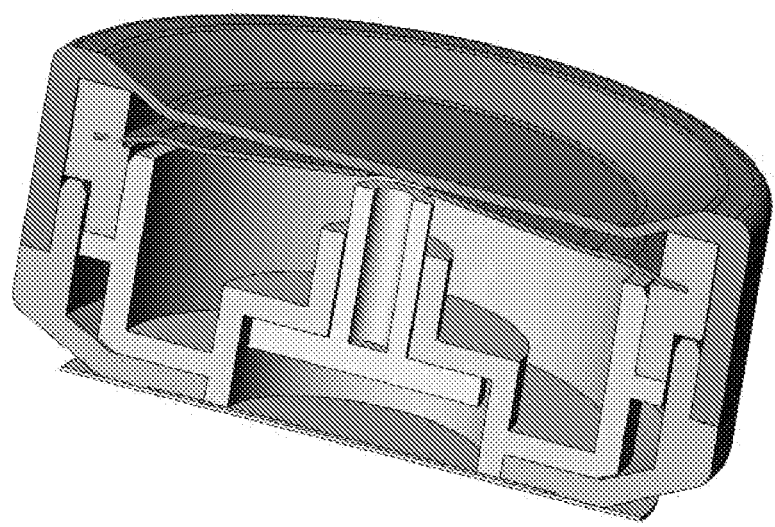
FIGS. 27A and 27B are cross-sectional representations of applicator shells acting as a sterile and low water ingress barrier, leading to the incorporation of the primary packing into the applicator, due to the small inner volume driven by the compact dome system
Figure 27B:
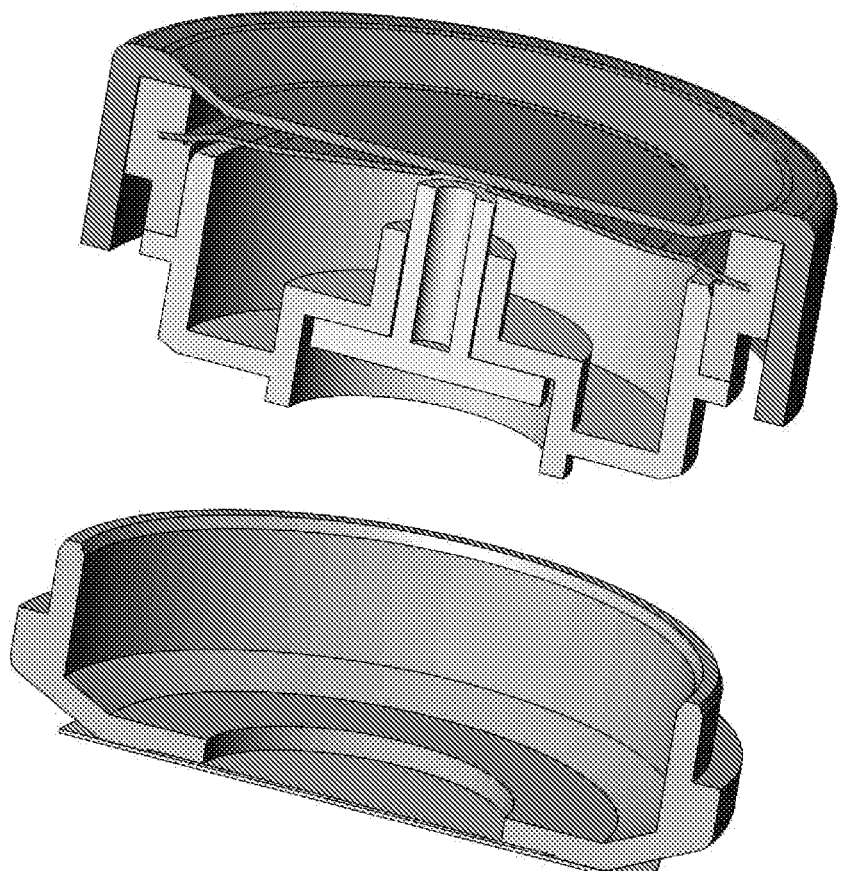
Figure 28A:
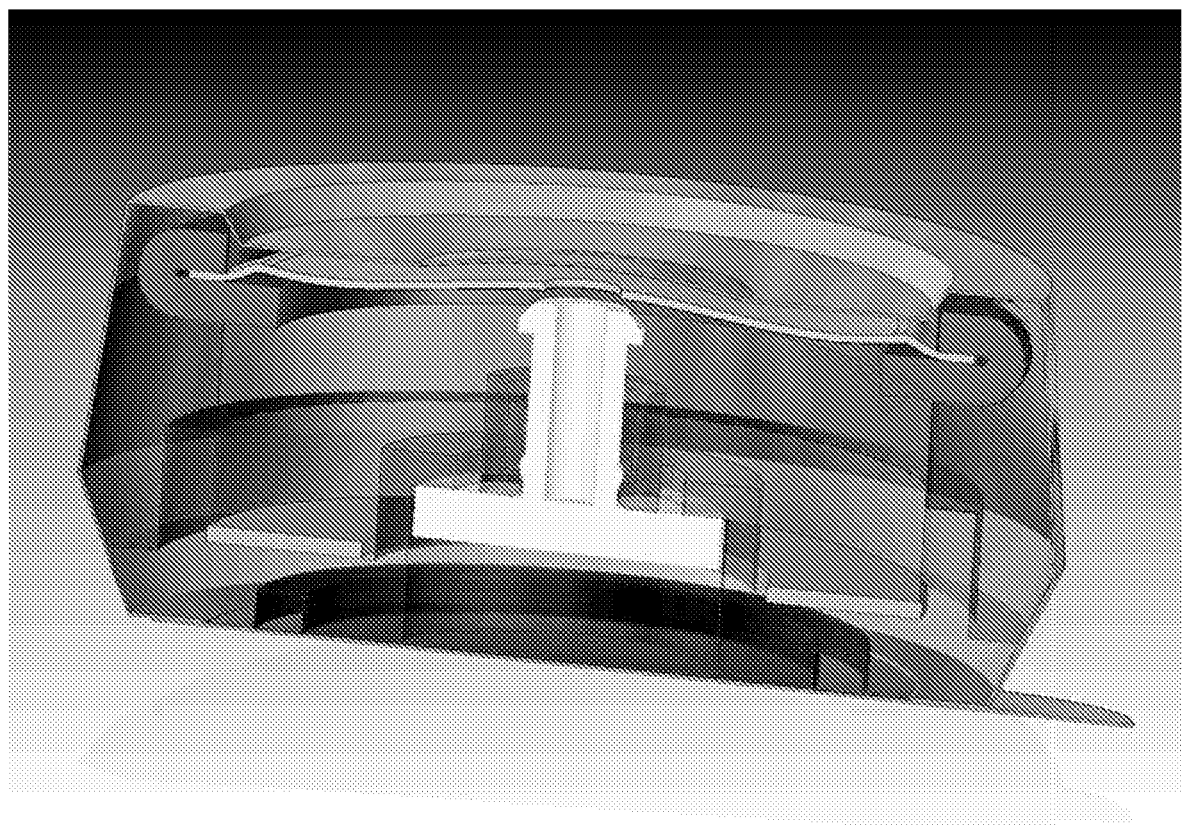
Figure 28B:
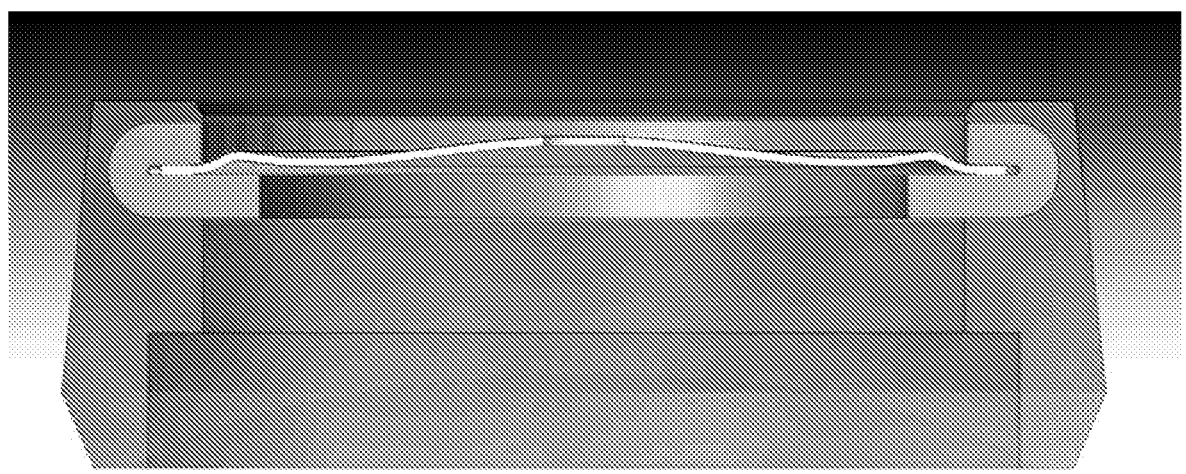

The dome system can be a stand-alone system or a part of an applicator system such as when the system is inserted in an applicator. In a preferred embodiment of a microprojection array applicator the overmoulded dome is placed between the applicator trigger (e.g. flexible top of the applicator) and the microprojection patch held in the patch attach inner mechanism. The dome system could be part of a sub-assembly of the applicator (e.g. dome overmoulded in the top assembly or an overmoulded metal ring folded over the dome in the top assembly. FIG. 23 shows a design of MAP applicator where the dome system (overmoulded dome) is a stand-alone part positioned between the flexible/collapsable top of the applicator and the microprojection patch attach inner mechanism. The top of the applicator acts as the trigger against the dome, but also acts as part of the guiding system of the patch due to an inner spigot that protrudes from the flexible top and inserts in the patch through the centre hole of the encased dome. A slight gap is visible between the dome and the head of the patch which enables the release of the patch from its position in the applicator only when the dome starts to transition, and not before pressure from the user is placed on the applicator's flexible top. FIGS. 24A to 24E demonstrate different embodiments of the patch attach inner mechanisms. All of these dome system designs provide an efficient way of storing the energy in the dome so as to release the patch from its attachment and accelerate the microprojection array to high speeds, while requiring only a small force from the user to trigger the applicator. FIG. 25 is a photograph of an embodiment of the MAP applicator in its packaging. This embodiment of the applicator is very compact having a diameter of 38 mm and a height of 15.8 mm, which provides a user friendly device with less waste generation and raw material use. The devices and methods of the present invention provide a compact dense energy system, with a low trigger actuation providing a high acceleration over a small span. A traditional applicator capable of achieving such speeds, such as one relying on a traditional mono-stable coil/helical compression spring, would require a 10 cm long bulky applicator in order to be able to hold the spring compressed, and accelerate over a long path to propel the patch to the desired speed. Due to its small size, a MAP applicator based on the encased dome can incorporate the sterile and low water ingress barrier and keep the coated MAP in a small dry sterile inner environment. Several barriers and seal designs can be incorporated into the applicator devices as seen in FIGS. 26A, 26B, 27A, 27B, 28A and 28B.

In some embodiments of the microprojection array applicators and methods of applying the microprojection arrays to the skin the parameters for delivering the microprojection array may be, but are not limited to: application momentum 6-22 g·m·s-1, application momentum per projection 1-4 mg·m·s-1, application energy 65·165 mJ; application energy per projection 10·40 µJ; dome mass 0.5-2 g; patch velocity 15-24 m·s-1. In some embodiments of the microprojection array applicators and methods of applying the microprojection arrays to the skin the parameters for the patch may include patch mass 265-1400 mg; patch number of projections 1,000-21,000; tip radius can be from 1 to 100 µm; patch size 4×4 mm to 11×11 mm (round diameter of 10 mm); length of projection 100-300 µm; base width 20-100 µm; projection spacing 70-185 µm; projection density 10-200 projections/mm$^2$.

The speed of the microprojection array as it is projected into the skin depends at least in part upon the density of the projections in the microarray and the area of the array. The range of speeds for the microprojection array entering the skin may be from about 10 m/s to about 50 m/s or from about 10 m/s to about 40 m/s or from about 10 m/s to about 30 m/s or from about 10 m/s to about 25 m/s or from about 10 m/s to about 20 m/s or from about 20 m/s to about 50 m/s or from about 20 m/s to about 40 m/s or from about 20 m/s to about 30 m/s or from about 25 m/s to about 50 m/s or from about 25 m/s to about 40 m/s or from about 25 m/s to about 30 m/s. In preferred embodiments of the microprojection applicators of the present invention the speed of the microprojection array is at least 15 m/s or at least 20 m/s or at least 25 m/s or at least 30 m/s.

The microprojection arrays that the applicator of the present invention projects into the skin may have a variety of shapes and sizes. The microprojection array may be square, circular, rectangular or irregular depending on its use. The microprojection arrays can be varied in size depending on its use. The area of the patch will have an impact on the ability to penetrate the subject, but this must be balanced by the need to induce cell damage over a sufficiently large area to induce a response. Consequently the patch typically has an area of between 0.5×0.5 mm and 20×20 mm, between 0.5×0.5 mm and 15×15 mm and more typically between 1×1 mm and 10×10 mm.

In one embodiment the microprojection array is 10×10 mm. The microprojection arrays may have a density of projections of between 1,000 to 20,000 per cm$^2$ or from 1,000 to 15,000 per cm$^2$, or from 1,000 to 10,000 per cm$^2$ for from 1,000 to 5,000 per cm$^2$, or from 2,500 to 20,000 per cm$^2$ or from 2,500 to 15,000 per cm$^2$ or from 2,500 to 10,000 per cm$^2$ or from 2,500 to 7,500 per cm$^2$ or from 2,500 to 5,000 per cm$^2$ or from 5,000 to 20,000 per cm$^2$ or from 5,000 to 15,000 per cm$^2$ or from 5,000 to 10,000 per cm$^2$ or from 5,000 to 9,000 per cm$^2$ or from 5,000 to 8,000 per cm$^2$ or from 5,000 to 7,000 per cm$^2$ or from 5,000 to 6,000 per cm$^2$.

The applicators of the present invention are often utilized to project high density microprojection arrays into the skin. Such high density arrays are microprojection arrays of sufficient size and density such that forces that can be applied manually will be insufficient to overcome the elasticity of the skin. The projections are typically separated by between 10 µm and 200 µm, between 30 µm and 150 µm, between 50 µm and 120 µm and more typically between 70 µm and 100 µm, leading to patches having between 10 and 1000 projections per mm$^2$ and more typically between 100 and 3000 projections per mm$^2$, and in one specific example approximately 20,000 per cm$^2$.

The length of the projections may be from 100 µm to 700 µm or from 100 µm to 600 µm or from 100 µm to 500 µm or from 100 µm to 400 µm or from 100 µm to 300 µm or from 100 µm to 250 µm or from 100 µm to 200 µm or from 150 µm to 700 µm or from 150 µm to 600 µm or from 150 µm to 500 µm or from 150 µm to 400 µm or from 150 µm to 300 µm or from 150 µm to 250 µm or from 150 µm to 200 µm or from 200 µm to 700 µm or from 200 µm to 600 µm or from 200 µm to 500 µm or from 200 µm to 400 µm or from 200 µm to 300 µm or from 200 µm to 250 µm or from 225 µm to 700 µm or from 225 µm to 600 µm or from 225 µm to 500 µm or from 225 µm to 400 µm or from 225 µm to 300 µm or from 225 µm to 250 µm or from 250 µm to 700 µm or from 250 µm to 600 µm or from 250 µm to 500 µm or from 250 µm to 400 µm or from 250 µm to 300 µm. The projections may have a step shoulder between the cone and pillar of the projection. The microprojection array may be made of any suitable materials including but not limited to silicon, polymers, and plastic. In silicon embodiments the base thickness is about 60 um or silicon with a thin (1 mm) polymer backing. The overall mass of some embodiments of the microprojection array is about 0.3 gm. The microprojection array may have bevelled edges to reduce peak stresses on the edge of the array. The patch can be quartered or subdivided by other ratios to reduce the stress load on the patch and mitigate patch breakage. Polymer embodiments may have reduced mass. The microprojection array may also have an overall weakly convex shape of the patch to improve the mechanical engagement with skin and mitigate the effect of high speed rippling application: a 'high velocity/low mass' system. The microprojection array may have a mass of less than 1 gram, or less than 0.9 grams or less than 0.8 grams or less than 0.7 grams, or less than 0.6 grams or less than 0.5 grams or less than 0.6 grams, or less than 0.5 grams or less than 0.4 grams or less than 0.3 grams or less than 0.2 grams or less than 0.1 grams or less than 0.05 grams. The microprojection array may have a mass of about 0.05 grams to about 2 grams, or from about 0.05 grams to about 1.5 grams or from about 0.05 grams to about 1.0 grams or from about 0.05 grams to about 0.9 grams, or from about 0.05 grams to about 0.8 grams or from about 0.05 grams to about 0.7 grams, or from about 0.05 grams to about 0.6 grams or from about 0.05 grams to about 0.5 grams or from about 0.05 grams to about 0.4 grams, or from about 0.05 grams to about 0.3 grams or from about 0.05 grams to about 0.2 grams, or from about 0.05 grams to about 0.1 grams or from about 0.1 grams to about 1.0 grams or from about 0.1 grams to about 0.9 grams, or from about 0.1 grams to about 0.8 grams or from about 0.1 grams to about 0.7 grams, or from about 0.1 grams to about 0.6 grams or from about 0.1 grams to about 0.5 grams or from about 0.1 grams to about 0.4 grams, or from about 0.1 grams to about 0.3 grams or from about 0.1 grams to about 0.2 grams. In one embodiment of the applicator/microprojection system the mass of the array is about 0.3 grams, the array is projected at a velocity of about 20-26 m/s by the applicator.

In some embodiments of the microprojection array applicators and methods of applying the microprojection arrays to the skin the parameters for delivering the microprojection array may be: application momentum 6-22 g·m·s-1, application momentum per projection 1-4 mg·m·s-1, application energy 65-165 mJ; application energy per projection 10-40 µJ; dome mass 0.5-2 g; patch velocity 15-24 m·s-1. In some embodiments of the microprojection array applicators and methods of applying the microprojection arrays to the skin the parameters for the patch may include patch mass 265-1400 mg; patch number of projections 5,000-21,000; tip radius; patch size 4×4 mm to 11×11 mm (round diameter of 10 mm); length of projection 100-300 µm; base width 20-50 µm; projection spacing 70-185 µm; projection density 10-200 projections/mm$^2$.

The present invention relates to microprojection array applicators that provide application of microprojection arrays to the skin for the delivery of substances in particular the delivery of vaccine antigens. The present invention also relates to methods of using the microprojection array applicators for applying microprojection arrays to the skin of a subject. The applicators and methods of the present invention are especially useful for the delivery of high density microprojection arrays to the skin surface. The applicators and methods of the present invention are also useful for the delivery of high density microprojection arrays at a high rate of speed to the skin surface. The present invention is designed to achieve tolerable penetration for high density, low mass microprojection arrays (>5,000/cm$^2$) that are delivered to the skin at high velocities.

The applicators of the present invention may be comprised of a sterile housing in which an encased dome and one or more microprojection array(s) are contained. The housing may preferably be made of plastic or a metallic material such as steel or aluminium or a fibrous paper based material or a laminate including any of these materials. The bottom of the microprojection array applicator is covered with a foil sheet to protect the membrane and to keep the device sterile. The housing encompasses the inner workings of the applicator. The housing has an upper and lower section. The housing may have a collapsible section which acts as a trigger to activate the dome(s). The collapsible section or sections of the housing may be on upper section of the device or incorporated into the bottom of the housing. Preferably the flexible or collapsible section of the housing is actuated through a force applied by hand such that application of the microprojection array is comfortable to both the patient and the person activating the applicator. In one embodiment of the applicator of the present invention the force is applied to the applicator in a fashion that is substantially perpendicular to the skin to which the microprojection array is applied such that the force travels down through the encased dome. Alternatively, the activation force could be applied in a direction substantially parallel to the skin by a mechanism that may be actuated between the thumb and forefinger. The mechanism by which the applicator is activated should not cause discomfort to the patient.

Figure 35:
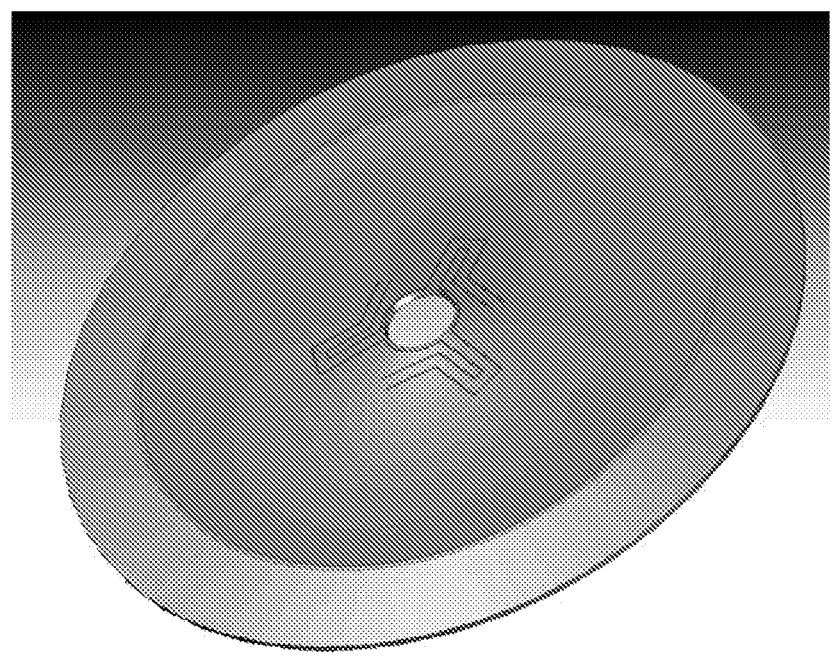
FIG. 35 is a representation of a dome into which the spring feature is incorporated such that the microprojection array could be held directly by the dome.
Figure 36A:
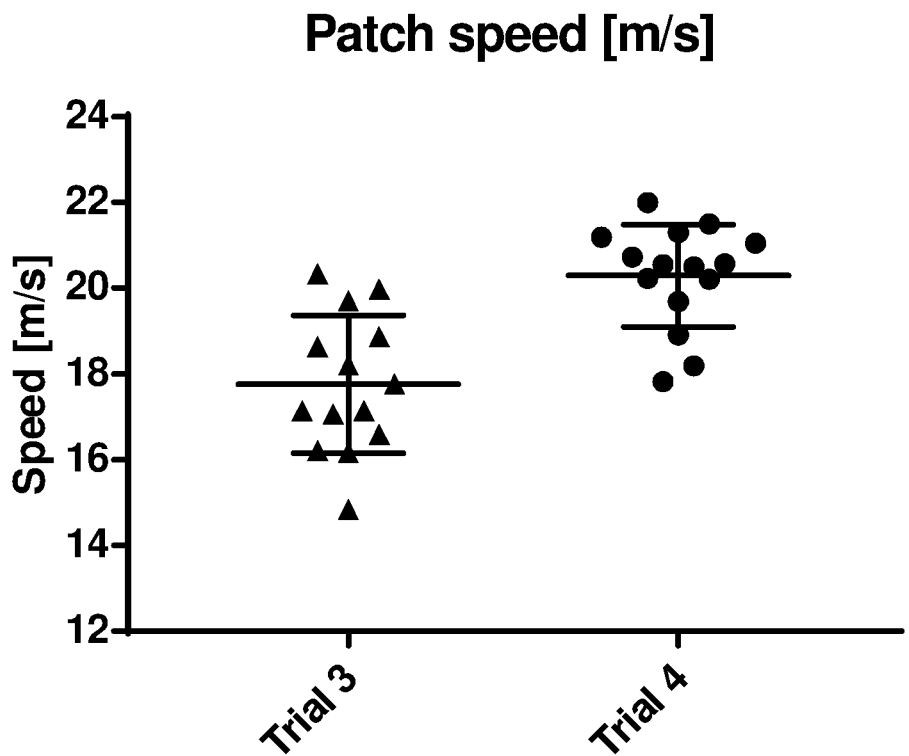
FIG. 36A is a plot of the patch speed for each trial.
Figure 36B:
FIG. 36B is a plot of the trigger force.

The microprojection array maybe propelled from the device after the device is activated such that the microprojection array transits a distance between the applicator device and the target skin and then penetrates the skin. In essence, the microprojection array may be propelled across some distance and then penetrate the target skin. In one embodiment of the applicator where the microprojection array is discharged from the device, the microprojection array could be tethered to a mechanism that protrudes through the dome such that when the dome is activated the mechanism releases the microprojection array with sufficient force to propel the array into the skin. For example, the microprojection array could be fixed to a guide shaft (spigot) that fits through a center hole in the dome. The spigot enables guided travel of the microprojection array to ensure that the microprojection array contacts the skin in a flat manner, so that the microprojection array and the skin meet flush. In this embodiment the microprojection array and the dome are disconnected such that the large mass of the ring is not attached to the array. This should permit a high speed, low mass, pain free delivery of the microprojection array to the skin. In another embodiment the microprojection array may be attached to a low mass tether. In this embodiment the microprojection array is either not in direct contact with the dome or the only contact between the dome and the microprojection array is when the dome impacts the array sending the array toward the skin. In these cases the microprojection array can be struck at the point where the dome achieves maximum velocity and the mass of the dome does not impact the skin of the patient. In preferred embodiments of the applicator device of the present invention the microprojection array is either propelled without attachment to the device or attached to the device via a low mass connector such as a tether. In an alternative embodiment the patch insertion and flight guiding may be accomplished with springs instead of a sliding spigot (See FIGS. 34A to 34G). Another alternative is to insert the patch directly in the dome instead of utilizing a separate part by having the spring feature incorporated into the dome. This embodiment can be by manufactured by laser cutting the domes (See FIG. 35).

Figure 40A:
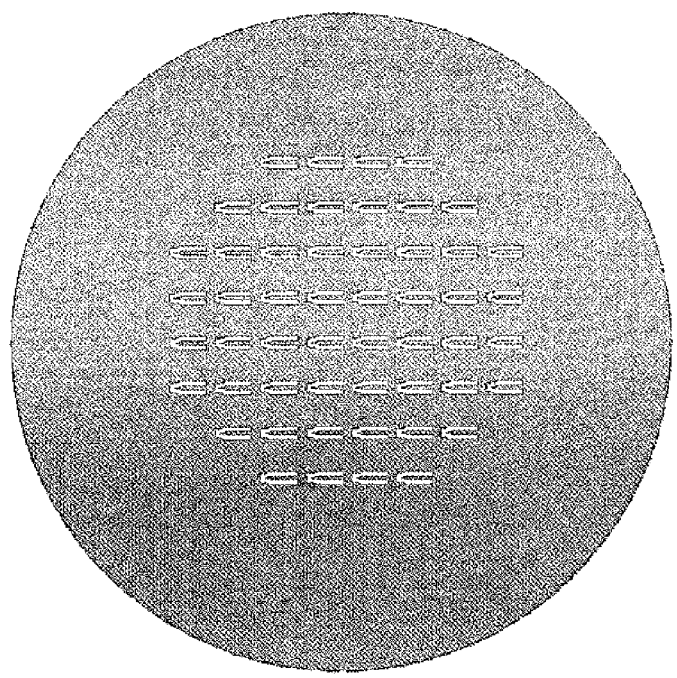
FIG. 40A shows a top view of microprojections integrated into a dome.
Figure 40B:
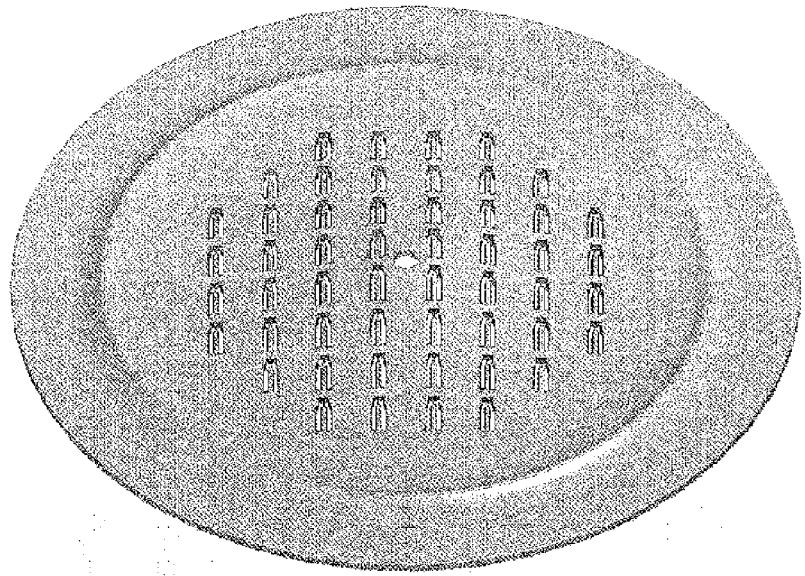
FIG. 40B shows a partially inclined view of microprojections integrated into a dome.
Figure 40C:
FIG. 40C shows a side view of microprojections integrated into a dome.
Figure 40D:
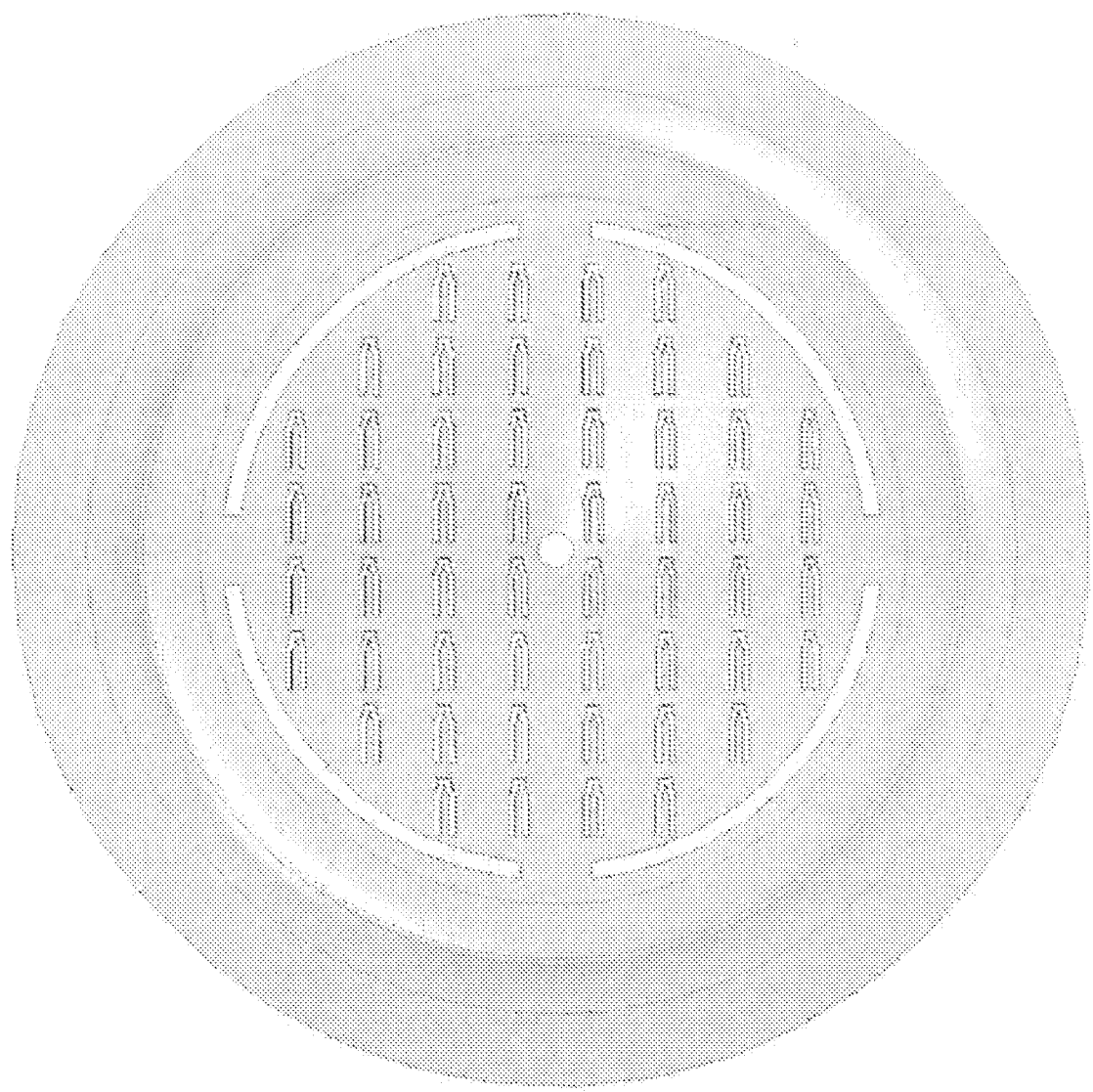
FIG. 40D shows a top view of microprojections integrated into a dome where the cut-out is held in place by tabs.

In an alternate embodiment the patch or microprojection array may be incorporated directly into the dome material (See FIGS. 40A 40D). In this embodiment the dome may be over-moulded or inserted in a skin contacting holding ring moulded in a desiccant compound. Sterile and a low water ingress barrier could be provided by a small foil pouch, blister or plastic shell. Only the dome would be contaminated after application and the dome could be directly extracted from the skin and decontaminated. The domes with the microprojections could be manufactured by high speed stamping on progressive tools (e.g. Bruderer Press at about 500 to 2000 strokes per minute) offering high throughput and scalability. Shape cutting and stamping in a dome shape can be accomplished while bending out the projections can be done in the same tool. Other methods of manufacturing include but are not limited to embossing, injection moulding, casting, photochemical etching, electrochemical machining, electric discharge machining, precision stamping, high-speed computer assisted controlled milling, Swiss screw machining, soft lithography, directional chemically assisted ion etching or a combination of methods. The patch area may be in the center of the dome which could have a cut-around held in place by a few tabs in order to permit acceleration of the patch with minimal bending of the dome. Coating of the projections may be accomplished by multi-nozzle drop dispensing on the loaded dome. A securing mechanism with an array of openings corresponding to the microprojections could be used to locate the projections under the printer head.

The present invention further relates to microprojection applicators in which a membrane is introduced between the microprojection array and the skin surface to which the array is applied. The membrane flattens the skin to which the microprojection array is applied and absorbs the initial impact from the microprojection applicator. The use of a membrane results in an even surface for application regardless of skin condition or thickness and provides even penetration of the microprojections across the skin surface. Microprojection application through a membrane has distinct advantages over application of a microprojection array directly into the skin. It allows the skin to be smoothed flat creating a consistent and uniform application surface. The use of a membrane over the microprojection array allows a device design whereby the microprojection array can be kept in a sterile environment until the membrane is pierced at the time of application. The membrane also allows the patch to be removed from the skin with the applicator and provides confirmation of the application of the microprojection array via the penetration pattern visible on the membrane surface. The membrane also reduces the need for external packaging to maintain sterility thereby reducing packaging waste. Preferably the membrane is non-permeable. The membrane may be made of but is not limited to polymer films, organic and organic fiber films or laminates. Preferably the membrane is from about 2 to about 20 µm or from about 5 to 20 µm or from about 10 to about 20 µm or from about 5 to 10 µm in thickness.

In an alternate embodiment of the present applicator devices of the invention the microprojections of the microprojection array may be uncoated and the membrane may be coated by a substance such as a vaccine. In this embodiment the applicator pushes the microprojections of the microprojection array through the vaccine coated membrane thereby delivering the vaccine to the skin of a patient by penetrating the membrane. Alternatively the membrane and microprojection array may be designed such that the microprojections do not penetrated the membrane but rather force the membrane into the skin where the vaccine can be delivered. In such an embodiment the tips of the microprojections may be modified so that they are not so sharp as to penetrated the membrane but still strong enough to penetrate the skin (See FIG. 31). In this embodiment the ductile membrane with the vaccine coating on the side of the membrane facing the skin will form a disposable element forming an impenetrable barrier between the microprojections and the skin during application. The coated membrane delivers the coating to the skin via the patch microprojections locally deforming but not penetrating the membrane. In these embodiments the entire applicator or parts of the applicator may be re-usable. The membrane may be coated by various coating techniques including but not limited to gas-jetting or ink jet coating or other printing means. The coating may be applied as a layer or as "dots" on the membrane that align with the microprojections of the microprojection array. In some embodiments the membrane may be dissolvable and provide for an extended release of coating into the skin.

The membrane may also be covered by a label or covering which serves to protect and keep sterile the membrane and the microprojection array. The label may be in the form of a foil seal or a mesh that can be removed just prior to the use of the microprojection array applicator. In embodiments where a membrane is not used the label may cover the microprojection array.

As the use of microprojection arrays to deliver vaccines to the skin may cause erythema, oedema and visual discoloration of the skin the addition of various substances could be added to the applicator, for example between the membrane and the foil seal or mesh. See FIGS. 32A to 32D. Alternatively the substances could be impregnated in the membrane or foil seal/mesh. Such substances include but are not limited to moisturizing gel, sterilizing gel, anaesthetic agents, antibiotics, anti-inflammatory agents, therapeutic or prophylactic substances to improve wound healing or combinations thereof. In alternative embodiments the substances could include vaccine adjuvants or dyes to reduce the visual impact of erythema or dyes to indicate delivery of the vaccine or dyes to indicate what vaccine has been delivered.

A desiccant film may be included in the microprojection array applicator to maintain the internal environment and water content of the coating. One method of incorporating a desiccant into the applicator is by incorporating the desiccant into the membrane which may be layered under the foil seal or internal to the device housing.

EXAMPLES

Example 1

Performance of Non-Encased Dome

A high performance dome was tested for [11R51 0.3 mm steel-T6.2 stamping profile], standalone performance which is controlled displacement at constant speed, load recording. In FIG. 1 the loading of the dome is the black trace and the triggering of the dome is the blue trace. Different zones of strain-stress (jig setting, elastic behaviour and buckling increase are explained on the triggering trace. Performance: loading of the dome 11.32 m/s for 197.89 N; triggering 22.17 m/s for a peak force (trigger force) of 95.46 N.

Example 2

Triggering of Encased Dome

FIG. 1 is a graph that shows the triggering of a high performance dome [11R51 0.3 mm-T6.2], that has been over moulded with 15% Glass filled nylon 6 high impact-dimensions [OD Ø33.4 mm, thickness 4.9 mm, convex IDØ27.9, concave IDØ27.1 (of the loaded dome)]. The beginning of the graph is an artefact from the test method: the jig and the sample are loaded at 2N and permitted to settle, then the displacement was reset to zero and the load was then increased. Similarly, the end of the graph corresponds to the cell force losing contact with the dome when it triggers, and following rebounds. Performance: 23.36 m/s for a peak force (trigger force) of 20.62 N.

Example 3

Trigger Force Versus Trigger Speed

Figure 29:
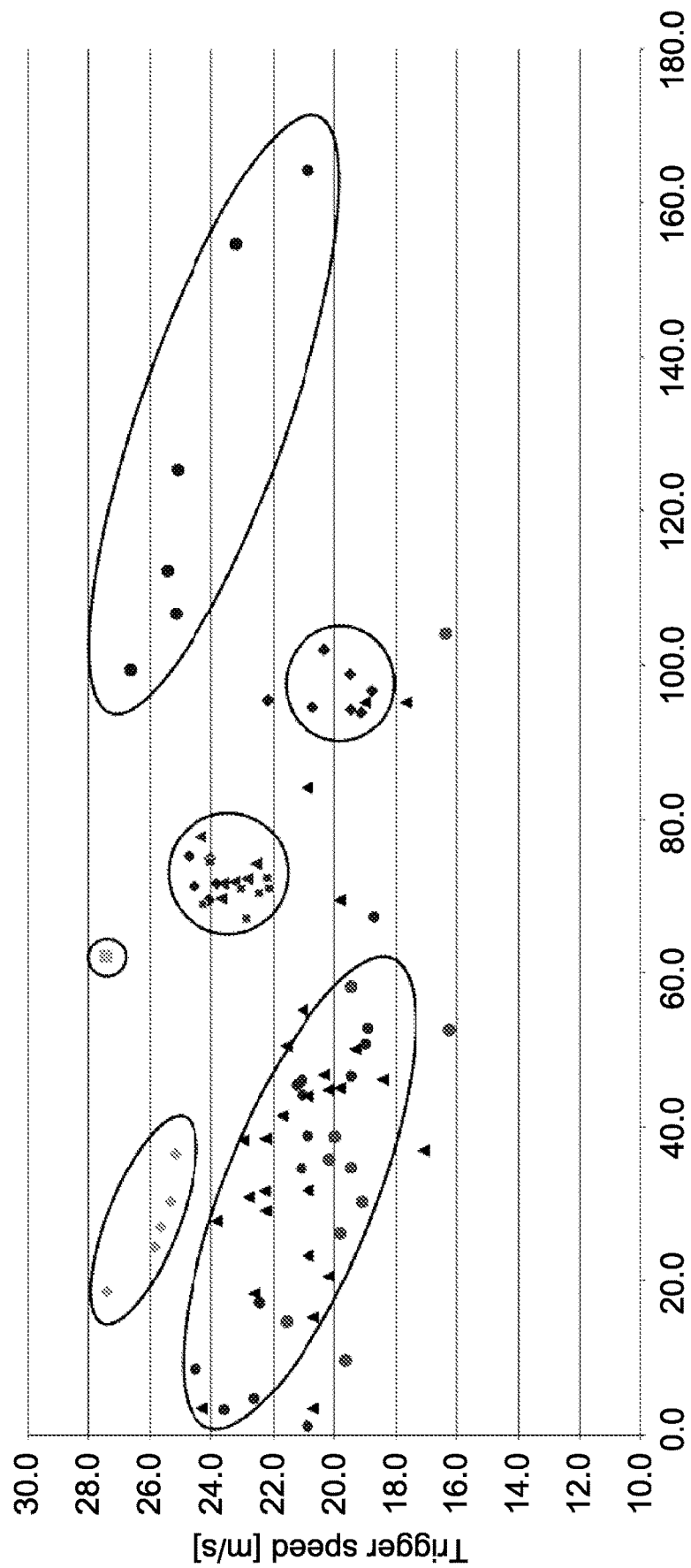
FIG. 29 is a plot of trigger speed versus trigger force of several different design embodiments.
Figure 30B:
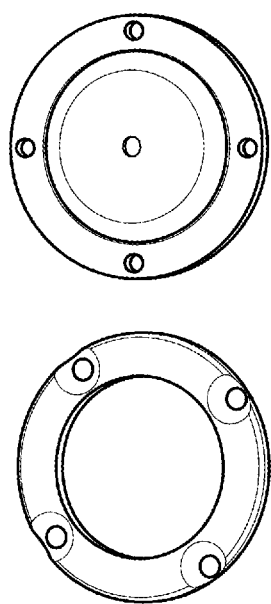
FIG. 30B is photograph of one embodiment of the ring and dome structure partially assembled.
Figure 30D:
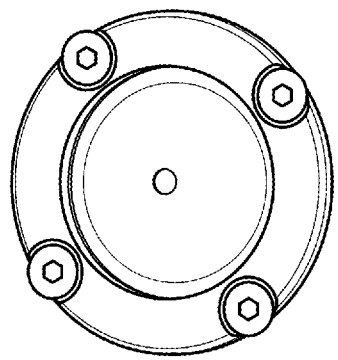
FIG. 30D is photograph of one embodiment of the ring and dome structure assembled and unloaded.
Figure 30A:
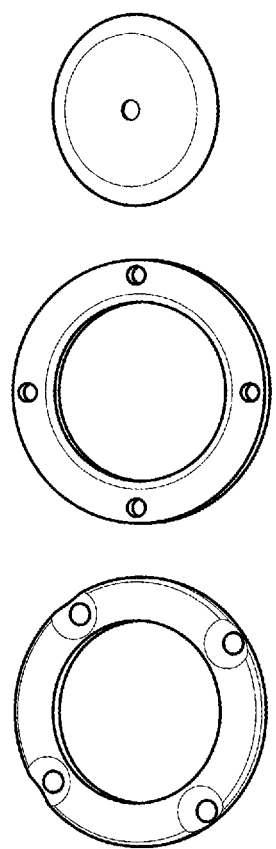
FIG. 30A is a photograph of one embodiment of the ring and dome structure diassembled.
Figure 30C:
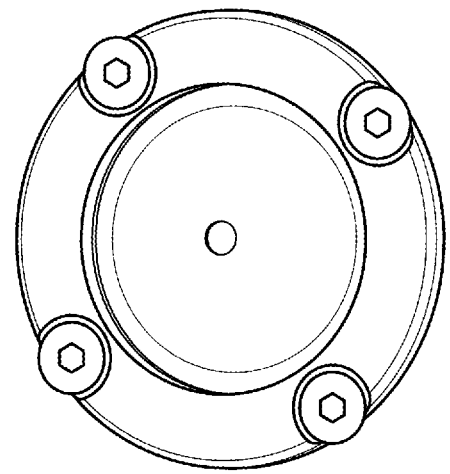
FIG. 30C is photograph of one embodiment of the ring and dome structure assembled and loaded.
Figure 33:
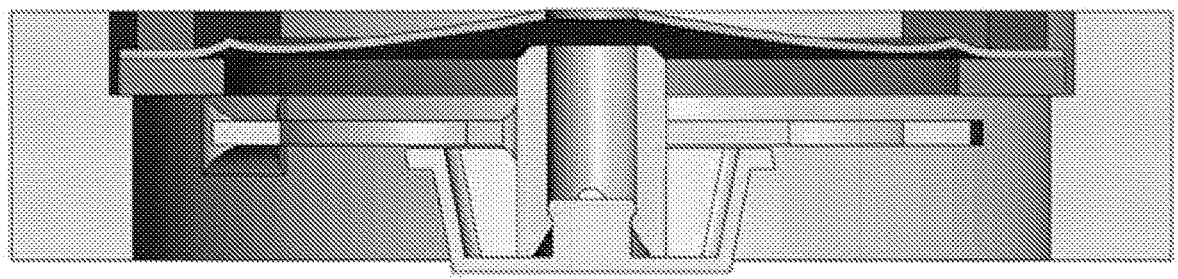
FIG. 33 is cross-sectional representations of applicator in which the microprojection array is held by plastic springs that guide the arrays flight path after being propelled by the dome.
Figure 34A:
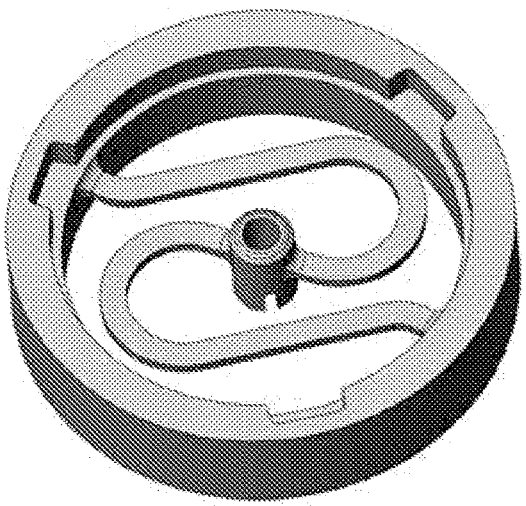
FIG. 34A to 34D show different embodiments of plastic springs that hold the microprojection array in place and which guide the microprojection array on its path.
Figure 34B:
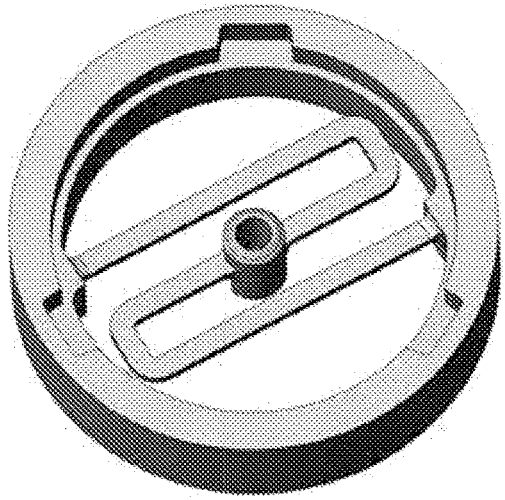
Figure 34C:
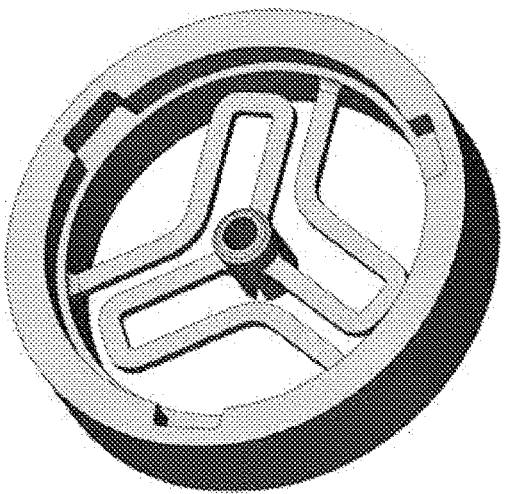
Figure 34D:
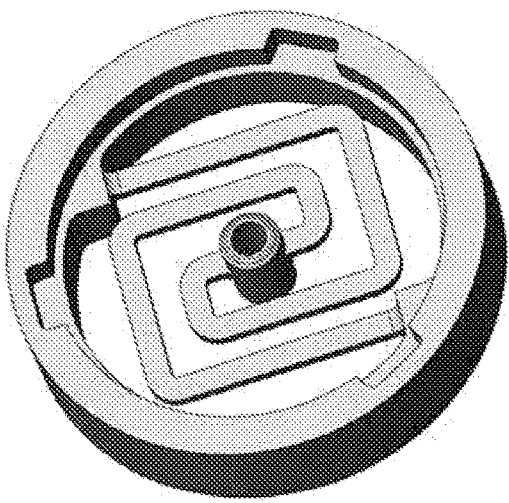
Figure 34E:
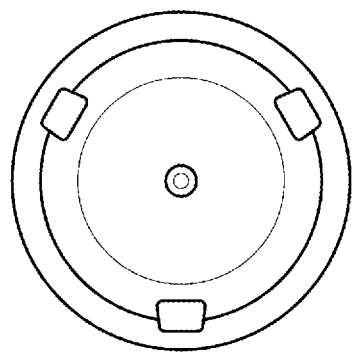
FIG. 34E is a photograph of a dome with three tabs is a plastic housing.
Figure 34F:
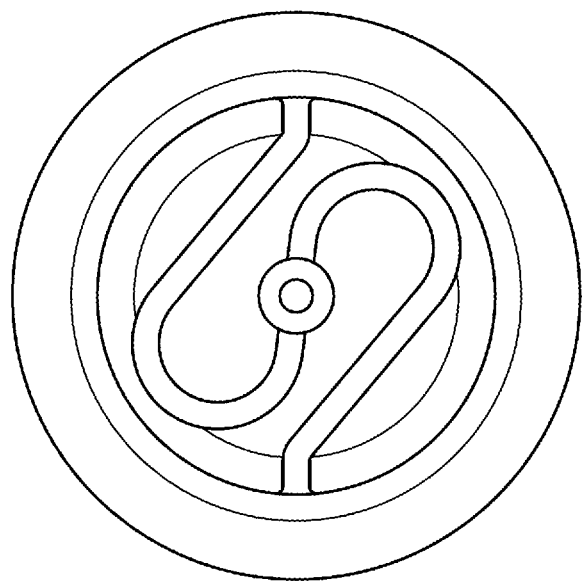
FIG. 34F is a photograph of one embodiment of a plastic spring in a housing with the dome in place.
Figure 34G:
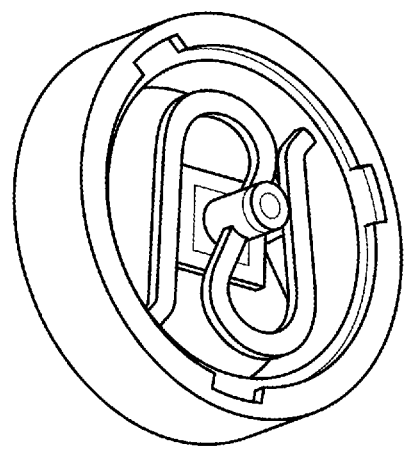
FIG. 34G is a photograph of one embodiment of a plastic spring in a housing without the dome.

The graph in FIG. 29 shows the trigger force versus trigger speed for a variety of conditions and dome designs including treating the domes with heat and various gases.

The normal plain untreated new dome is centred around a trigger speed of 20±2 m/s with a trigger force of 100N. When heat treated, the trigger speed increases and force trigger force decreases to 24±2 m/s and 70N respectively. Dome stability is also improved.

When the dome is encased in a metal folding ring, the speed is preserved in the 20±2 m/s range but the force can be tailored down to anywhere between 0-60N, a beneficial increase in speed may take place for lower forces. When heat treated, the folded domes also experience a decrease in trigger force to about 20-40 N and an increase in speed up to 25 to 26 m/s.

When welded with rings to increase the outer rim thickness, the speed can be increased but the force is increased too, heat treatment helps in lowering the trigger force at the 60 N mark. Combinations of 1 or 2 rings (each side of the domes), with different IDs (Ø24.5 and 27.4 mm) and thickness (0.5 and 0.8 mm) were also tested.

When overmoulded in plastic, the speed of the dome is preserved in the 20±2 m/s range but the force can be tailored down to anywhere between 0 to 60N, an increase in speed may take place for lower forces. However to achieve stability, engineering plastics are required.

Example 4

Trigger Force Versus Trigger Speed

Figure 37A:
FIG. 37A is a picture of a dome encased in a plastic applicator by using ultrasound crimping.
Figure 37B:
FIG. 37B is a magnified picture of a dome encased in a plastic applicator by using ultrasound crimping.
Figure 38A:
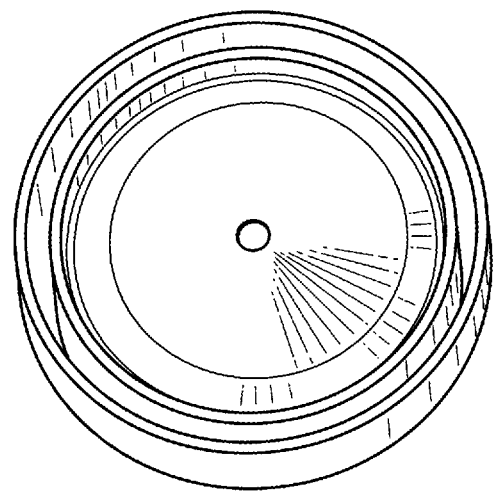
FIG. 38A is a picture of the applicator after ultrasound crimping.
Figure 38B:
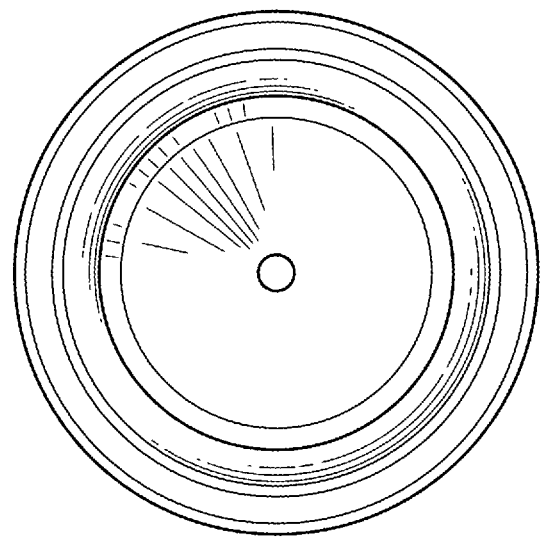
FIG. 38B is a picture of the applicator after ultrasound crimping in which sonotrodes are visible.
Figure 38C:
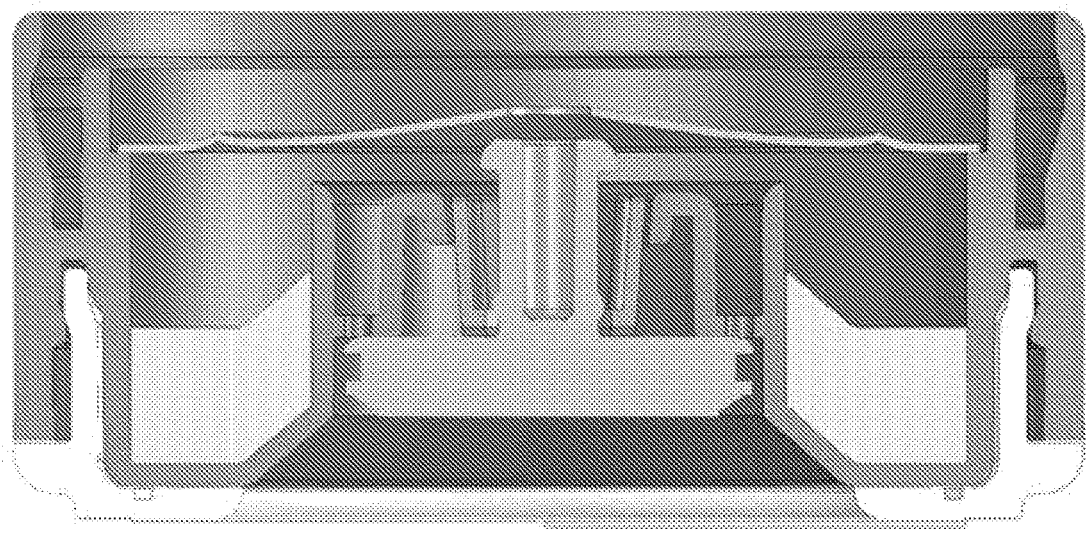
FIG. 38C is a schematic of a side view of the applicator after ultrasound crimping.
Figure 38D:
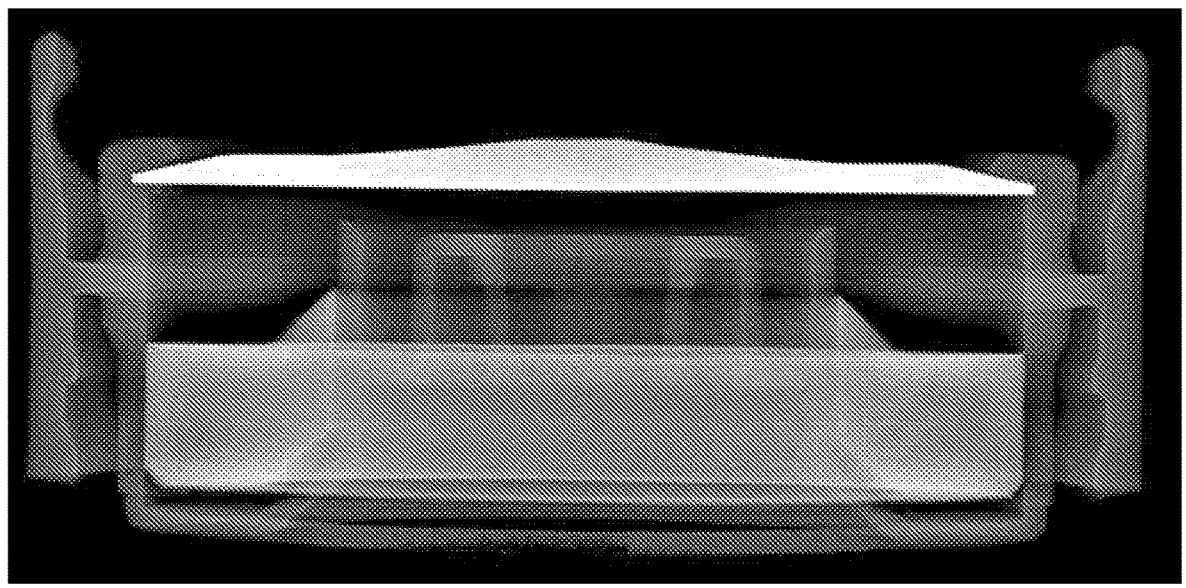
FIG. 38D is an x-ray of a side view of the applicator after ultrasound crimping.
Figure 39A:
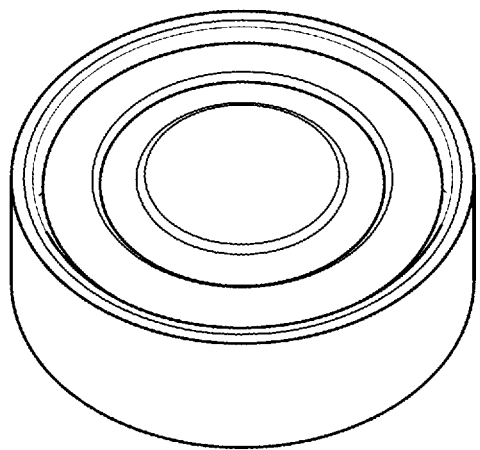
FIG. 39A shows the top view of a picture of an applicator for a microprojection array.
Figure 39B:
FIG. 39B shows a top view of a picture of an applicator in which the microprojection array is being applied to a patient's skin.

Two different trials were conducted the first in which 900 watts at 35 Hz and 400 ms hold time was performed (Trial 3). The second in which 1500 watts at 20 Hz and 400 ms hold time was performed (Trial 4). FIG. 37A is a plot of the patch speed for each trial and FIG. 37B is a plot of the trigger force for each trial.

Within this disclosure, any indication that a feature is optional is intended provide adequate support (e.g., under 35 U.S.C. 112 or Art. 83 and 84 of EPC) for claims that include closed or exclusive or negative language with reference to the optional feature. Exclusive language specifically excludes the particular recited feature from including any additional subject matter. For example, if it is indicated that A can be drug X, such language is intended to provide support for a claim that explicitly specifies that A consists of X alone, or that A does not include any other drugs besides X. "Negative" language explicitly excludes the optional feature itself from the scope of the claims. For example, if it is indicated that element A can include X, such language is intended to provide support for a claim that explicitly specifies that A does not include X. Non-limiting examples of exclusive or negative terms include "only," "solely," "consisting of," "consisting essentially of," "alone," "without", "in the absence of (e.g., other items of the same type, structure and/or function)" "excluding," "not including", "not", "cannot," or any combination and/or variation of such language.

Similarly, referents such as "a," "an," "said," or "the," are intended to support both single and/or plural occurrences unless the context indicates otherwise. For example "a dog" is intended to include support for one dog, no more than one dog, at least one dog, a plurality of dogs, etc. Non-limiting examples of qualifying terms that indicate singularity include "a single", "one," "alone", "only one," "not more than one", etc. Non-limiting examples of qualifying terms that indicate (potential or actual) plurality include "at least one," "one or more," "more than one," "two or more," "a multiplicity," "a plurality," "any combination of," "any permutation of," "any one or more of," etc. Claims or descriptions that include "or" between one or more members of a group are considered satisfied if one, more than one, or all of the group members are present in, employed in, or otherwise relevant to a given product or process unless indicated to the contrary or otherwise evident from the context.

Where ranges are given herein, the endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While this invention has been particularly shown and described with references to example embodiments thereof, it will be understood by those skilled in the art that the various changes in form and details may be made therein without departing from the scope of the invention encompassed by the appended claims.

Further advantages of the present immunological compositions and adjuvants of the present invention can be achieved by those skilled in the art based upon the embodiments described herein and are thus specifically within the scope of the present invention.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers. As used herein and unless otherwise stated, the term "approximately" means±20%.

It will of course be realised that whilst the above has been given by way of an illustrative example of this invention, all such and other modifications and variations hereto, as would be apparent to persons skilled in the art, are deemed to fall within the broad scope and ambit of this invention as is herein set forth.

The invention claimed is:

1. A device for applying a microprojection array to the skin of a mammal, the device comprising a housing which comprises a top shell having a collapsible trigger operably linked to a pre-loaded dome, and a bottom shell and a spring holding the microprojection array, wherein the pre-loaded dome is encased in the housing such that when the trigger is collapsed the dome transitions from a loaded position to an unloaded position, thereby contacting the spring and propelling the microprojection array through a space between the device and the mammal's skin and into the mammal's skin.

2. The device of claim 1, wherein the dome has a flattened outer edge.

3. The device of claim 2, wherein the flattened outer edge is circumferential.

4. The device of claim 1, wherein the microprojection array has a mass from about 0.1 grams to about 0.5 grams.

5. The device of claim 1, wherein the microprojection array has a mass of about 0.3 grams.

6. The device of claim 1, wherein the device further comprises a foil lid that covers the bottom shell.

7. The device of claim 6, wherein the foil lid contains one or more substances.

8. The device of claim 7, wherein the substance is a desiccant.

9. The device of claim 1, wherein the dome is made of austenitic steel from 1 to 0.5 mm thick.

10. The device of claim 9, wherein the dome is 0.3 mm thick.

11. The device of claim 1, wherein the microprojection array is propelled at 10-30 m/s.

12. The device of claim 1, wherein the microprojection array is propelled at 20-26 m/s.

13. The device of claim 1, wherein the dome has been heat treated.

14. The device of claim 13, wherein the heat treatment is from about 300 to 450° C.

\* \* \* \* \*

UNITED STATES PATENT AND TRADEMARK OFFICE
CERTIFICATE OF CORRECTION

| | | |
|---|---|---|
| PATENT NO. | : 11,464,957 B2 | Page 1 of 1 |
| APPLICATION NO. | : 16/636467 | |
| DATED | : October 11, 2022 | |
| INVENTOR(S) | : Pierre Armand Vincent Lemaire | |

It is certified that error appears in the above-identified patent and that said Letters Patent is hereby corrected as shown below:

In the Claims

<u>Column 30, Claim 4, Line 48:</u>
"the microproj ection" should read: --the microprojection--.

<u>Column 30, Claim 5, Line 50:</u>
"the microproj ection" should read: --the microprojection--.

Signed and Sealed this
Thirty-first Day of December, 2024

Derrick Brent
*Acting Director of the United States Patent and Trademark Office*